US010105422B2

(12) United States Patent
Hajjar et al.

(10) Patent No.: US 10,105,422 B2
(45) Date of Patent: Oct. 23, 2018

(54) SUMOYLATION OF SERCA2A AND CARDIOVASCULAR DISEASE

(71) Applicant: Icahn School of Medicine at Mount Sinai, New York, NY (US)

(72) Inventors: Roger Joseph Hajjar, Tenafly, NJ (US); Chang Won Kho, New York, NY (US); Ah Young Lee, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 15/281,269

(22) Filed: Sep. 30, 2016

(65) Prior Publication Data

US 2017/0014494 A1 Jan. 19, 2017

Related U.S. Application Data

(60) Continuation of application No. 14/798,357, filed on Jul. 13, 2015, which is a division of application No. 14/232,105, filed as application No. PCT/US2012/046777 on Jul. 13, 2012, now abandoned.

(60) Provisional application No. 61/507,526, filed on Jul. 13, 2011.

(51) Int. Cl.
| | |
|---|---|
| *C12Q 1/6883* | (2018.01) |
| *C12N 15/861* | (2006.01) |
| *A61K 38/50* | (2006.01) |
| *A61K 31/7088* | (2006.01) |
| *A61K 38/17* | (2006.01) |
| *G01N 33/573* | (2006.01) |
| *A61K 48/00* | (2006.01) |
| *C12N 7/00* | (2006.01) |
| *C12N 15/86* | (2006.01) |

(52) U.S. Cl.
CPC .......... *A61K 38/50* (2013.01); *A61K 31/7088* (2013.01); *A61K 38/1709* (2013.01); *A61K 48/0066* (2013.01); *C12N 7/00* (2013.01); *C12N 15/86* (2013.01); *C12Q 1/6883* (2013.01); *C12Y 305/00* (2013.01); *G01N 33/573* (2013.01); *C12N 2750/14143* (2013.01); *C12Q 2600/136* (2013.01); *C12Q 2600/158* (2013.01); *G01N 2333/914* (2013.01); *G01N 2440/36* (2013.01); *G01N 2800/325* (2013.01)

(58) Field of Classification Search
None
See application file for complete search history.

(56) References Cited

U.S. PATENT DOCUMENTS

| | | |
|---|---|---|
| 2009/0239940 A1 | 9/2009 | Del Monte et al. |
| 2014/0234287 A1 | 8/2014 | Hajjar et al. |
| 2015/0316551 A1 | 11/2015 | Hajjar et al. |

FOREIGN PATENT DOCUMENTS

| | | |
|---|---|---|
| WO | WO-01/25427 A1 | 4/2001 |
| WO | WO-2008/100376 A2 | 8/2008 |

OTHER PUBLICATIONS

Tanno et al entitiled "Emerging beneficial roles of sirtuins in heart failure" (Basic Res Cardiol 2012 107:273, pp. 1-14).*
Abstracts from the XXth World Congress of the International Society for Heart Research, May 13-16, 2010, Kyoto, Japan, J. Mol. Cell Cardiol., 48:S1-S185 (2010).
Adachi et al., S-Glutathiolation by peroxynitrite activates SERCA during arterial relaxation by nitric oxide, Nat. Med., 10(11):1200-7 (2004).
Asian et al., Proteomic detection of nitroproteins as potential biomarkers for cardiovascular disease, J. Proteomics, 74(11):2274-88 (2011).
Benson et al., SUMO modification regulates inactivation of the voltage-gated potassium channel Kv1.5, Proc. Natl. Acad. Sci. USA, 104(6):1805-10 (2007).
Byrne et al., Recirculating cardiac delivery of AAV2/1SERCA2a improves myocardial function in an experimental model of heart failure in large animals, Gene Ther., 15(23):1550-7 (2008).
Choudhary et al., Lysine acetylation targets protein complexes and co-regulates major cellular functions, Science, 325(5942):834-40 (2009).
Clarke et al., Functional consequences of glutamate, aspartate, and asparagine mutations in the stalk sector of the Ca2+-ATPase of sarcoplasmic reticulum, J. Biol. Chem., 264:11246-51 (1989).
Del Monte et al., Improvement in survival and cardiac metabolism after gene transfer of sarcoplasmic reticulum Ca(2+)-ATPase in a rat model of heart failure, Circulation, 104(12):1424-9 (2001).
Desterro et al., SUMO-1 modification of IkappaBalpha inhibits NF-kappaB activation, 2(2):233-9 (1998).
Dremina et al., Oxidation and inactivation of SERCA by selective reaction of cysteine residues with amino acid peroxides, Chem. Res. Toxicol., 20(10):1462-9 (2007).

(Continued)

*Primary Examiner* — Catherine S Hibbert
(74) *Attorney, Agent, or Firm* — Marshall, Gerstein & Borun LLP

(57) ABSTRACT

Methods for treating cardiovascular disease, and in particular heart failure, are provided comprising administering a therapeutically effective amount of a modulator of SERCA2a post-translation modification such as SUMOylation or acetylation. Also provided are methods of treating cardiovascular disease by inhibiting SERCA2a degradation. Further provided are methods of diagnosing a propensity to develop heart failure comprising determining if a SERCA2a mutant is present or determining the level of expression of SUMO1 in cardiomyocytes. The disclosure also provides methods of screening for therapeutics that modulate the post-translational modification of SERCA2a, such as by modulating post-translational SUMOylation and/or acetylation.

5 Claims, 16 Drawing Sheets

Specification includes a Sequence Listing.

(56) References Cited

OTHER PUBLICATIONS

French et al., Ischemia-reperfusion-induced calpain activation and SERCA2a degradation are attenuated by exercise training and calpain inhibition, Am. J. Physiol. Heart Circ. Physiol., 290(1):H128-36 (2006).
Gwathmey et al., Abnormal intracellular calcium handling in myocardium from patients with end-stage heart failure, Circ. Res., 61(1):70-6 (1987).
Gwathmey et al., Intracellular calcium related to force development in twitch contraction of mammalian myocardium, Cell Calcium, 11(8):531-8 (1990).
Hajjar et al., Adenoviral gene transfer of phospholamban in isolated rat cardiomyocytes. Rescue effects by concomitant gene transfer of sarcoplasmic reticulum Ca(2+)-ATPase, Circ. Res., 81(2):145-53 (1997).
Ihara et al., Overexpression of calreticulin sensitizes SERCA2a to oxidative stress, Biochem. Biophys. Res. Commun., 329(4):1343-9 (2005).
Jaski et al., Calcium upregulation by percutaneous administration of gene therapy in cardiac disease (CUPID Trial), a first-in-human phase 1/2 clinical trial, J. Card. Fail., 15(3):171-81 (2009).
Kawase et al., Reversal of cardiac dysfunction after long-term expression of SERCA2a by gene transfer in a pre-clinical model of heart failure, J. Am. Coll. Cardiol., 51(11):1112-9 (2008).
Kho et al., SUMO1-dependent modulation of SERCA2a in heart failure, Nature, 477(7366):601-5 (2011).
Kim et al., SUMOylation code in cancer development and metastasis, Mol. Cells, 22(3):247-53 (2006).
Kim et al., SUMOylation target sites at the C terminus protect Axin from ubiquitination and confer protein stability, FASEB J., 22(11):3785-94 (2008).
Knyushko et al., 3-Nitrotyrosine modification of SERCA2a in the aging heart: a distinct signature of the cellular redox environment, Biochem., 44(39):13071-81 (2005).
Lancel et al., Nitroxyl activates SERCA in cardiac myocytes via glutathiolation of cysteine 674, Circ. Res., 104(6):720-3 (2009).
Lancel et al., Oxidative posttranslational modifications mediate decreased SERCA activity and myocyte dysfunction in Galphaq-overexpressing mice, Circ. Res., 107(2):228-32 (2010).
Lytton et al., Molecular cloning of cDNAs from human kidney coding for two alternatively spliced products of the cardiac Ca2+-ATPase gene, J. Biol. Chem., 263(29):15024-31 (1988).
MacLennan et al., Phospholamban: a crucial regulator of cardiac contractility, Nat. Rev. Mol. Cell Biol., 4(7):566-77 (2003).
Meyer et al., Alterations of sarcoplasmic reticulum proteins in failing human dilated cardiomyopathy, Circulation, 92(4):778-84 (1995).
Minamisawa et al., Chronic phospholamban-sarcoplasmic reticulum calcium ATPase interaction is the critical calcium cycling defect in dilated cardiomyopathy, Cell, 99(3):313-22 (1999).
Mooney et al., Sumoylation of p68 and p72 RNA helicases affects protein stability and transactivation potential, Biochem., 49(1):1-10 (2010).
Perrino et al., Intermittent pressure overload triggers hypertrophy-independent cardiac dysfunction and vascular rarefaction, J. Clin. Invest., 116(6):1547-60 (2006).
Ryu et al., Hypothalamic neurodegeneration and adult-onset obesity in mice lacking the Ubb polyubiquitin gene, Proc. Natl. Acad. Sci. USA, 105(10): 4016-21 (2008).
Sampson et al., The small ubiquitin-like modifier-1 (SUMO-1) consensus sequence mediates Ubc9 binding and is essential for SUMO-1 modification, J. Biol. Chem., 276(24):21664-9 (2001).
Sarge et al., Sumoylation and human disease pathogenesis, Trends Biochem. Sci., 3494):200-5 (2009).
Schillinger et al., Relevance of Na+—Ca2+ exchange in heart failure, Cardiovasc. Res., 57(4):921-33 (2003).
Seth et al., Sarco(endo)plasmic reticulum Ca2+ ATPase (SERCA) gene silencing and remodeling of the Ca2+ signaling mechanism in cardiac myocytes, Proc. Natl. Acad. Sci. USA, 101(47):16683-8 (2004).
Shishido et al., Effects of MEK5/ERK5 association on small ubiquitin-related modification of ERK5: implications for diabetic ventricular dysfunction after myocardial infarction, Circ. Res., 102(11):1416-25 (2008).
Steffan et al., SUMO modification of Huntingtin and Huntington's disease pathology, Science, 304(5667):100-4 (2004).
Studer et al., Gene expression of the cardiac Na(+)—Ca2+ exchanger in end-stage human heart failure, Circ. Res., 75(3):445-53 (1994).
Sulaiman et al., Resveratrol, an activator of SIRT1, upregulates sarcoplasmic calcium ATPase and improves cardiac function in diabetic cardiomyopathy, Am. J. Physiol. Heart Circ. Physiol., 298(3):H833-43 (2010).
Van Rechem et al., Differential regulation of HIC1 target genes by CtBP and NuRD, via an acetylation/SUMOylation switch, in quiescent versus proliferating cells, Mol. Cell Biol., 30(16):4045-59 (2010).
Vandecaetsbeek et al., Factors controlling the activity of the SERCA2a pump in the normal and failing heart, Biofactors, 35(6):484-99 (2009).
Vangheluwe et al., Improving cardiac $Ca^{+2}$ transport into the sarcoplasmic reticulum in heart failure: lessons from the ubiquitous SERCA2b $Ca^{+2}$ pump, Biochem. Soc. Trans., 39(3):781-7 (2011).
Vangheluwe et al., Modulating sarco(endo)plasmic reticulum Ca 2+ATPase 2 (SERCA2) activity: cell biological implications, Cell Calcium, 38(3-4):291-302 (2005).
Wang et al., Regulation of cardiac specific nkx2.5 gene activity by small ubiquitin-like modifier, J. Biol. Chem., 283(34):23235-43 (2008).
Wang et al., SUMO-1 modification activated GATA4-dependent cardiogenic gene activity, J. Biol. Chem., 279(47):49091-8 (2004).
Welchman et al., Ubiquitin and ubiquitin-like proteins as multifunctional signals, Nat. Rev. Mol. Cell Biol., 6(8):599-609 (2005).
Woo et al., SUMO—a post-translational modification with therapeutic potential?, Curr. Opin. Pharmacol., 10(2):146-55 (2010).
Ying et al., Cysteine-674 oxidation and degradation of sarcoplasmic reticulum Ca(2+) ATPase in diabetic pig aorta, Free Radic. Biol. Med., 45(6):756-62 (2008).
Zarain-Herzberg et al., Decreased expression of cardiac sarcoplasmic reticulum Ca(2+)-pump ATPase in congestive heart failure due to myocardial infarction, Mol. Cell Biochem., 163-4:285-90 (1996).
Zhang et al., Sumoylation regulates lamin A function and is lost in lamin A mutants associated with familial cardiomyopathies, J. Cell Biol., 182(1):35-9 (2008).
Zhu et al., Protein pI shifts due to posttranslational modifications in the separation and characterization of proteins, Anal. Chem., 77(9):2745-55 (2005).
Lee et al., Proteomic profiling of SERCA2a overexpression in mitral valve regurgitation-induced swine model of heart failure, Abstracts from the World Congress of the International Society for Heart Research, May 13-16, 2010, Kyoto, Japan, J. Mol. Cell Cardiol., 48:S1-S185 (2010).

* cited by examiner

FIGURE 8

Amino acid sequence alignment

```
Human    MENAHTKTVEEVLGHFGVNESTGLSLEQVKKLKERWGSNELPAEEGKTLLELVIEQFEDL 60
Pig      MENAHTKTVEEVLGHFGVNESTGLSLEQVKKLKERWGSNELPAEEGKTLLELVIEQFEDL 60
Rat      MENAHTKTVEEVLGHFGVNESTGLSLEQVKKLKERWGSNELPAEEGKTLLELVIEQFEDL 60
Mouse    MENAHTKTVEEVLGHFGVNESTGLSLEQVKKLKERWGSNELPAEEGKTLLELVIEQFEDL 60
         ************************************************************

Human    LVRILLLAACISFVLAWFEEGEETITAFVEPFVILLILVANAIVGVWQERNAENAIEALK 120
Pig      LVRILLLAACISFVLAWFEEGEETITAFVEPFVILLILVANAIVGVWQERNAENAIEALK 120
Rat      LVRILLLAACISFVLAWFEEGEETITAFVEPFVILLILVANAIVGVWQERNAENAIEALK 120
Mouse    LVRILLLAACISFVLAWFEEGEETITAFVEPFVILLILVANAIVGVWQERNAENAIEALK 120
         ************************************************************

Human    EYEPEMGKVYRQDRKSVQRIKAKDIVPGDIVEIAVGDKVPADIRLTSIKSTTLRVDQSIL 180
Pig      EYEPEMGKVYRQDRKSVQRIKAKDIVPGDIVEIAVGDKVPADIRLTSIKSTTLRVDQSIL 180
Rat      EYEPEMGKVYRQDRKSVQRIKAKDIVPGDIVEIAVGDKVPADIRLTSIKSTTLRVDQSIL 180
Mouse    EYEPEMGKVYRQDRKSVQRIKAKDIVPGDIVEIAVGDKVPADIRLTSIKSTTLRVDQSIL 180
         ************************************************************

Human    TGESVSVIKHTDPVPDPRAVNQDKKNMLFSGTNIAAGKAMGVVVATGVNTEIGKIRDEMV 240
Pig      TGESVSVIKHTDPVPDPRAVNQDKKNMLFSGTNIAAGKAMGVVVATGVNTEIGKIRDEMV 240
Rat      TGESVSVIKHTDPVPDPRAVNQDKKNMLFSGTNIAAGKAMGVVVATGVNTEIGKIRDEMV 240
Mouse    TGESVSVIKHTDPVPDPRAVNQDKKNMLFSGTNIAAGKAMGVVVATGVNTEIGKIRDEMV 240
         ************************************************************

Human    ATEQERTPLQQKLDEFGEQLSKVISLICIAVWIINIGHFNDPVHGGSWIRGAIYYFKIAV 300
Pig      ATEQERTPLQQKLDEFGEQLSKVISLICIAVWIINIGHFNDPVHGGSWIRGAIYYFKIAV 300
Rat      ATEQERTPLQQKLDEFGEQLSKVISLICIAVWIINIGHFNDPVHGGSWIRGAIYYFKIAV 300
Mouse    ATEQERTPLQQKLDEFGEQLSKVISLICIAVWIINIGHFNDPVHGGSWIRGAIYYFKIAV 300
         ************************************************************

Human    ALAVAAIPEGLPAVITTCLALGTRRMAKKNAIVRSLPSVETLGCTSVICSDKTGTLTTNQ 360
Pig      ALAVAAIPEGLPAVITTCLALGTRRMAKKNAIVRSLPSVETLGCTSVICSDKTGTLTTNQ 360
Rat      ALAVAAIPEGLPAVITTCLALGTRRMAKKNAIVRSLPSVETLGCTSVICSDKTGTLTTNQ 360
Mouse    ALAVAAIPEGLPAVITTCLALGTRRMAKKNAIVRSLPSVETLGCTSVICSDKTGTLTTNQ 360
         ************************************************************

Human    MSVCRMFILDRVEGDTCSLNEFTITGSTYAPIGEVHKDDKPVNCHQYDGLVELATICALC 420
Pig      MSVCRMFILDKVEGDTCSLNEFTITGSTYAPIGEVHKDDKPVKCHQYDGLVELATICALC 420
Rat      MSVCRMFILDKVEGDTCSLNEFTITGSTYAPIGEVQKDDKPVKCHQYDGLVELATICALC 420
Mouse    MSVCRMFILDKVEGDTCSLNEFSITGSTYAPIGEVQKDDKPVKCHQYDGLVELATICALC 420
         **********:***********:***********:*****:*******************

Human    NDSALDYNEAKGVYEKVGEATETALTCLVEKMNVFDTELKGLSKIERANACNSVIKQLMK 480
Pig      NDSALDYNEAKGVYEKVGEATETALTCLVEKMNVFDTELKGLSKIERANACNSVIKQLMK 480
Rat      NDSALDYNEAKGVYEKVGEATETALTCLVEKMNVFDTELKGLSKIERANACNSVIKQLMK 480
Mouse    NDSALDYNEAKGVYEKVGEATETALTCLVEKMNVFDTELKGLSKIERANACNSVIKQLMK 480
         ************************************************************

Human    KEFTLEFSRDRKSMSVYCTPNKPSRTSMSKMFVKGAPEGVIDRCTHIRVGSTKVPMTSGV 540
Pig      KEFTLEFSRDRKSMSVYCTPNKPSRTSMSKMFVKGAPEGVIDRCTHIRVGSTKVPMTPGV 540
Rat      KEFTLEFSRDRKSMSVYCTPNKPSRTSMSKMFVKGAPEGVIDRCTHIRVGSTKVPMTPGV 540
Mouse    KEFTLEFSRDRKSMSVYCTPNKPSRTSMSKMFVKGAPEGVIDRCTHIRVGSTKVPMTPGV 540
         ********************************************************.**

Human    KQKIMSVIREWGSGSDTLRCLALATHDNPLRREEMHLEDSANFIKYETNLTFVGCVGMLD 600
Pig      KQKIMSVIREWGSGSDTLRCLALATHDNPMRREEMNLEDSANFIKYETNLTFVGCVGMLD 600
Rat      KQKIMSVIREWGSGSDTLRCLALATHDNPLRREEMHLEDSANFIKYETNLTFVGCVGMLD 600
Mouse    KQKIMSVIREWGSGSDTLRCLALATHDNPLKREEMHLEDSANFIKYETNLTFVGCVGMLD 600
         *****************************::****:************************

Human    PPRIEVASSVKLCRQAGIRVIMITGDNKGTAVAICRRIGIFGQDEDVTSKAFTGREFDEL 660
Pig      PPRIEVASSVKLCRQAGIRVIMITGDNKGTAVAICRRIGIFGQDEDVTSKAFTGREFDEL 660
Rat      PPRIEVASSVKLCRQAGIRVIMITGDNKGTAVAICRRIGIFGQDEDVTSKAFTGREFDEL 660
Mouse    PPRIEVASSVKLCRQAGIRVIMITGDNKGTAVAICRRIGIFGQDEDVTSKAFTGREFDEL 660
         ************************************************************

Human    NPSAQRDACLNARCFARVEPSHKSKIVEFLQSFDEITAMTGDGVNDAPALKKAEIGIAMG 720
Pig      NPSAQREACLNARCFARVEPSHKSKIVEFLQSFDEITAMTGDGVNDAPALKKSEIGIAMG 720
Rat      SPSAQRDACLNARCFARVEPSHKSKIVEFLQSFDEITAMTGDGVNDAPALKKSEIGIAMG 720
Mouse    SPSAQRDACLNARCFARVEPSHKSKIVEFLQSFDEITAMTGDGVNDAPALKKSEIGIAMG 720
         .*****:*********************************************:*******
```

FIGURE 8 (CONT)

```
Human   SGTAVAKTASEMVLADDNFSTIVAAVEEGRAIYNNMKQFIRYLISSNVGEVVCIFLTAAL 780
Pig     SGTAVAKTASEMVLADDNFSTIVAAVEEGRAIYNNMKQFIRYLISSNVGEVVCIFLTAAL 780
Rat     SGTAVAKTASEMVLADDNFSTIVAAVEEGRAIYNNMKQFIRYLISSNVGEVVCIFLTAAL 780
Mouse   SGTAVAKTASEMVLADDNFSTIVAAVEEGRAIYNNMKQFIRYLISSNVGEVVCIFLTAAL 780
        ************************************************************

Human   GFPEALIPVQLLWVNLVTDGLPATALGFNPPDLDIMNKPPRNPKEPLISGWLFFRYLAIG 840
Pig     GFPEALIPVQLLWVNLVTDGLPATALGFNPPDLDIMNKPPRNPKEPLISGWLFFRYLAIG 840
Rat     GFPEALIPVQLLWVNLVTDGLPATALGFNPPDLDIMNKPPRNPKEPLISGWLFFRYLAIG 840
Mouse   GFPEALIPVQLLWVNLVTDGLPATALGFNPPDLDIMNKPPRNPKEPLISGWLFFRYLAIG 840
        ************************************************************

Human   CYVGAATVGAAAWWFIAADGGPRVSFYQLSHFLQCKEDNPDFEGVDCAIFESPYPMTMAL 900
Pig     CYVGAATVGAAAWWFIAADGGPRVTFYQLSHFLQCKEDNPDFEGVDCAVFESPYPMTMAL 900
Rat     CYVGAATVGAAAWWFIAADGGPRVSFYQLSHFLQCKEDNPDFEGVDCAIFESPYPMTMAL 900
Mouse   CYVGAATVGAAAWWFIAADGGPRVSFYQLSHFLQCKEDNPDFDGVDCAIFESPYPMTMAL 900
        ************************:*********************:*****:***********

Human   SVLVTIEMCNALNSLSENQSLLRMPPWENIWLVGSICLSMSLHFLILYVEPLPLIFQITP 960
Pig     SVLVTIEMCNALNSLSENQSLLRMPPWENIWLVGSICLSMSLHFLILYVEPLPLIFQITP 960
Rat     SVLVTIEMCNALNSLSENQSLLRMPPWENIWLVGSICLSMSLHFLILYVEPLPLIFQITP 960
Mouse   SVLVTIEMCNALNSLSENQSLLRMPPWENIWLVGSICLSMSLHFLILYVEPLPLIFQITP 960
        ************************************************************

Human   LNVTQWLMVLKISLPVILMDETLKFVARNYLEP-AILE 997   (SEQ ID NO: 2)
Pig     LNLTQWLMVLKISLPVILMDETLKFVARNYLEP-AILE 997   (SEQ ID NO: 4)
Rat     LNLTQWLMVLKISLPVILMDETLKFVARNYLEP-AILE 997   (SEQ ID NO: 6)
Mouse   LNLTQWLMVLKISLPVILMDETLKFVARNYLEQPAILE 998   (SEQ ID NO: 8)
        **:*****************************    ****
```

FIGURE 9

DNA sequence alignments

```
Rat      ATGGAGAACGCTCACACAAAGACCGTGGAGGAGGTGCTGGGCCACTTCGGCGTCAACGAG 60
Mouse    ATGGAGAACGCTCACACAAAGACCGTGGAGGAGGTGCTGGGCCACTTCGGGGTCAACGAG 60
Human    ATGGAGAACGCGCACACCAAGACGGTGGAGGAGGTGCTGGGCCACTTCGGCGTCAACGAG 60
Pig      ATGGAGAACGCGCACACAAAGACGGTGGAGGAGGTGCTGGGCCACTTCGGCGTCAACGAG 60
         ********** ***** ***** **************************** ********

Rat      AGCACGGGGCTGAGCCTGGAGCAGGTCAAGAAGCTCAAGGAGAGATGGGGCTCCAACGAA 120
Mouse    AGCACGGGGCTGAGCCTTGGAGCAGGTCAAGAAGCTCAAGGAGAGATGGGGCTCCAACGAA 120
Human    AGTACGGGGCTGAGCCTGGAACAGGTCAAGAAGCTTAAGGAGAGATGGGGCTCCAACGAG 120
Pig      AGCACGGGGCTGAGCCTGGAGCAGGTCAAGAAGCTCAAGGAGAGATGGGGCTCCAACGAG 120
         ** ************* **** ************* *********************

Rat      TTGCCGGCTGAAGAAGGAAAGACCTTGCTGGAACTTGTGATCGAGCAGTTTGAAGACTTA 180
Mouse    TTGCCGGCTGAAGAAGGAAAAACCTTGCTGGAACTTGTGATTGAGCAGTTTGAAGACTTA 180
Human    TTACCGGCTGAAGAAGGAAAAACCTTGCTGGAACTTGTGATTGAGCAGTTTGAAGACTTG 180
Pig      TTACCGGCTGAAGAAGGGAAAACCTTGCTGGAACTTGTGATTGAGCAGTTTGAAGACTTA 180
         ** ************** **  ****************** ****************

Rat      CTAGTTAGAATTTTATTGCTGGCAGCATGTATATCTTTCGTTTTGGCTTGGTTCGAAGAA 240
Mouse    CTAGTTAGAATTTTACTGCTGGCAGCATGTATATCTTTCGTTTTGGCTTGGTTCGAGGAA 240
Human    CTAGTTAGGATTTTATTACTGGCAGCATGTATATCTTTTGTTTTGGCTTGGTTTGAAGAA 240
Pig      CTCGTTAGAATTTTATTGTTGGCAGCATGTATATCTTTTGTTTTGGCTTGGTTTGAAGAA 240
         ** ***** ****** *  ****************** *************** ** ***

Rat      GGTGAAGAAACGATTACAGCCTTTGTAGAACCTTTTGTAATTCTGCTTATATTGGTAGCC 300
Mouse    GGGGAAGAAACGATTACAGCCTTTGTAGAGCCGTTTGTAATTCTGCTTATCTTGGTAGCC 300
Human    GGTGAAGAAACAATTACAGCCTTTGTAGAACCTTTTGTAATTTTACTCATATTAGTAGCC 300
Pig      GGCGAAGAACAATTACAGCCTTTGTAGAACCCTTTGTAATTTTACTTATATTAGTAGCC 300
         ** ******** ****************** ** ********* * ** ** ******

Rat      AATGCAATTGTGGGTGTATGGCAGGAGAGAAACGCTGAAAATGCAATAGAAGCTCTTAAG 360
Mouse    AATGCAATCGTGGGTGTGTGCAGGAAAGAAATGCTGAAAATGCAATAGAAGCTCTTAAG 360
Human    AATGCAATTGTGGGTGTATGGCAGGAAAGAAATGCTGAAAATGCCATCGAAGCCCTTAAG 360
Pig      AATGCAATTGTGGGTGTATGGCAGGAAAGGAATGCAGAAAATGCCATCGAAGCCCTTAAG 360
         ********  ******* **  ****  ** **  **  ****** ** ***** ******

Rat      GAGTATGAACCTGAAATGGGCAAGGTGTATCGACAGGACAGAAAGAGTGTGCAGCGGATT 420
Mouse    GAATATGAGCCTGAAATGGGCAAAGTGTATCGACAGGACAGAAAGAGTGTGCAACGAATT 420
Human    GAATATGAGCCTGAAATGGGCAAAGTGTATCGACAGGACAGAAAGAGTGTGCAGCGGATT 420
Pig      GAGTATGAGCCTGAAATGGGCAAAGTGTATCGACAGGACAGGAAGAGTGTACAACGAATT 420
         ** ***** ************** ****************** ******** ** ** ***

Rat      AAAGCGAAAGATATAGTTCCTGGGGATATAGTGGAAATTGCTGTTGGTGACAAAGTTCCG 480
Mouse    AAAGCTAAAGACATAGTTCCTGGTGATATAGTGGAAATTGCTGTTGGTGACAAAGTTCCT 480
Human    AAAGCTAAAGACATAGTTCCTGGTGATATTGTAGAAATTGCTGTTGGTGACAAAGTTCCT 480
Pig      AAAGCTAAAGACATAGTTCCTGGTGATATTGTAGAAATTGCTGTTGGTGACAAAGTTCCT 480
         ***** ***** *********** ***** ** **************************

Rat      GCTGACATTAGATTGACATCCATCAAGTCTACAACTCTGAGAGTTGACCAGTCGATTCTT 540
Mouse    GCTGATATTAGATTGACATCCATCAAGTCTACAACTCTAAGAGTCGACCAGTCAATTCTT 540
Human    GCTGATATAAGGTTAACTTCCATCAAATCTACCACACTAAGAGTTGACCAGTCAATTCTC 540
Pig      GCTGATATAAGATTAACGTCCATCAAATCTACTACTCTAAGAGTTGACCAGTCAATTCTC 540
         ***** ** ** ** ** ******** ***** ** ** ***** ******** *****

Rat      ACAGGTGAATCTGTCTCGGTCATCAAGCATACTGACCCTGTCCCTGACCCACGAGCTGTT 600
Mouse    ACAGGTGAATCTGTCTCCGTCATCAAGCATACTGACCCTGTCCCTGACCCCCGAGCTGTT 600
Human    ACAGGTGAATCTGTCTCTGTCATCAAGCACACTGATCCCGTCCCTGACCCACGAGCTGTC 600
Pig      ACAGGTGAGTCTGTCTCTGTCATCAAGCACACCGACCCTGTCCCTGACCCACGGGCTGTC 600
         ********  *******  ********* ** ** ** ************ ** *****

Rat      AATCAAGACAAAAAGAACATGCTCTTTTCTGGCACAAACATCGCTGCTGGCAAAGCTATG 660
Mouse    AATCAAGACAAAAAGAACATGCTCTTTTCTGGTACAAACATTGCTGCTGGGAAAGCTATG 660
Human    AACCAAGATAAAAAGAACATGCTGTTTTCTGGTACAAACATTGCTGCTGGGAAAGCTATG 660
Pig      AACCAAGATAAGAAGAACATGCTCTTTTCTGGTACAAACATAGCAGCTGGCAAAGCCATG 660
         ** ***** ** *********** ******** ******** ** ***** ***** ***

Rat      GGAGTGGTGGTGGCGACTGGAGTCAATACTGAGATCGGCAAGATCCGGGATGAAATGGTT 720
Mouse    GGAGTGGTGGTGGCAACTGGAGTTAATACTGAGATCGGCAAGATCCGGGATGAAATGGTG 720
Human    GGAGTGGTGGTAGCAACTGGAGTTAACACCGAAATTGGCAAGATCCGGGATGAAATGGTG 720
Pig      GGAGTGGTGGTGGCAACTGGAGTTAACACTGAAATTGGCAAGATCCGGGATGAAATGGTA 720
         *********** ** ******** ** ** ** ** ************************
```

FIGURE 9 (cont)

```
Rat    GCAACAGAACAGGAGAGAACACCCCTACAGCAGAAGCTGGACGAGTTTGGGGAACAGCTT 780
Mouse  GCAACAGAACAGGAGAGAACACCCCTACAGCAGAAGCTAGACGAGTTTGGGGAGCAGCTT 780
Human  GCAACAGAACAGGAGAGAACACCCCTTCAGCAAAAACTAGATGAATTTGGGGAACAGCTT 780
Pig    GCAACGGAACAGGAGAGAACACCCCTCCAGCAGAAACTAGATGAGTTTGGGGAACAGCTT 780
       ***** *************** ***** ** ** ** ** ******** ******

Rat    TCCAAAGTTATCTCCCTCATTTGCATTGCAGTCTGGATCATCAACATCGGGCATTTCAAT 840
Mouse  TCCAAAGTTATCTCCCTCATTTGCATTGCAGTCTGGATCATCAACATTGGGCATTTCAAT 840
Human  TCCAAAGTCATCTCCCTTATTTGCATTGCAGTCTGGATCATAAATATTGGGCACTTCAAT 840
Pig    TCCAAAGTCATCTCCCTTATTTGCATTGCAGTCTGGATCATAAACATTGGGCACTTCAAT 840
       ******** ******* ******************** ** ** ***** ******

Rat    GACCCAGTTCATGGTGGCTCTTGGATCAGAGGTGCCATCTACTACTTTAAGATTGCAGTG 900
Mouse  GACCCAGTTCATGGTGGCTCCTGGATCAGGGGTGCCATCTACTACTTTAAGATTGCCGTG 900
Human  GACCCGGTTCATGGAGGGTCCTGGATCAGAGGTGCTATTTACTACTTTAAAATTGCAGTG 900
Pig    GACCCGGTTCATGGAGGCTCCTGGATCAGAGGTGCTATTTATTACTTTAAAATTGCAGTG 900
       ***** ******** ** ** ******** ***** ** ** ******** ***** ***

Rat    GCCCTGGCTGTTGCTGCCATCCCTGAGGGTCTGCCTGCTGTCATCACCACCTGCTTGGCT 960
Mouse  GCCCTGGCTGTTGCCGCAATCCCTGAGGGTCTGCCTGCTGTCATCACCACCTGCTTAGCT 960
Human  GCCCTGGCTGTAGCAGCCATTCCTGAAGGTCTGCCTGCAGTCATCACCACCTGCCTGGCT 960
Pig    GCCCTGGCTGTAGCAGCCATTCCTGAAGGCCTGCCTGCTGTCATTACCACCTGCCTGGCT 960
       *********** ** ** ** ***** *** ******** ***** ********* * ***

Rat    CTTGGAACTCGAAGGATGGCAAAGAAAAATGCTATTGTTCGAAGTCTGCCTTCTGTGGAA 1020
Mouse  CTTGGAACTCGTAGGATGGCAAAGAAAAATGCTATCGTTCGAAGTCTGCCTTCTGTGGAG 1020
Human  CTTGGAACTCGCAGAATGGCAAAGAAAAATGCCATTGTTCGAAGCCTCCCGTCTGTGGAA 1020
Pig    CTTGGAACTCGTAGAATGGCAAAGAAAAATGCCATTGTTCGAAGTCTCCCCTTCTGTGGAA 1020
       *********** ** ****************** ** ******** ** ** ** ********

Rat    ACCCTTGGTTGTACTTCTGTTATCTGCTCAGACAAGACCGGCACACTTACCACAAACCAG 1080
Mouse  ACCCTTGGTTGTACTTCTGTTATCTGCTCAGATAAGACAGGCACACTTACCACAAACCAG 1080
Human  ACCCTTGGTTGTACTTCTGTTATCTGCTCAGACAAGACTGGTACACTTACAACAAACCAG 1080
Pig    ACCCTTGGTTGCACTTCCGTTATCTGCTCAGACAAGACTGGTACACTTACAACAAACCAG 1080
       *********** ***** ***************** ***** ** ******** *********

Rat    ATGTCCGTCTGCAGGATGTTCATTCTGGACAAAGTAGAAGGTGATACTTGTTCCCTTAAT 1140
Mouse  ATGTCCGTGTGCAGGATGTTCATTCTGGACAAAGTAGAAGGTGACACTTGTTCCCTTAAT 1140
Human  ATGTCAGTCTGCAGGATGTTCATTCTGGACAGAGTGGAAGGTGATACTTGTTCCCTTAAT 1140
Pig    ATGTCAGTCTGCAGGATGTTCATTCTGGACAAAGTTGAAGGTGATACTTGTTCCCTGAAT 1140
       ***** ** **************************** *** ******** ************ ***

Rat    GAGTTTACCATAACTGGATCAACCTATGCACCCATTGGAGAAGTGCAAAAAGATGACAAG 1200
Mouse  GAGTTCAGCATAACTGGATCCACATATGCACCAATTGGAGAAGTGCAAAAGGATGATAAG 1200
Human  GAGTTTACCATAACTGGATCAACTTATGCACCTATTGGAGAAGTGCATAAAGATGATAAG 1200
Pig    GAGTTTACCATAACTGGATCAACATATGCTCCTATTGGAGAAGTCCATAAAGATGATAAA 1200
       ***** * *********** ** ***** ** ************ ** ** ****** **

Rat    CCAGTGAAATGCCATCAGTATGACGGGCTTGTAGAGTTAGCAACGATCTGTGCTCTGTGT 1260
Mouse  CCAGTGAAGTGCCATCAGTATGACGGGCTTGTAGAGTTAGCCACCATCTGTGCTCTGTGT 1260
Human  CCAGTGAATTGTCACCAGTATGATGGTCTTGGTAGAATTAGCAACAATTTGTGCTCTTTGT 1260
Pig    CCAGTAAAGTGTCATCAATATGATGGTCTTGTGGAATTGGCAACAATTTGTGCTCTCTGT 1260
       ***** ** ** ** ** ***** ** ** ** ** ** ** ** ** ******** ***

Rat    AATGACTCTGCTTTGGATTACAATGAGGCGAAGGGTGTGTATGAAAAAGTTGGAGAAGCC 1320
Mouse  AATGACTCTGCTTTGGATTATAATGAGGCAAAGGGTGTGTATGAGAAAGTTGGAGAAGCT 1320
Human  AATGACTCTGCTTTGGATTACAATGAGGCAAAGGGTGTGTATGAAAAAGTTGGAGAAGCT 1320
Pig    AATGACTCTGCTTTGGATTACAATGAGGCAAAGGGTGTGTATGAAAAAGTTGGAGAAGCT 1320
       ******************** ******** ***************** ************

Rat    ACAGAGACTGCTCTCACGTGCCTGGTAGAGAAGATGAATGTATTCGACACGGAGCTGAAG 1380
Mouse  ACCGAGACTGCTCTCACGTGCCTGGTGGAGAAGATGAATGTATTTGATACTGAGCTGAAG 1380
Human  ACAGAGACTGCTCTCACTTGCCTAGTAGAGAAGATGAATGTATTTGATACCGAATTGAAG 1380
Pig    ACAGAGACTGCTCTCACTTGCCTGGTAGAGAAGATGAATGTCTTTGATACTGAGTTAAAG 1380
       ** ************** ***** ** ************** ** ** ** ** * ***

Rat    GGACTTTCTAAAATAGAACGCGCCAACGCCTGCAACTCGGTCATAAAACAGCTCATGAAG 1440
Mouse  GGGCTTTCTAAAATAGAGCGTGCAAACGCCTGCAACTCAGTCATAAAACAGCTGATGAAG 1440
Human  GGTCTTTCTAAAATAGAACGTGCAAATGCCTGCAACTCAGTCATTAAACAGCTGATGAAA 1440
Pig    GGTCTTTCTAAAATAGAACGAGCAAATGCCTGCAACTCGGTCATTAAACAATTGATGAAA 1440
       ** ************** ** ** ** ********** ***** *  * ** *****

Rat    AAGGAATTCACGCTAGAGTTTTCACGTGATAGAAATCAATGTCCGTCTACTGTACACCA 1500
Mouse  AAGGAGTTCACTCTGGAGTTTTCACGGGATAGAAATCAATGTCCGTCTATTGTACCCCA 1500
Human  AAGGAATTCACTCTAGAGTTTTCACGTGACAAAAGTCAATGTCCGGTTTACTGTACACCA 1500
Pig    AAGGAATTTACTCTAGAGTTTTCACGTGATAGAAATCAATGTCAGTTTATTGTACACCA 1500
       ***** ** ** ** ** *********** ** ***** ********* ** ** ***** ***
```

FIGURE 9 (cont)

```
Rat     AACAAACCGAGCCGGACGTCCATGAGCAAGATGTTTGTGAAGGGTGCTCCAGAAGGTGTC 1560
Mouse   AACAAGCCAAGCCGGACATCCATGAGCAAGATGTTTGTGAAGGGGGCTCCAGAAGGTGTC 1560
Human   AATAAACCAAGCAGGACATCAATGAGCAAGATGTTTGTGAAGGGTGCTCCTGAAGGTGTC 1560
Pig     AACAAACCAAGCCGGACATCGATGAGCAAATGTTTGTGAAGGGTGCTCCCGAAGGTGTC 1560
        ** ** ** *** **** ** ******** *************** ***** *********

Rat     ATCGACAGGTGCACCCACATCCGAGTTGGAAGTACCAAGGTCCCCATGACGCCTGGTGTT 1620
Mouse   ATCGATAGGTGCACCCACATCCGAGTTGGAAGTACCAAGGTCCCCATGACTCCTGGTGTC 1620
Human   ATTGACAGGTGCACCCACATTCGAGTTGGAAGTACTAAGGTTCCTATGACCTCTGGAGTC 1620
Pig     ATTGACAGGTGTACCCACATTCGAGTTGGAAGTACTAAAGTCCCCATGACTCCTGGCGTC 1620
        ** ** ***** ******** ************** ** ** ** ***** **** **

Rat     AAACAGAAGATTATGTCTGTCATTCGGGAGTGGGGCAGTGGCAGCGACACACTGCGGTGC 1680
Mouse   AAACAGAAGATTATGTCTGTCATTCGGGAGTGGGGCAGTGGCAGCGACACGCTACGGTGC 1680
Human   AAACAGAAGATCATGTCTGTCATTCGAGAGTGGGGTAGTGGCAGCGACACACTGCGATGC 1680
Pig     AAACAGAAGATCATGTCTGTCATTCGGGAATGGGCAGTGGCAGCGACACACTGCGATGC 1680
        *********** *************** ** ***** ************* ** ** ***

Rat     CTGGCTCTGGCCACTCATGACAACCCGCTGAGGAGAGAGGAGATGCACCTGGAAGATTCT 1740
Mouse   CTGGCTCTGGCCACTCATGACAACCACTGAAGAGAGAGGAGATGCACCTGGAAGACTCT 1740
Human   CTGGCCCTGGCCACTCATGACAACCCACTGAGAAGAGAAGAAATGCACCTTGAGGACTCT 1740
Pig     CTGGCTCTGGCCACTCATGACAACCCGATGAGAAGAGAAGAAATGAACCTTGAGGATTCT 1740
        ***** ******************** *** ****** ** *** **** ** ** ***

Rat     GCGAACTTCATCAAATATGAGACCAATCTGACTTTCGTTGGCTGTGTGGGCATGCTGGAC 1800
Mouse   GCTAACTTCATCAAATACGAGACCAACCTGACTTTCGTCGGCTGTGTGGGCATGCTGGAT 1800
Human   GCCAACTTTATTAAATATGACACCAATCTGACCTTCGTTGGCTGCGTGGGCATGCTGGAT 1800
Pig     GCCAACTTTATTAAATACGAGACCAATCTGACTTTCGTTGGCTGTGTGGGCATGCTGGAC 1800
        ** ***** ** ***** ******** ***** ***** ***** ***************

Rat     CCTCCCAGGATTGAAGTGGCCTCTTCTGTGAAGCTGTGCCGGCAAGCGGGCATCCGAGTC 1860
Mouse   CCTCCCAGGATTGAAGTAGCCTCTTCTGTGAAGCTGTGCCGGCAAGCAGGCATCCGGGTC 1860
Human   CCTCCCGAGAATCGAGGTGGCCTCCTCCGTGAAGCTGTGCCGGCAAGCAGGCATCCGGGTC 1860
Pig     CCTCCAAGAATCGAAGTGGCCTCCTCTGTGAAGCTGTGCCGGCAGGCAGGCATCCGGGTC 1860
        ***** ** ** ** ** ***** ** ******************* ** ******** ***

Rat     ATCATGATCACTGGGGATAACAAAGGCACTGCTGTGGCCATCTGTCGCCGCATTGGCATC 1920
Mouse   ATCATGATCACTGGAGACAACAAGGGCACCGTGTGGCCATCTGTCGCCGCATTGGCATC 1920
Human   ATCATGATCACTGGGGACAACAAGGGCACTGCTGTGGCCATCTGTCGCCGCATCGGCATC 1920
Pig     ATTATGATCACAGGCGACAACAAGGGTACCGCTGTGGCCATCTGCCGTCGCATTGGCATC 1920
        ** ******** ** ** ****** ** ** ************** ** ***** ******

Rat     TTTGGGCAGGATGAGGATGTGACATCAAAGGCTTTTACAGGGCGAGAATTTGATGAATTA 1980
Mouse   TTTGGGCAGGATGAGGATGTGACATCAAAGGCTTTTACAGGGCGAGAGTTTGATGAATTA 1980
Human   TTCGGGCAGGATGAGGATGTGACGTCAAAAGCTTTCACAGGCGGGAGTTTGATGAACTC 1980
Pig     TTTGGGCAGGACGAGGATGTGACGTCAAAGGCTTTTACAGGTCGGGAGTTTGATGAGCTC 1980
        ** ******** ***** ***** ***** ***** ***** ** ** ********  *

Rat     AGCCCCTCAGCCCAGAGAGACGCCTGCTTAAATGCCCGTTGTTTTGCTCGAGTTGAACCT 2040
Mouse   AGCCCTTCAGCCCAGAGAGATGCCTGCTTAAATGCCCGCTGTTTTGCTCGAGTTGAACCT 2040
Human   AACCCCTCCGCCCAGCGAGACGCCTGCCTGAACGCCCGCTGTTTTGCTCGAGTTGAACCC 2040
Pig     AATCCTTCAGCCCAGAGAGAAGCCTGCCTGAATGCCCGCTGTTTCGCTCGAGTTGAACCT 2040
        *  ** ** ******* **** ****** * ** ***** ***** **************

Rat     TCCCACAAGTCTAAGATCGTTGAGTTCCTGCAGTCCTTTGATGAGATCACAGCTATGACT 2100
Mouse   TCCCACAAGTCTAAGATTGTTGAGTTCCTTCAGTCCTTTGATGAGATCACAGCTATGACT 2100
Human   TCCCACAAGTCTAAAATCGTAGAATTTCTTCAGTCTTTTGATGAGATTACAGCTATGACT 2100
Pig     TCCCACAAGTCTAAAATTGTAGAATTTCTTCAGTCTTTTGATGAGATTACAGCTATGACT 2100
        ************** ** ** ** ** ** ***** ************ ***********

Rat     GGTGATGGTGTGAACGACGCGCCCGCTCTGAAGAAGTCGGAAATCGGGATTGCCATGGGC 2160
Mouse   GGTGATGGTGTGAATGATGCTCCTGCTCTGAAGAAATCTGAAATCGGGATTGCCATGGGC 2160
Human   GGCGATGGCGTGAACGATGCTCCTGCTCTGAAGAAAGCCGAGATTGGCATTGCCATGGGC 2160
Pig     GGGGACGGTGTGAATGATGCTCCTGCTCTGAAGAAGTCTGAGATCGGCATTGCCATGGGC 2160
        ** ** ** ****** ** ** ** ***********  * ** ** ** ***** ******

Rat     TCAGGGACTGCAGTGGCTAAGACGGCCTCTGAGATGGTGCTGGCCGACGACAACTTCTCC 2220
Mouse   TCAGGGACTGCAGTGGCTAAGACTGCTTCTGAGATGGTCCTGGCAGATGACAACTTCTCC 2220
Human   TCTGGCACTGCGGTGGCTAAAACCGCCTCTGAGATGGTCCTGGCGGATGACAACTTCTCC 2220
Pig     TCTGGCACCGCGGTGGCTAAAACTGCCTCCGAGATGGTCCTGGCTGATGACAACTTCTCC 2220
        ** ** ** ** ******** ** ** ** ******** ***** ** ************

Rat     ACCATCGTGGCCGCTGTTGAGGAGGGGCGCGCCATCTACAACAACATGAAGCAGTTCATC 2280
Mouse   ACCATTGTGGCTGCTGTTGAGGAGGGGCGAGCCATCTACAACAACATGAAGCAGTTCATC 2280
Human   ACCATTGTGGCTGCCGTTGAGGAGGGGCGGGCAATCTACAACAACATGAAACAGTTCATC 2280
Pig     ACCATTGTGGCTGCTGTGGAGGAGGGGACGGGCAATATACAACAACATGAAGCAGTTCATT 2280
        ***** ***** ** ** ******** ** ** *************** ********
```

FIGURE 9 (cont)

```
Rat     CGCTACCTCATCTCCTCCAACGTGGGGGAGGTGGTCTGTATCTTCCTGACGGCAGCCCTT 2340
Mouse   CGCTACCTCATCTCATCCAACGTGGGGGAAGTGGTCTGTATCTTCCTGACGGCAGCCCTT 2340
Human   CGCTACCTCATCTCGTCCAACGTCGGGGAAGTTGTCTGTATTTTCCTGACAGCAGCCCTT 2340
Pig     CGCTACCTCATCTCGTCCAACGTGGGAGAAGTTGTCTGTATTTTCCTGACAGCAGCCCTT 2340
        ************* ******* ** ** ** ******* ******** *********

Rat     GGGTTTCCTGAAGCTTTGATTCCTGTCCAGTTACTCTGGGTCAATCTGGTGACGGATGGT 2400
Mouse   GGGTTTCCTGAGGCTTTAATTCCTGTCCAGTTACTCTGGGTCAATCTGGTGACAGATGGT 2400
Human   GGATTTCCCGAGGCTTTGATTCCTGTTCAGCTGCTCTGGGTCAATCTGGTGACAGATGGC 2400
Pig     GGATTTCCTGAGGCTTTAATTCCTGTCCAGCTGCTCTGGGTCAATCTGGTGACAGATGGC 2400
        ** ***** ** ***** ******** *** * ******************* *****

Rat     CTGCCTGCCACTGCGCTGGGGTTCAATCCTCCAGATCTGGACATCATGAACAAACCCCCA 2460
Mouse   CTGCCTGCCACTGCGCTGGGGTTCAATCCTCCAGACCTGGACATCATGAACAAACCCCCC 2460
Human   CTGCCTGCCACTGCACTGGGGTTCAACCCTCCTGATCTGGACATCATGAATAAACCTCCC 2460
Pig     CTGCCTGCCACTGCACTGGGGTTCAATCCTCCTGATCATTATGACAAACCACCC 2460
        ************** ************ ***** ** ******** ***** ***** **

Rat     CGGAACCCAAAAGAACCGCTGATCAGCGGGTGGCTCTTTTTCCGTTACCTGGCTATTGGC 2520
Mouse   CGGAACCCAAAAGAACCACTGATCAGCGGGTGGCTCTTTTTCCGTTACCTGGCTATTGGC 2520
Human   CGGAACCCAAAGGAACCATTGATCAGCGGGTGGCTCTTTTTCCGTTACTTGGCTATTGGC 2520
Pig     CGGAACCCAAAGGAACCACTGATCAGTGGGTGGCTCTTTTTCCGCTACCTGGCTATTGGC 2520
        *********** ***** ******* ****************** *** **********

Rat     TGTTATGTTGGCGCTGCCACCGTGGGTGCTGCTGCGTGGTGGTTCATCGCTGCTGACGGT 2580
Mouse   TGTTATGTTGGCGCTGCCACCGTGGGTGCTGCTGCATGGTGGTTCATCGCTGCTGACGGC 2580
Human   TGTTACGTCGGCGCTGCTACCGTGGGTGCTGCTGCATGGTGGTTCATTGCTGCTGACGGT 2580
Pig     TGTTACGTTGGTGCTGCTACTGTGGGTGCTGCTGCGTGGTGGTTCATTGCTGCCGATGGT 2580
        ***** ** ** ***** ** ************* ************ ***** ** **

Rat     GGTCCGAGAGTCTCCTTCTACCAGCTGAGTCATTTCCTGCAGTGTAAGGAGGACAACCCA 2640
Mouse   GGTCCAAGAGTCTCCTTCTACCAGCTGAGTCATTTCCTACAGTGTAAGGAGGACAACCCA 2640
Human   GGTCCAAGAGTGTCCTTCTACCAGCTGAGTCATTTCCTACAGTGTAAAGAGGACAACCCG 2640
Pig     GGTCCGAGAGTGACCTTCTACCAGCTGAGTCATTTCCTACAGTGTAAAGAGGACAACCCA 2640
        ***** *****   ******************* ******* ***** ******* ***** ***

Rat     GACTTCGAAGGAGTGGATTGTGCAATCTTTGAGTCCCCGTATCCGATGACAATGGCACTT 2700
Mouse   GACTTCGATGGAGTGGATTGTGCAATCTTTGAGTCCCCATATCCCAATGACAATGGCACTT 2700
Human   GACTTTGAAGGCGTGGATTGTGCAATCTTTGAATCCCCATACCCGATGACAATGGCGCTC 2700
Pig     GACTTTGAGGGAGTGGATTGTGCAGTCTTTGAATCCCCTTACCCAATGACAATGGCGCTG 2700
        ***** ** ** ************ ******* *****    ** ** *********** **

Rat     TCTGTTCTAGTCACCATAGAGATGTGCAATGCCCTCAACAGCTTGTCTGAAAACCAGTCC 2760
Mouse   TCTGTTCTAGTAACCATAGAGATGTGTAATGCCCTCAACAGCTTGTCCGAAAACCAGTCT 2760
Human   TCTGTTCTAGTAACTATAGAAATGTGTAACGCCCTCAACAGCTTGTCCGAAAACCAGTCC 2760
Pig     TCTGTTCTAGTCACCATAGAGATGTGTAACGCCCTCAACAGTTTGTCGGAAAACCAGTCC 2760
        *********** ** ***** ***** ** *********** ***** ************

Rat     CTGCTGAGGATGCCCCCCTGGGAGAACATCTGGCTCGTGGGCTCCATCTGCTTGTCCATG 2820
Mouse   TTGCTGAGGATGCCCCCCTGGGAGAATATCTGGCTCGTGGGCTCCATCTGCTTGTCCATG 2820
Human   TTGCTGAGGATGCCCCCCTGGGAGAACATCTGGCTCGTGGGCTCCATCTGCCTGTCCATG 2820
Pig     CTGCTAAGGATGCCACCCTTGGGAGAACATTTGGCTCGTGGGCTCCATCTGCCTGTCCATG 2820
        **** ******** **** ******* ** ******************** ********

Rat     TCCCTTCACTTCTTGATCCTCTACGTGGAACCTTTGCCACTCATTTTCCAGATCACACCG 2880
Mouse   TCACTTCACTTCTTGATCCTCTACGTGGAACCTTTGCCGCTCATTTTCCAGATCACACCG 2880
Human   TCACTCCACTTCCTGATCCTCTATGTCGAACCCTTGCCACTCATCTTCCAGATCACACCG 2880
Pig     TCACTCCACTTCCTAATCCTCTATGTGGAACCCTGCCACTTATCTTCCAGATCACACCG 2880
        ** ** ****** * ******** ** *****  **** ** ** *************

Rat     CTGAATCTGACCCAGTGGCTGATGGTGCTGAAAATCTCCCTGCCTGTGATCCTCATGGAC 2940
Mouse   CTGAATCTGACCCAGTGGCTGATGGTGCTGAAAATCTCCTTGCCTGTGATCCTCATGGAT 2940
Human   CTGAACGTGACCCAGTGGCTGATGGTGCTGAAAATCTCCTTGCCCGTGATTCTCATGGAT 2940
Pig     CTGAATTTGACCCAGTGGCTGATGGTGCTGAAAATCTCCTTGCCT   GTGATTCTAATGGAT 2940
        *****  ********************* ********** **** ***** ** *****

Rat     GAGACGCTCAAGTTTGTGGCCCGAAACTACCTGGAG---CCTGCAATACTGGAGTAA 2994  (SEQ ID NO: 5)
Mouse   GAGACGCTCAAGTTTGTGGCCCGAAACTACCTGGAACAACCCGCAATACTGGAGTAA 2997  (SEQ ID NO: 7)
Human   GAGACGCTCAAGTTTGTGGCCCGCAACTACCTGGAA---CCTGCAATACTGGAGTAA 2994  (SEQ ID NO: 1)
Pig     GAGACCCTCAAGTTTGTGGCCCGCAACTACCTGGAA---CCTGCAATACTGGAGTAA 2994  (SEQ ID NO: 3)
        ***** *************** ************     ** **************
```

SUMOYLATION OF SERCA2A AND CARDIOVASCULAR DISEASE

CROSS-REFERENCE TO RELATED APPLICATIONS

This application claims the priority benefit of provisional U.S. Patent Application No. 61/507,526 filed Jul. 13, 2011, which is incorporated herein by reference in its entirety.

FIELD

The disclosure relates generally to the prevention and treatment of cardiac disease and, more specifically, to the modulation of SERCA2a to prevent and/or treat cardiac disease or ameliorate a symptom thereof.

BACKGROUND

SERCA2a is a critical ATPase responsible for $Ca^{2+}$ re-uptake by cardiac muscle cells during excitation-contraction coupling. The down-regulation of SERCA2a is one of the primary abnormalities found in failing hearts. Consistent with this observation, restoration of SERCA2a by gene transfer has proven to be effective in normalizing cardiac function in humans as well as model animals.

Heart failure (HF) represents complex patho-physiological conditions that are often final consequences of various cardiovascular disorders including atherosclerosis, cardiomyopathy, and hypertension. The incidence of HF continues to grow worldwide. HF is characterized by contractile dysfunction that is in large part due to abnormalities in sarcoplasmic reticulum (SR) $Ca^{2+}$ cycling (Gwathmey et al., 1987; Gwathmey and Hajjar, 1990). In normal human cardiomyocytes, the activity of SERCA2a contributes to the removal of more than 70% of cytosolic $Ca^{2+}$ into the SR during diastole. SERCA2a, therefore, affects muscle contraction kinetics by determining the SR $Ca^{2+}$ content in the subsequent beat (MacLennan and Kranias, 2003). Impaired SR $Ca^{2+}$ uptake due to a decreased expression level and a reduced activity of SERCA2a has been reported in failing human hearts (Meyer et al., 1995; Minamisawa et al., 1999; Zarain-Herzberg et al., 1996). It is known that restoration of SERCA2a levels by gene transfer improves systolic and diastolic dysfunction in rodent (del Monte et al., 2001) and porcine models of HF (Byrne et al., 2008; Kawase et al., 2008).

Post-translational modification (PTM) is an important way to modulate the function of diverse cellular proteins by affecting their enzymatic activity, localization, stability, or turnover rates in response to environmental stimuli. It was previously shown that SERCA2a activity could be modulated by PTM such as glutathiolation (Adachi et al., 2004; Dremina et al., 2007; Lancel et al., 2009) and nitration (Knyushko et al., 2005). It is also known that the isoelectric point of SERCA2a becomes both more acidic and basic in the failing heart compared to the normal heart. In addition, restoration of SERCA2a levels by gene transfer also partially restored this shifted isoelectric point of SERCA2a in the failing heart (Figure S1). These data indicated that there existed multiple PTMs of SERCA2a, which are associated with the development of HF.

Small ubiquitin-related modifier (SUMO), which shares 18% sequence homology with ubiquitin, can be conjugated to lysine residues of target proteins. This PTM is referred to as SUMOylation. In humans, three SUMO isoforms (SUMO1-3) appear to modify both common and distinct substrates (Welchman et al., 2005). Specifically, SUMO1 has been shown to play important roles in modulating diverse cellular processes including transcriptional regulation, nuclear transport, DNA repair, cell cycle, plasma membrane depolarization, and signal transduction both in normal and pathogenic conditions (Sarge and Park-Sarge, 2009). SUMO-mediated regulation of cardiac transcriptional factors such as GATA4 (Wang et al., 2004) and Nkx2.5 (Wang et al., 2008) is associated with differentiation of cardiomyocytes and development of cardiac structures. SUMO-mediated modification also regulates cardiac ion channel activity including voltage-gated potassium channels (Benson et al., 2007). In addition, SUMOylation of ERK5 has recently been linked to diabetes-related heart conditions (Shishido et al., 2008).

Over the past few years, a host of studies has shown that SUMOylation can regulate the activities of a variety of proteins both in normal and human pathogenesis, including neurodegenerative diseases, cancer, and familial dilated cardiomyopathy (Kim and Baek, 2006; Steffan et al., 2004; Zhang and Sarge, 2008). Recently, the critical role of SUMOylation of ERK5 in diabetic heart has been reported (Woo and Abe, 2010).

SUMOylation can affect biochemical properties of target proteins such as enzymatic activities and stabilities. The underlying molecular mechanism is largely unknown, but three possibilities have been suggested. SUMO attachment may alter interaction between the target and its binding partners (DNA or protein) by masking of existing binding sites or addition of interfaces that are present in SUMO. Alternatively, SUMOylation may induce a conformational change of the target proteins, which can either increase or decrease the enzymatic activities. Finally, SUMOylation can block other PTMs at lysine residues such as ubiquitination and acetylation, which lead to alterations in the functional properties of target proteins.

It has been shown that SERCA2a is a target of oxidative PTMs. Accumulated nitration of SERCA2a has been observed in skeletal muscle undergoing electrical stimulation, in hypercholesteremic aorta, and in ischemic human heart. The nitration at tyrosines 294 and 295 was correlated with the reduced $Ca^{2+-}$ ATPase activity of SERCA2a. The position of these tyrosines within a functionally key membrane region of SERCA2a and close to a negatively charged side chain would seem to ensure both efficient nitration and a mechanism for decreased rates of calcium transport. In addition, oxidation of a redox-sensitive cysteine residue of SERCA2a (cysteine 674) was detected in diabetic pigs (Ying et al., 2008). This oxidative modification may be related to the accelerated SERCA degradation in ischemic heart (French et al., 2006) and in H9c2 cells exposed to hydrogen peroxide Mara et al., 2005).

Accordingly, a need continues to exist in the art for therapeutics and methods of treating cardiovascular disease such as heart failure in a manner that is safe and effective for humans and other animals.

SUMMARY

The subject matter disclosed herein satisfies at least one of the aforementioned needs in the art for therapeutics and methods of treating cardiovascular disease. In particular, the experiments disclosed herein establish that SERCA2a is SUMOylated. The SUMO1 level and SUMOylation of SERCA2a was greatly reduced in failing hearts. SUMO1 overexpression restored impaired cardiac function in failing hearts partly through enhancing enzymatic activity and stability of SERCA2a, whereas SUMO1 down-regulation resulted in cardiac dysfunction. The data provide novel insight on the regulation of SERCA2a function by PTM and provide the basis for the design of novel therapeutic strategies for HF.

Various aspects of the disclosed subject matter are described in the following enumerated paragraphs.

1. A method of treating cardiac dysfunction in a subject comprising administering a therapeutically effective amount of a modulator of SERCA2a post-translational modification to the subject.

2. The method according to paragraph 1 wherein the cardiac dysfunction is selected from the group consisting of heart failure, pressure overload-induced cardiac dysfunction, and cardiac dysfunction induced by inhibited calcium decay.

3. The method according to paragraph 2 wherein the heart failure comprises contractile dysfunction.

4. The method according to paragraph 2 wherein the heart failure is TAC-induced heart failure.

5. The method according to paragraph 1 wherein the subject is a human.

6. The method according to paragraph 1 wherein the modulator modulates SERCA2a post-translational SUMOylation.

7. The method according to paragraph 6 wherein the modulator is a vector comprising an expressible coding region encoding a protein selected from the group consisting of SERCA2a and SUMO1, and wherein the coding region is operably linked to at least one expression control element.

8. The method according to paragraph 7 wherein the vector is a recombinant adeno-associated virus.

9. The method according to paragraph 8 wherein the recombinant adeno-associated virus is rAAV1.

10. The method according to paragraph 1 wherein the modulator modulates SERCA2a post-translational acetylation.

11. The method according to paragraph 10 wherein the modulator is Sirt1 deacetylase.

12. A method of treating a cardiovascular disorder in a subject by inhibiting SERCA2a degradation comprising administering a therapeutically effective amount of a SUMO1 agent.

13. The method according to paragraph 12 wherein the SUMO1 agent is a vector comprising an expressible coding region encoding a protein selected from the group consisting of SERCA2a and SUMO1, and wherein the coding region is operably linked to at least one expression control element.

14. The method according to paragraph 13 wherein the vector is recombinant adeno-associated virus.

15. The method according to paragraph 14 wherein the recombinant adeno-associated virus is rAAV1.

16. A method of diagnosing a propensity to develop heart failure comprising determining the amino acid corresponding to a position selected from the group consisting of any of positions 479-482 and/or position 584-587 of human SERCA2a (SEQ ID NO:2).

17. A method of diagnosing a propensity to develop heart failure comprising determining the polynucleotide sequence encoding an amino acid corresponding to any of amino acids 479-482 or 584-587 of human SERCA2a (SEQ ID NO:1).

18. A method of diagnosing a propensity to develop heart failure comprising determining the level of expression of SUMO1 in a cardiomyocyte of a subject and comparing that level to the level of expression of SUMO1 in a cardiomyocyte of a healthy control, wherein reduced expression of SUMO1 relative to the control is indicative of a propensity to develop cardiac failure.

19. A method of screening for a therapeutic to treat heart failure comprising contacting SUMO1 and SERCA2a in the presence and absence of a candidate therapeutic and identifying the candidate therapeutic as a therapeutic if the level of SERCA2a SUMOylation is greater in the presence compared to the absence of the candidate therapeutic.

Other features and advantages of the present disclosure will become apparent from the following detailed description. It should be understood, however, that the detailed description and the specific examples, while indicating preferred embodiments, are provided for illustration only, because various changes and modifications within the spirit and scope of the invention will become apparent to those skilled in the art from the detailed description.

BRIEF DESCRIPTION OF THE DRAWING

FIG. 1. SERCA2a complex. (A) Two-dimensional SDS-PAGE gels of SERCA2a complex. Silver-stained SDS-PAGE gel shows a 12 kDa spot (arrow) immunoprecipitated with SERCA2a. Enrichment of SERCA2a was confirmed by Western blotting obtained from of the immunoprecipitated SERCA2a complex with rabbit anti-SERCA2a antibody (anti-S2a). Rabbit IgG (anti-IgG) complex used as a negative control. (B) The representative peptide fingerprint for SUMO1 identified by tandem mass spectrometric analysis. Protein sequence of SUMO1 with matched peptide shown in bold. (C) in vivo SERCA2a SUMOylation in HEK293 cells expressing flag-tagged SUMO1. Precipitated flag-tagged SUMO1 conjugates were analyzed by anti-SERCA2a. (D) Interaction between SERCA2a and Ubc9. HEK293 cells were transfected with expressing vectors for myc-tagged Ubc9 and SERCA2a or pcDNA vector (negative control). Cell lysates were subjected to immunoprecipitation (IP) with anti-myc and the resulting precipitates were subjected to Western blotting with anti-SERCA2a.

FIG. 8. Aligned amino acid sequences. Aligned amino acid sequences of wild-type SERCA2a from human (*Homo sapiens*, SEQ ID NO:2), pig (*Sus scrofa*, SEQ ID NO:4), rat (*Rattus norvegicus*, SEQ ID NO:6) and mouse (*Mus musculus*, SEQ ID NO:8) are presented. Residues noted herein as being involved in SERCA2a modifications are conserved, as evidenced by the conserved lysine residues at positions 480 and 585, as well as the conserved cysteine at position 674.

FIG. 9. Aligned polynucleotide sequences. Aligned polynucleotide coding region sequences encoding wild-type SERCA2a in human, pig, rat and mouse. These polynucleotide coding region sequences are presented in the sequence listing at positions 564-3557 of SEQ ID NO:1 for human SERCA2a, positions 14-3007 of SEQ ID NO:3 for pig SERCA2a, positions 507-3500 for rat SERCA2a, and positions 541-3537 for mouse SERCA2a.

DETAILED DESCRIPTION

Disclosed herein are data establishing that SERCA2a is SUMOylated at lysine residues 480 and 585 and that this SUMOylation preserves the ATPase activity and stability of SERCA2a. The significance of SUMOylation was further demonstrated by the observation that a SERCA2a variant (K480R/K585R) lacking the SUMOylated residues possessed a significantly reduced ATPase activity and stability. In isolated cardiomyocytes, adenovirus-mediated SUMO1 overexpression augmented contractility and calcium transients with an accelerated calcium decay. Transgene-mediated SUMO1 overexpression rescued pressure overload-induced cardiac dysfunction concomitantly with increased SERCA2a function. In contrast, down-regulation of SUMO1 level using shRNA accelerated pressure overload-induced deterioration of cardiac function accompanied by a decreased SERCA2a function. Taken together, the work disclosed herein shows that SUMOylation is a critical post-translational modification regulating SERCA2a function, and provides a method for treating a cardiac dysfunction or disorder, e.g., heart failure, by modifying intracellular calcium in the heart. Human clinical trials with a recombinant adeno-associated virus encoding SERCA2a (rAAV1/SERCA2a) have been initiated and the results indicate that targeting SERCA2a is a safe and effective modality for the treatment of human HF.

Figure 7:
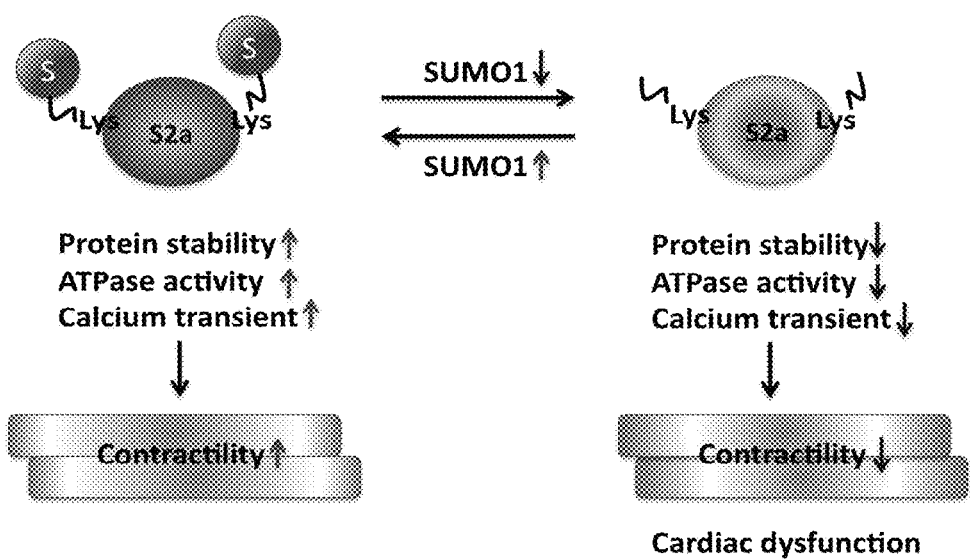
FIG. 7. A working model for regulation of SERCA2a function by SUMOylation. Under basal conditions, SUMOylation enhances SERCA2a protein stability and $Ca^{2+}$ pump functions to regulate cardiac contractility however, increasing unSUMOylated SERCA2a forms followed by low SUMO1 protein pool trigger impaired SERCA2a and cardiac dysfunction under the pathophysiological condition.

Disclosed herein for the first time is the SUMOylation of SERCA2a at two lysine residues. Interestingly, both SERCA2a levels and SUMOylation of SERCA2a were significantly reduced in failing hearts. Compelling evidence, disclosed in the Detailed Description below, established that the reduced SUMOylation of SERCA2a is a direct result of the reduced SUMO1 level in failing hearts. This reduced SUMOylation was strictly correlated with reduced ATPase activity of SERCA2a and with reduced SERCA2a stability. Moreover, restoration of SUMO1 reversed contractile dysfunctions in failing hearts. These results are summarized in FIG. 7.

Figure 3:
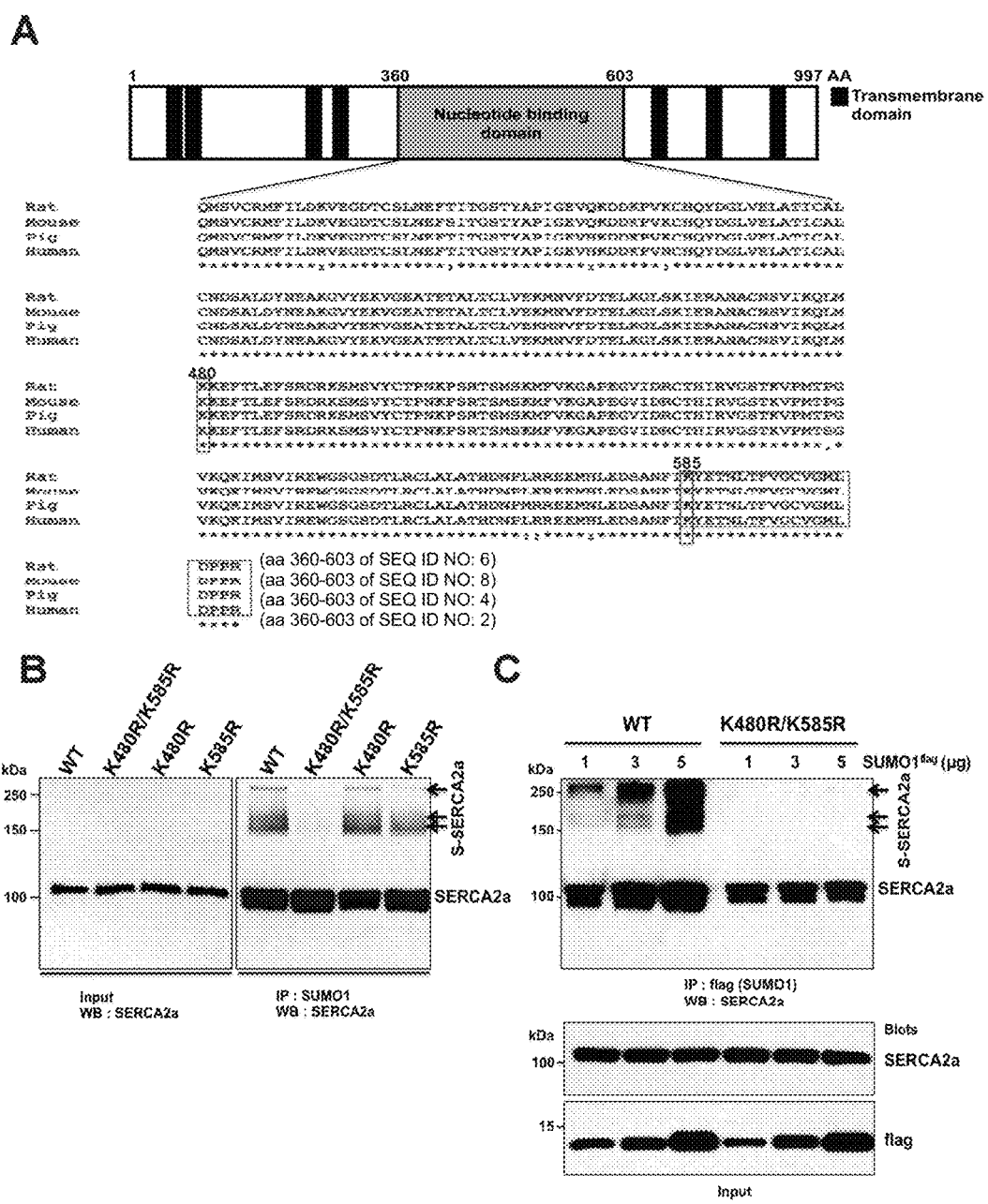
FIG. 3. SUMO1 is conjugated with lysines 480 and 585 of SERCA2a and is required for SERCA2a function. (A) N-domain of SERCA2a. Protein sequence alignment of SERCA2a of human, pig, rat and mouse from positions 360-603 of SEQ ID NOS:2, 4, 6 and 8, respectively. Putative SUMO consensus motifs (ΨKXE, where Ψ is a hydrophobic amino acid) contained the Lysine 480 and Lysine 585 of SERCA2a. SUMO modification sites of SERCA2a are marked by a black outline. Hydrolase domains are outline in a dotted line. (B) in vivo SUMOylation of SERCA2a. HEK293 cells were co-transfected with plasmids expressing flag-tagged SUMO1 and myc-tagged Ubc9 and WT or mutants SERCA2a. SUMOylated forms of SERCA2a were detected by Western blotting using anti-SERCA2a antibody. (C) Dose response of SUMO1 expression in SUMOylation of SERCA2a. HEK293 cells were co-transfected with myc-tagged Ubc9 and WT or K480R/K585R SERCA2a mutant. Indicated amount of flag-tagged SUMO1 or equal amount of the corresponding empty vector were added. Western blotting shows dose-effects of SUMO1 on SERCA2a SUMOylation. (D) $Ca^{2+}$-dependent ATPase activity of WT and K480R/K585R SERCA2a mutant in the presence and absence of additional SUMO1. The data shown were acquired from three independent experiments with each carried out in duplicate. (E) ATP binding capacity of WT and K480R/K585R SERCA2a. Transfected HEK293 cell lysates with indicated plasmids were affinity-precipitated with ATP-sepharose and subsequently subjected to Western blotting with anti-SERCA2a antibody. (F) Western blotting was also performed with indicated antibodies at different time points, i.e., a temporal series of HEK293 cell lysates were affinity-purified with ATP-sepharose and subjected to Western blot analysis with an anti-SERCA2a antibody. (G) Effects of SUMO1 overexpression on the protein stability of WT and K480R/K585R SERCA2a mutant in HEK293 cells. Quantification data are represented as the relative ratio of day 0 (n=3). All data represent means±SD. * $p<0.05$; ** $p<0.001$ vs. respective control using Student t-test.
Figure 3:
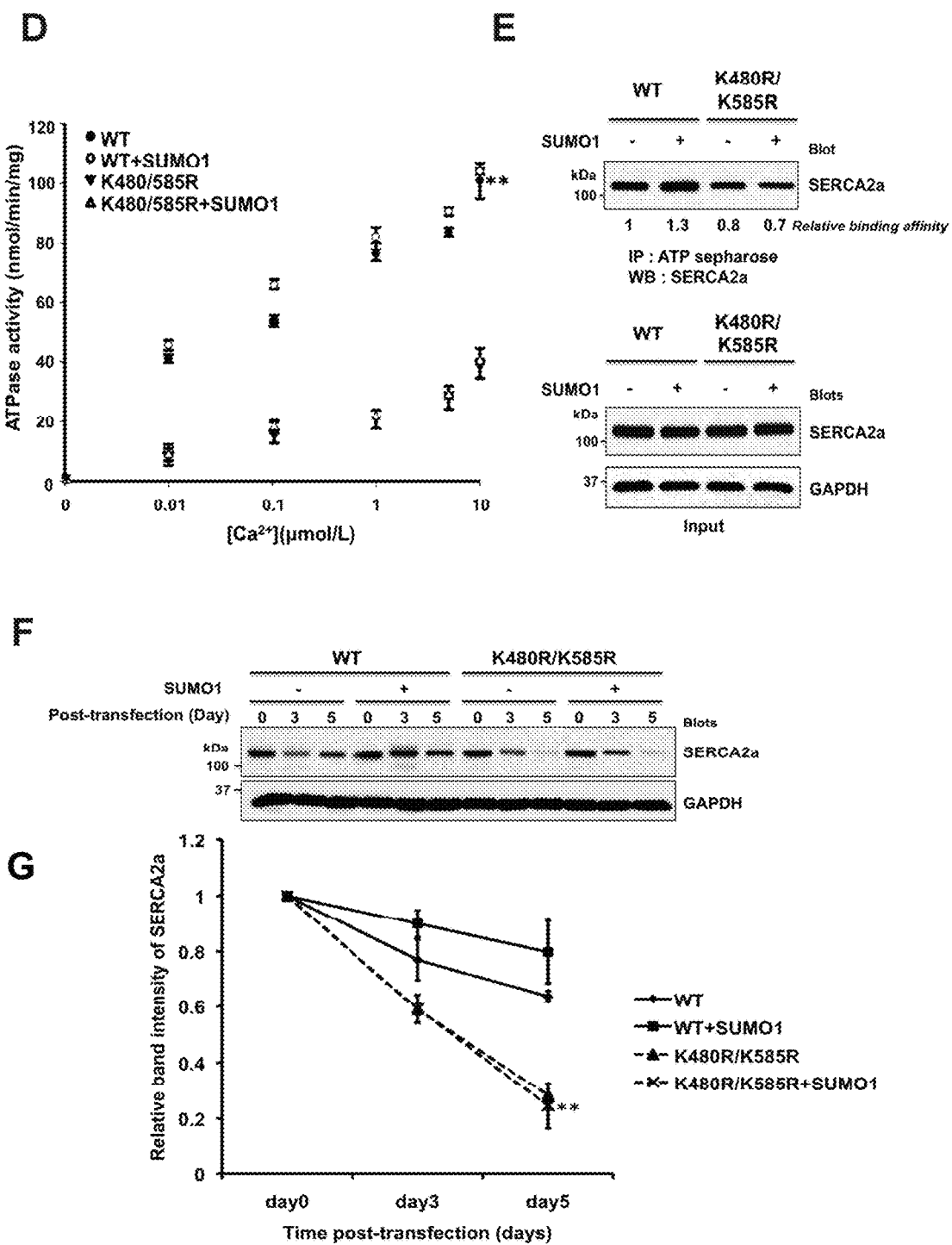

The conserved nature of the amino acid sequence of SERCA2a is illustrated in FIG. 8, which provides an aligned amino acid sequences for the SERCA2a of human (SEQ ID NO:2), pig (SEQ ID NO:4), rat (SEQ ID NO:6) and mouse (SEQ ID NO:8). In FIG. 9, aligned polynucleotide sequences encoding these SERCA2a amino acid sequences, with human (SEQ ID NO:1), pig (SEQ ID NO:3), rat (SEQ ID NO:5) and mouse (SEQ ID NO:7) polynucleotide sequences being presented. The SUMOylation motif noted in the brief description of FIG. 3 are found at positions 479-482 (MKKE, SEQ ID NOS:10, 12, 14, and 16 for human, pig, rat and mouse, respectively) and at positions 584-587 (IKYE, SEQ ID NOS:10, 12, 14, and 16). It is expected that single amino acid changes in either or both of these four-amino-acid motifs will modify SERCA2a in a manner that modulates its effect on cardiac function. It is further expected that most of these variations will interfere or inhibit SUMOylation of SERCA2a, leading to increased likelihood of cardiovascular disease such as HF. Accordingly, one method for diagnosing a disposition towards cardiovascular disease comprises obtaining a biological sample from a patient and determining the amino acid sequence of SERCA2a at positions 479-482 and/or positions 584-587 and diagnosing a disposition towards cardiovascular disease if the amino acid sequence varies from the wild-type sequence disclosed herein. Analogous diagnostic methods are contemplated for the encoding polynucleotide sequence(s).

Amino acid sequences of the SUMO-1 protein mediating the PTM of SERCA2a that affects cardiac function are also presented for human (SEQ ID NO:10), pig (SEQ ID NO:12), rat (SEQ ID NO:14) and mouse (SEQ ID NO:16). Polynucleotide sequences encoding these amino acid sequences are set forth in SEQ ID NOs:9, 11, 13, and 15 for human, pig, rat, and mouse, respectively.

Without wishing to be bound by theory, it is possible that the effect of SUMOylation on SERCA2a ATPase activity results from an induced conformational change in SERCA2a; alternatively, SUMOylation may lead to an additional interface for ATP binding, leading to an increase in ATPase activity. It is also possible that SUMOylation may affect other post-translational modifications (PTMs) of SERCA2a, such as the acetylation of particular residues. Previous studies indicated that a host of regulatory proteins were reciprocally and competitively regulated by SUMOylation and acetylation. For example, the transcriptional activity of tumor repressor gene HIC1 is promoted by SUMOylation and inhibited by acetylation (Van Rechem et al., 2010). Interestingly, acetylation of SERCA2a has been recently identified in a large-scale analysis of human acetylome in cancer cell lines (Choudhary et al., 2009). Also, it has been found that SERCA2a is acetylated and that this acetylation is more prominent in failing hearts and can be reversed by Sirt1 deacetylase.

The reciprocal regulation of SUMOylation and ubiquitination is consistent with SUMOylation stabilizing SERCA2a. This type of SUMOylation-mediated inhibition of protein degradation has been shown for other proteins. For example, SUMOylation of Axin, a negative regulator of Wnt signaling, prevented ubiquitination and thus conferred a prolonged half-life of Axin (Kim et al., 2008). Similarly, SUMOylation of p68 and p72 RNA helicases increased the stabilities of these proteins by reducing ubiquitin-proteasome-mediated protein degradation (Mooney et al., 2010).

The data disclosed herein establish that the SUMO1 level is significantly reduced in failing hearts, providing experimental basis for the position that cellular SUMO1 level should be precisely maintained and controlled for proper functions of cardiomyocytes. The finding disclosed herein that replenishment of SUMO1 reversed TAC-induced failing phenotypes indicated that reduced SUMO1 level is the direct cause of contractile dysfunction. The therapeutic effect of SUMO1 gene transfer was profound. In contrast to the reduced SUMO1 level, the protein level of the SUMOylating and de-SUMOylating enzymes, Ubc9 and SENP1, were unaltered in failing hearts and when shSUMO1 was administered. The level of Ubc9 and SENP1 was also unaltered when the SUMO1 level was restored. Therefore, the specificity and capacity of SUMOylation is unlikely to be changed in failing hearts. What matters most appears to be the reduced supply of SUMO1. In this regard, it is intriguing to note that depletion of cellular ubiquitin level is sufficient to cause neuronal dysfunction and death (Ryu et al., 2008).

In the experiments disclosed hereinbelow, a novel regulatory mechanism is disclosed whereby SUMOylation affects or modulates SERCA2a activity and overall contractile properties of the cardiac muscle cells. In addition, the impressive beneficial effects of SUMO1 on cardiac contractility and survival indicates that targeting SUMO1 will have a therapeutic value in the treatment of heart failure.

The following examples illustrate embodiments of the disclosure. Example 1 discloses the materials and methods used in the experiments described herein. Example 2 discloses data establishing that SUMO1 interacts with SERCA2a. Example 3 shows that SUMOylation of SERCA2a is reduced in failing hearts. Example 4 reveals that SERCA2a is SUMOylated at lysine residues K480 and K585. Example 5 shows that SUMOylation of SERCA2a increases the ATPase activity of SERCA2a. Example 6 establishes that SUMOylation enhances SERCA2a stability.

Example 7 shows that SUMO1 overexpression enhances cardiomyocyte contractility and enhances $Ca^{2+}$ transients in isolated cardiomyocytes. Example 8 further shows that SUMO1 overexpression improves cardiac function in TAC-induced heart failure. Example 9 shows that small hairpin RNA mediates down-regulation of SUMO1, which accelerates cardiac dysfunction.

Example 1

This example provides a description of the materials and methods used in the experiments disclosed herein.
In Vivo SUMOylation Assay
To analyze SUMOylation within cells, Lipofectamine 2000 was used to transfect HEK293 cells with plasmids encoding SERCA2a wild type (WT) or SERCA2a SUMOylation site mutants, along with flag-tagged SUMO1 and myc-tagged Ubc9. Cells were lysed by sonication in ice-cold lysis buffer (50 mM Tris-Cl, pH 8.0, 150 mM NaCl, 0.1% Triton X-100, 10 mM EDTA, complete protease inhibitor [one tablet per 10 ml; Roche], and protein phosphatase inhibitor cocktail (Sigma)) containing 20 mM N-ethylmaleimide. Lysates were cleared by centrifugation at 30,000 g for 20 minutes. Cell lysates were then subjected to immunoprecipitation by incubation with a flag-specific affinity matrix gel (Sigma) overnight at 4° C., after which the immunoprecipitates were washed in cold lysis buffer Immunocomplexes were resolved by SDS-PAGE, and subjected to Western blotting with SERCA2a-specific antibody, i.e., anti-SERCA2a antibody.

Fresh tissue extracts were prepared in lysis buffer for in vivo SUMOylation assays. Hearts from each experimental and control group were frozen in liquid nitrogen. Frozen tissues were crushed and homogenized in lysis buffer, as described above, using the MP homogenate system (Fast-Prep homogenizer). The insoluble portion was removed by centrifugation at 30,000 g for 20 minutes. Extracts were incubated with anti-SUMO1 agarose resin with agitation overnight. The SUMO conjugated forms were detected by Western blotting with specific primary antibodies.
SERCA2a Activity Assay Crude microsome was prepared as previously described (Clarke et al., 1989). SERCA2a activity assays were performed using pyruvate/NADH-coupled reactions, as previously described (Hajjar et al., 1997). The activity of the $Ca^{2+}$-ATPase was calculated as follows: $\Delta$absorbance/6.22× protein×time (in nmol ATP/mg protein×min) All assays were done in triplicate.
Generation of Conditional SUMO1 Transgenic Mouse The αMHC-flox-mouse SUMO1 transgene was subcloned into the pML2G vector, which has an EGFP cDNA between two loxP sites. The DNA construct was microinjected into fertilized eggs from B6C3 mice and transgenic integration was confirmed by PCR.
Statistical Analysis The analysis was performed using the Student's t test, with significant differences demarcated by a single asterisk (*), indicating $p<0.05$, or by a double asterisk (**), indicating $p<0.001$. Data in figures represent mean±SD.

Example 2

Figure 1:
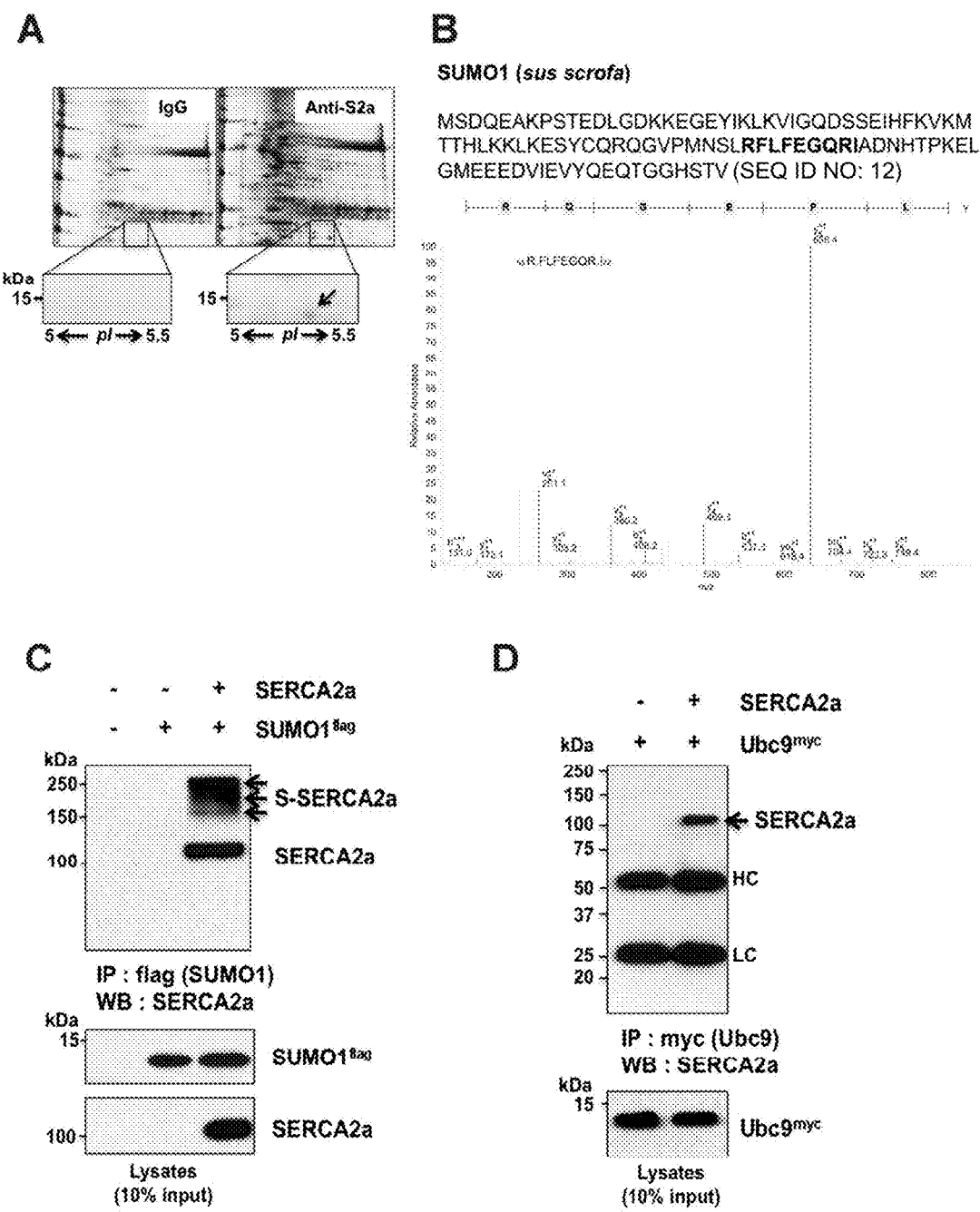

SUMO1 Interacts with SERCA2a
As an approach to identify novel modifiers of SERCA2a, the SERCA2a-associated protein complex was isolated from porcine heart lysates by immunoprecipitation with anti-SERCA2a antibody and then analyzed by two-dimensional electrophoresis (FIG. 1A). MS/MS analysis of the stained protein spots revealed that SUMO1 is co-precipitated with SERCA2a. A representative MS/MS peptide fingerprint for SUMO1 is shown in FIG. 1B. HEK293 cells were co-transfected with plasmids encoding SERCA2a and flag-tagged SUMO1 Immunoprecipitation with anti-flag antibody followed by Western blotting with anti-SERCA2a antibody showed that SERCA2a indeed binds to SUMO1 (FIG. 1C). A similar experiment performed with HEK293 cells co-transfected with plasmids encoding SERCA2a and MYC-tagged Ubc9, a SUMO conjugating enzyme, also confirmed that SERCA2a binds to Ubc9 (FIG. 1D). These data establish that SERCA2a is a target of SUMOylation.

Example 3

SUMOylation of SERCA2a is Reduced in Failing Hearts
We then examined whether SERCA2a is indeed SUMOylated in hearts. Human heart lysates were immunoprecipitated with anti-SUMO1 antibody and probed with anti-SERCA2a antibody. In addition to a normal SERCA2a band (~110 kDa), slowly migrating SERCA2a bands (150~250 kDa) were detected (FIG. 2A, top) which represent the SUMOylated SERCA2a. The level of SUMOylated SERCA2a was significantly reduced in failing hearts (HF) compared to normal hearts (NF). In addition, SERCA2a levels were significantly reduced in the failing hearts, consistent with previous reports, and supporting the validity of the heart sample preparations. Along with this reduced SERCA2a level, SUMO1 level was also significantly reduced in the failing hearts. In contrast, the levels of Ubc9 and SENP1, the critical SUMOylating and de-SUMOylating enzymes, respectively, were unaltered in the failing hearts (FIG. 2A, bottom). These data indicated that the reduced SUMOylation of SERCA2a might be primarily due to the reduced level of SUMO1 but not to the reduced SUMOylating or elevated de-SUMOylating activities.

We have also observed that SUMO1 level as well as SERCA2a level were significantly reduced in a murine model of HF induced by pressure-overload (FIG. 2B) and in a porcine model of HF induced by volume-overload (FIG. 2C). These results established that reduced SUMOylation of SERCA2a caused by a reduced SUMO1 level is a prevailing characteristic associated with the development of HF in diverse mammalian species.

Example 4

SERCA2a is SUMOylated at Lysines 480 and 585
SUMOylation of target proteins is known to occur on lysine residues in the context of a highly conserved recognition motif, $\Psi K \chi E/D$ (where $\Psi$ stands for a large hydrophobic amino acid and $\chi$ for any amino acid) (Sampson et al., 2001). Three independent SUMOylation prediction programs (available at bioinformatics.lcd.ustd.org, at abgent-.com/cn/doc/sumoplot, and at sumosp.biocuckoo.org/prediction.php) identified two putative SUMO conjugating sites in SERCA2a, lysines 480 (K480) and 585 (K585). These lysine residues are located in the cytosolic nucleotide-binding domain where ATP binds and are perfectly conserved in mouse, rat, pig, and human SERCA2a (FIG. 3A).

To investigate the role of SERCA2a K480 and K585 during SUMOylation, we generated three SERCA2a variants in which K480 or K585 was replaced by arginine (K480R and K585R, respectively) or both K480 and K585 were replaced by arginine (K480R/K585R). HEK293 cells were transfected with plasmids encoding wild type (WT)

and these SERCA2a variants, and then the cell lysates were immunoprecipitated with anti-SUMO1 antibody and probed with anti-SERCA2a antibody. While K480R and K585R were SUMOylated indistinguishably from WT SERCA2a, K480R/K585R was completely unSUMOylated (FIG. 3B). The SUMOylation of WT SERCA2a was enhanced when increasing amounts of the SUMO1 plasmid were co-transfected in a dose-dependent manner, whereas SUMOylation of K480R/K585R was completely abolished (FIG. 4C). Taken together, these results indicate that SERCA2a is SUMOylated at the K480 and K585 residues.

Example 5

SUMOylation Increases SERCA2a ATPase Activity

Since the SUMOylated lysine residues, K480 and K585, reside in the nucleotide-binding domains of SERCA2a, SUMOylation may affect the SERCA2a ATPase activity. WT and SUMOylation-defective K480R/K585R SERCA2a were immune-precipitated from the lysates of HEK293 cells transfected with the corresponding plasmids, along with the empty or SUMO1-expressing plasmids, and ATPase activities were determined. K480R/K585R possessed a significantly decreased Vmax compared to WT SERCA2a (WT; 94.60±1.63, K480R/K585R; 37.95±5.40 nmol/min/mg) and a significantly increased EC50 value compared to WT SERCA2a (WT; 0.24±0.09, K480R/K585R; 0.76±0.17 nmol $Ca^{2+}$/L). Co-expression of SUMO1 significantly increased Vmax (98.58±1.83 nmol/min/mg) and decreased EC50 (0.11±0.09 nmol $Ca^{2+}$/L) in WT SERCA2a, whereas it does not affect the ATPase activity of K480R/K585R (FIG. 3D).

Further tests addressed whether SUMOylation affected the ATP-binding affinity of SERCA2a. HEK293 cells were transfected with WT or K480R/K585R SERCA2a-expressing plasmids, along with the empty or SUMO1-expressing plasmids. Cell lysates were incubated with ATP-sepharose and the resulting precipitates were probed with anti-SERCA2a antibody. The results indicated that co-expression of SUMO significantly increased the ATP-binding affinity of SERCA2a. In contrast, K480R/K585R possessed a significantly reduced ATP-binding affinity, which was not affected by the co-expression of SUMO1 (FIG. 3E). These data establish that SUMOylation increased the ATPase activity of SERCA2a, at least partly by enhancing ATP-binding affinity.

Example 6

SUMO1 Enhances the Stability of SERCA2a Protein

Figure 2:
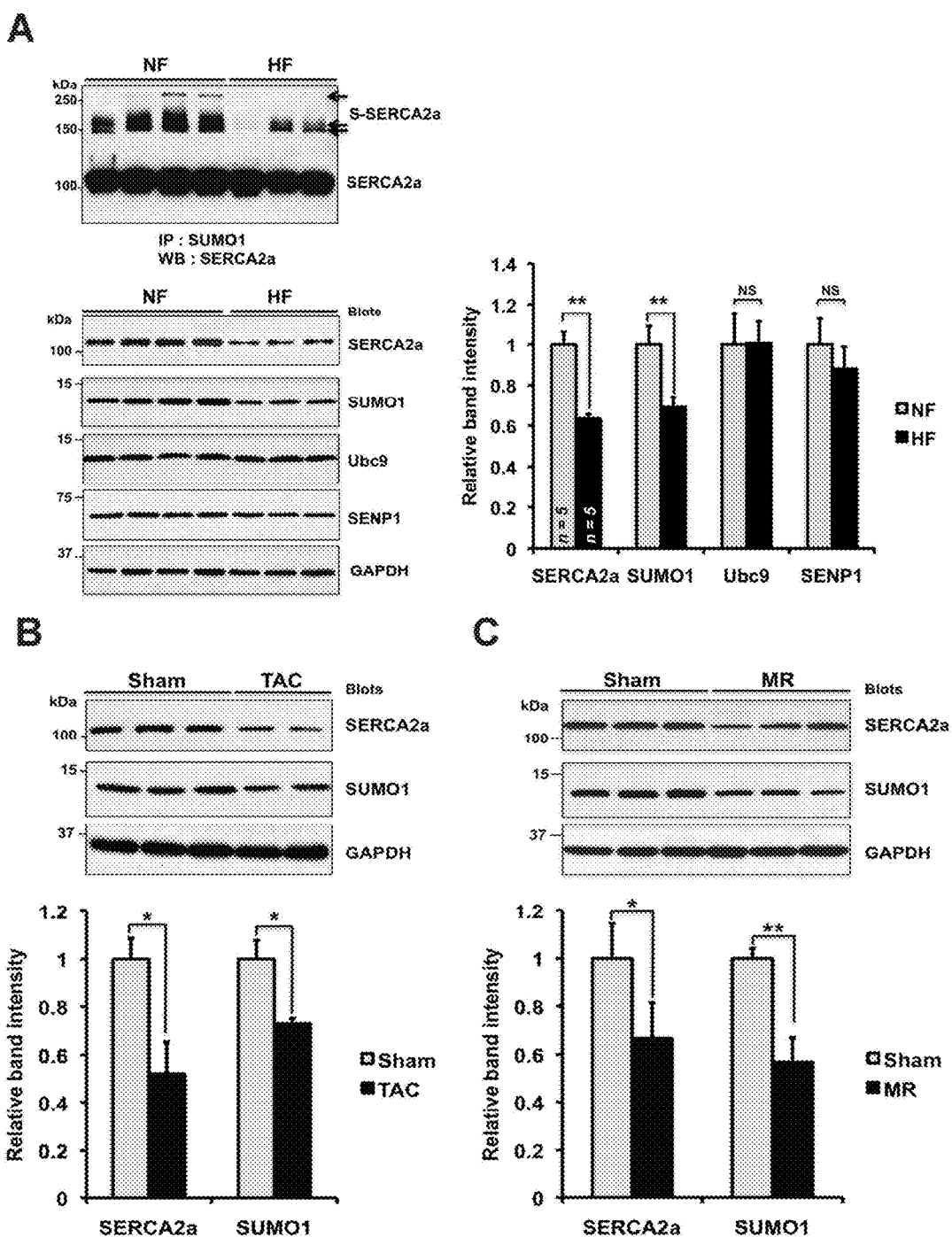
FIG. 2. Endogenous SUMO1 protein level is decreased in both experimental model and human heart failure. (A) SERCA2a SUMOylation in human cardiac tissues. Representative blots showing protein expressions with subsequent quantification (n=5 per each group). S-SERCA2a: SUMOylated SERCA2a. (B) Representative Western blotting of SUMO1 and SERCA2a in TAC-induced mouse model of heart failure with subsequent quantification. TAC-induced failing hearts (TAC, n=5); sham-operated control hearts (Sham, n=8). (C) Western blotting of one representative experiment with subsequent quantification. The protein amounts of SUMO1 and SERCA2a in the heart of eight pigs were analyzed. MR-induced failing porcine hearts (MR, n=3); Sham-operated control hearts (Sham, n=5). Protein band intensities were assessed by densitometry using the ImageJ system. The internal standard GAPDH was used to normalize for equal protein loading. All data represent means±SD. * $p<0.05$ vs. respective control using Student t-test. TAC: trans-aortic constriction, MR: mitral valve regurgitation, NF: non-failing, or normal, heart.

The data disclosed herein establish that the SERCA2a level was reduced in failing hearts concomitantly with a reduced SUMO1 level (FIG. 2). As a consequence, the possibility that SUMOylation affects the stability of SERCA2a was investigated. HEK293 cells were transfected with WT or K480R/K585R SERCA2a expressing plasmids, along with the empty or SUMO1-expressing plasmids. At forty-eight hours after transfection, the cells were treated with cycloheximide, an inhibitor of protein synthesis, to block further de novo synthesis of SERCA2a. After incubation for an additional three and five days, the SERCA2a levels were determined by Western blotting. The estimated half-life of WT SERCA2a was 4.90±0.70 days, whereas it increased to 5.90±0.20 days when SUMO1 was co-expressed. The estimated half-life of K480R/K585R was significantly reduced (2.42±0.50 and 2.35±0.80 days with and without co-expression of SUMO1, respectively) compared to WT SERCA2a (FIGS. 3F and 3G). These data indicate that SUMOylation increased the stability of SERCA2a.

Example 7

Figure 4:
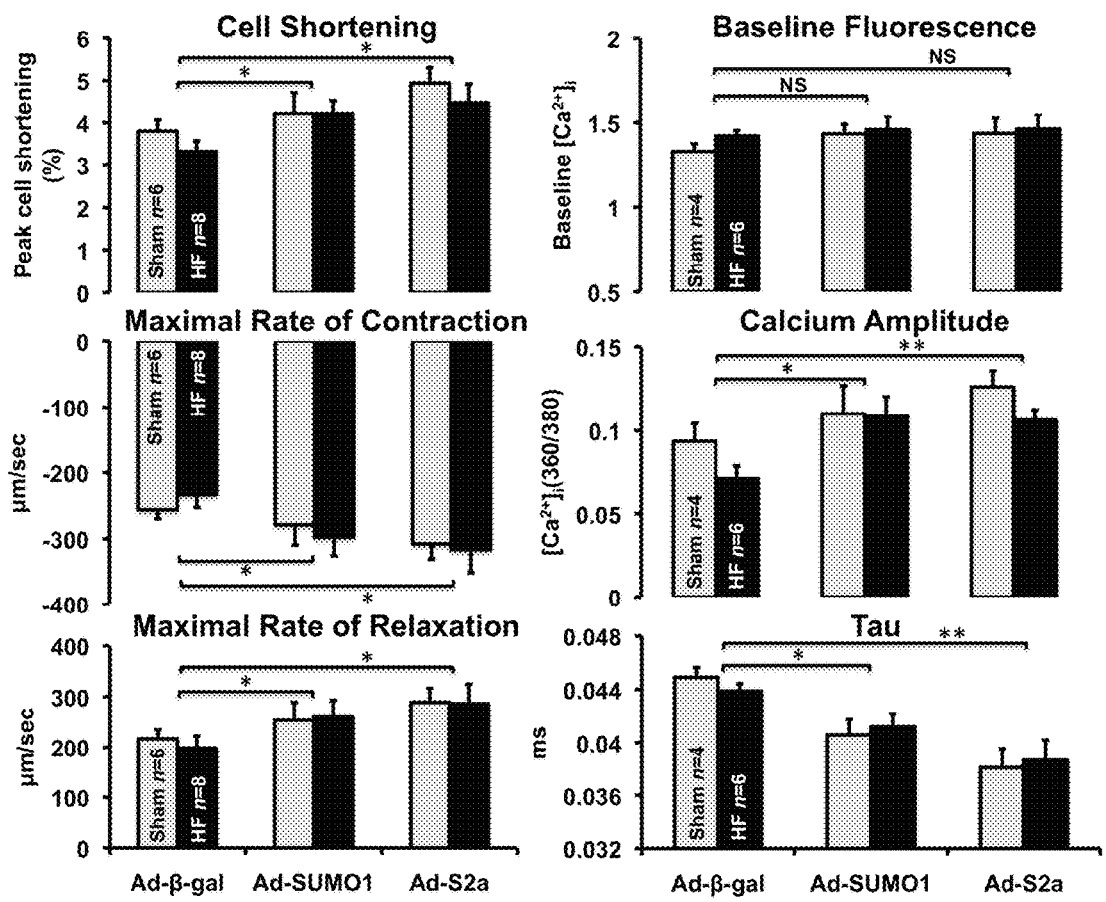
FIG. 4. SUMO1 overexpression enhances cardiomyocytes contractility and calcium transients in both normal and failing cardiomyocytes. Average parameters of cardiomyocytes contraction were determined (Sham contractility, n=6 mice/143 cells; HF contractility, n=8 mice/181 cells). Average parameters of $Ca^{2+}$ transient properties were determined (Sham calcium transient, n=4 mice/65 cells; HF calcium transient, n=6 mice/131 cells). All data represent means±SD. * $p<0.05$; ** $p<0.001$ vs. respective control using Student t-test.

SUMO1 Overexpression Enhances Cardiomyocyte Contractility and $Ca^{2+}$ Transients in Isolated Cardiomyocytes To examine the physiological function of SUMO1, mouse adult cardiomyocytes were isolated from normal (Sham) or TAC-induced failing hearts (HF), and then infected with either adenovirus expressing β-gal (Ad-β-gal) or SUMO1 (Ad-SUMO1). Contractile properties were determined using a dual-excitation spectrofluorometer equipped with a video-edge detection system. When infected with Ad-SUMO1, normal cardiomyocytes showed enhanced contractility with an 11% increase in cell shortening, a 17% increase in maximal rate of contraction, and a 9% increase in the maximal relaxation in comparison with the Ad-β-gal-infected cardiomyocytes. More prominent enhancement in contractility was observed when the failing cardiomyocytes were infected with Ad-SUMO1 with a 27% increase in cell shortening, a 30% increase in maximal rate of contraction, and a 27% increase in maximal relaxation. Ad-SUMO1-infected cardiomyocytes showed increased calcium amplitude and $Ca^{2+}$ decay in comparison with Ad-β-gal-infected cardiomyocytes. The overall inotropic effect of SUMO1 overexpression was comparable to the effect when SERCA2a is overexpressed (FIG. 4). It is expected that SUMO1 overexpression enhanced cardiomyocyte contractility, at least partly through increasing the enzymatic activity and stability of SERCA2a.

Example 8

SUMO1 Overexpression Improves Cardiac Function in TAC-Induced Heart Failure

Figure 5:
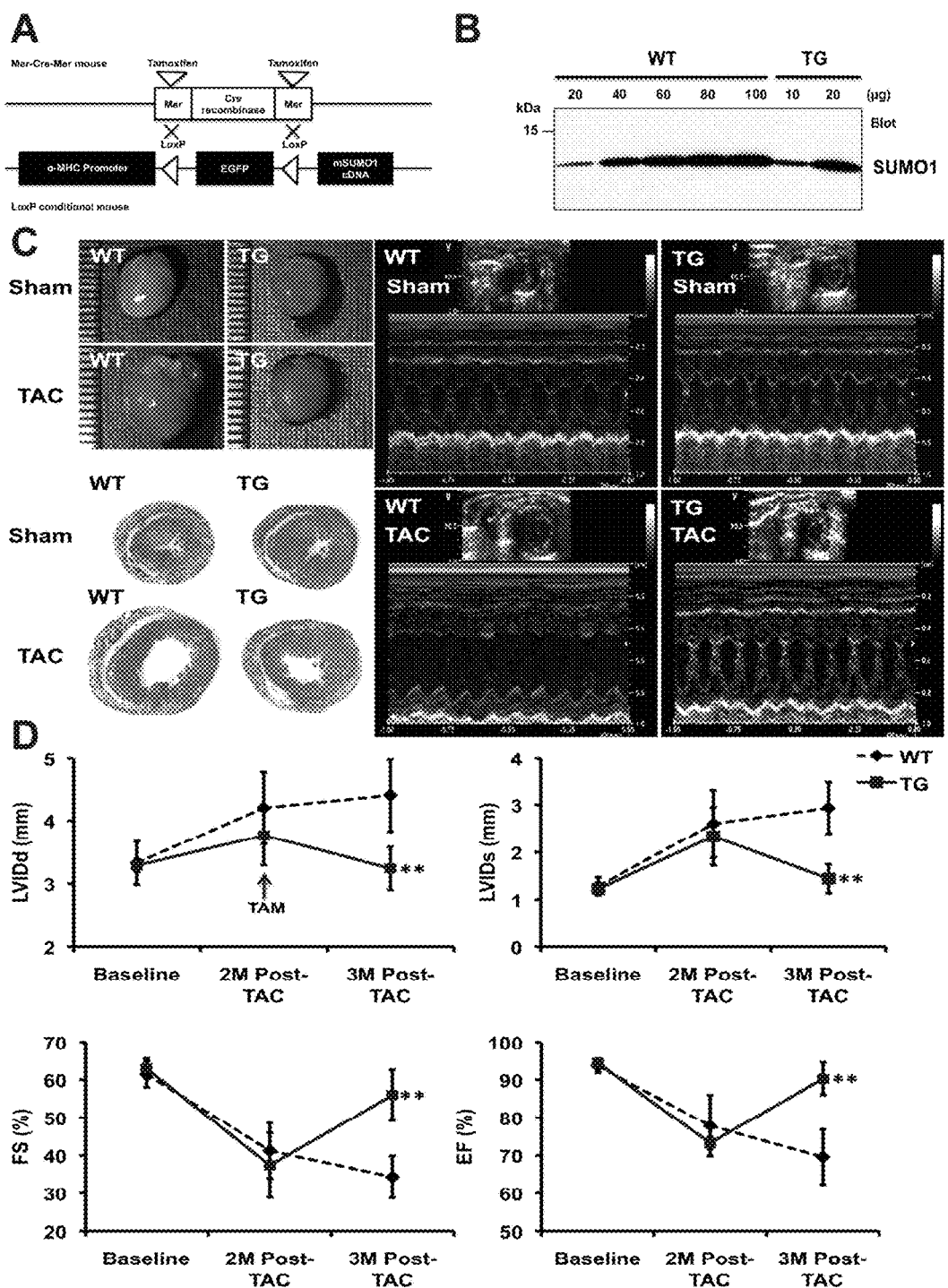
FIG. 5. SUMO1 overexpression restores TAC-induced cardiac dysfunctions. (A) Generation of conditional SUMO1 transgenic mice. Cardiac SUMO1 express under the control of the α-MHC promoter. (B) Western blotting represents cardiac SUMO1 overexpression in transgenic mice. WT: wild type littermates, TG: SUMO1 transgenic mice. (C) Representative gross hearts (top left), hematoxylin and eosin staining (bottom left) and M-mode imaging (right) shows morphology of the heart, left ventricular function and dimensions in WT and SUMO1 transgenic mice at 3 months post-TAC operations time point. (D) Echocardiographic measurements of internal diameters in end-diastole (LVIDd), end-systole (LVIDs), fractional shortening (FS) and ejection fraction (EF). Sham: WT, n=12; TG, n=10; TAC: WT, n=14; TG, n=12. (E) Kaplan-Meier survival curves in response to TAC operations. WT represents a dotted line (n=15) and SUMO1 transgenic mice represents closed line (n=14). (F) Representative Western blotting shows alternations of cardiac protein expressions in SUMO1 transgenic mice (left). Band intensities were quantified by densitometry measurement and normalized with GAPDH control. Data are represented as the relative ratio (n=4 per each group, right). (G) $Ca^{2+}$-dependent ATPase activity of SERCA2a in preparations from sham-operated WT (○), sham-operated SUMO1 transgenic mice (●), preparations from TAC-operated WT (▽), and TAC-operated SUMO1 transgenic mice (▲) hearts (n=3 per each group). All data represent means±SD. * $p<0.05$; ** $p<0.001$ vs. respective control using Student t-test. NS: non-significant.
Figure 5:
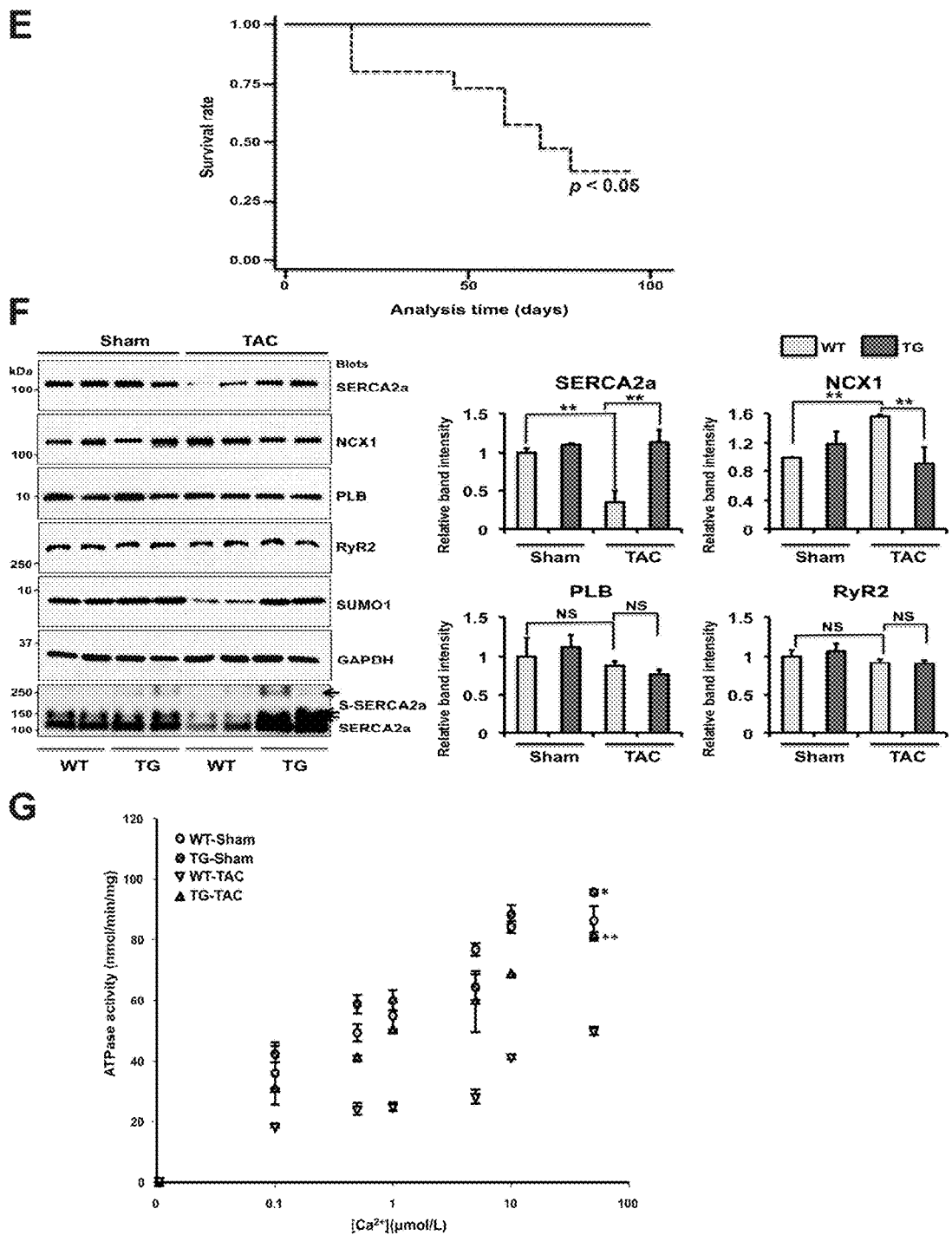

We proceeded to define the physiological consequences of SUMO1 overexpression in vivo. For this purpose, we utilized a Cre/loxP conditional expression system in which administration of tamoxifen induced heart-specific SUMO1 overexpression in exchange of EGFP expression (FIG. 5A). No apparent cardiac dysfunctions were seen in this transgenic mouse (Table S1). Western blotting revealed that tamoxifen-induced SUMO1 expression level in transgenic mice (TG) was approximately 5-fold higher than that of wild type littermates (WT) (FIG. 5B).

WT and TG mice were subjected to TAC operation. HF with an approximately 40-50% decrease in fractional shortening (FS) was developed in two months. Tamoxifen was then administered for four days to induce SUMO1 overexpression. Along with the increased SUMO1 level, SUMOylation and the protein level of SERCA2a were significantly induced by the administration of tamoxifen (Figure S2). One month later (three months post-TAC in total), cardiac functions were examined by histology and echocardiography. Representative heart sections and M-mode echocardiographic data are shown in FIG. 5C. WT and TG mice were indistinguishable at baseline. At three months post-TAC, WT mice exhibited severe failing phenotypes with significant left ventricular (LV) dilation and reduced FS and ejection fraction (EF). Tamoxifen-induced SUMO1 overexpression, however, dramatically reversed these failing phenotypes with less LV dilation (LV internal diastolic dimension (LVIDd), 3.24±0.33 mm in TG vs. 4.40±0.57 mm in WT, $p<0.001$; LV internal systolic dimension (LVIDs), 1.44±0.30 mm in TG vs. 2.93±0.54 mm in WT, $p<0.001$)

and improved FS (55.91±6.70% in TG vs. 34.30±5.56% in WT, p<0.001) and EF (90.26±4.27% in TG vs. 69.57±7.28% in WT, p<0.001) (FIG. 5D).

Hemodynamic analyses also showed improved LV function in TG. The end-systolic pressure-volume relationship (ESPVR) in LV was slightly steeper in TG animals than WT, suggesting an increased cardiac contractility (Figure S3). In contrast, the slope of LV end-diastolic pressure-volume relationship (EDPVR) was decreased in TG mice, indicating a decreased end-diastolic LV chamber stiffness. Parameters of LV dilation including stroke volume, end-diastolic volume, and end-systolic volume were likewise restored in TG. In addition, an increase in heart weight to body weight ratio was significantly inhibited in TG (Table S2).

The recovery of cardiac dysfunction by SUMO1 was also manifested by increased survival of TG under prolonged pressure-overload (FIG. 5E). The survived mice were 14 out of 14 (100%) in TG, whereas they were only 7 out of 15 (47%) in WT at 100 days after administration of tamoxifen.

We performed Western blotting to monitor expression levels of key regulatory proteins involved in $Ca^{2+}$ homeostasis. Notable changes under TAC were a reduction of the SERCA2a level (65% decrease vs. sham), which is consistent with the numerous previous reports, and an increase in NCX1 level (56% increase vs. sham) NCX1 is responsible for cytosolic $Ca^{2+}$ elimination during diastole. It was previously shown that a decrease in SERCA function is coupled with an increase in NCX function in failing hearts (Schillinger et al., 2003; Studer et al., 1994) and in isolated cardiomyocytes after delivery of siRNA against SERCA2a (Seth et al., 2004). These TAC-induced changes in the levels of SERCA2a and NCX1 were normalized in TG (FIG. 5F).

TAC resulted in a significant reduction in the ATPase activity of SERCA2a in WT with a 50% decrease in Vmax (TAC; 40.39±5.08, Sham; 81.03±7.11 nmol/min/mg) and a 120% increase in EC50 (TAC; 0.31±0.021, Sham; 0.14±0.08 µnmol $Ca^{2+}$/L). This TAC-induced reduction in the ATPase activity was significantly ameliorated in TG with a 15% decrease in Vmax (TAC; 70.32±5.54, Sham; 82.29±5.39 nmol/min/mg) and a 59% increase in EC50 (TAC; 0.27±0.12, Sham; 0.166±0.09 µnmol $Ca^{2+}$/L), however.

Taken together, these data indicate that SUMO1 overexpression restores cardiac dysfunction induced by pressure-overload.

Example 9 shRNA-Mediated Down-Regulation of SUMO1 Accelerates Cardiac Dysfunction

Figure 6:
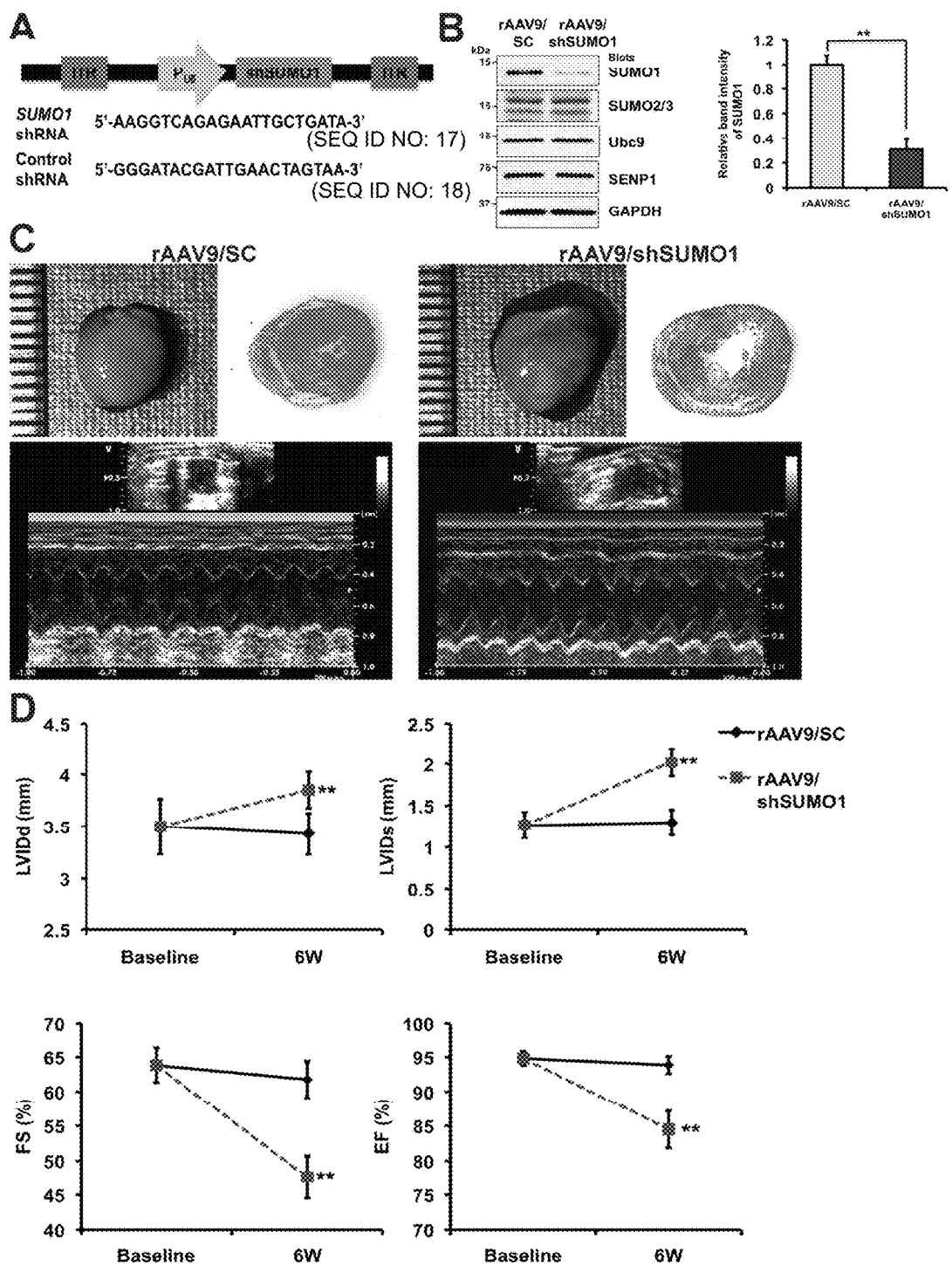
FIG. 6. Reduction of SUMO1 level accelerated cardiac dysfunction. (A) SUMO1 shRNA construct design. The rAAV expresses a SUMO1 shRNA sequence under the control of U6 promoter. Scramble expression cassette was cloned into the same viral vectors. (B) Representative Western blotting of cardiac tissue extracts from mice delivered with rAAV9 expressing scrambled control shRNA (rAAV9/SC) or shRNA against SUMO1 (rAAV9/shSUMO1) at 3 weeks after injection (left). Total extracts were probed with indicated antibodies Inhibition of cardiac SUMO1 expression was measured (n=5 per each group, right). (C) Representative gross (top left), section of the hearts (top right) and M-mode imaging (bottom) shows heart morphology, cardiac function and dimensions in mice injected rAAVs at 6 weeks after injection. (D) Assessments of the internal diameters in end-diastole (LVIDd), end-systole (LVIDs), fractional shortening (FS), and ejection fraction (EF) of rAAV9/shSC and rAAV9/shSUMO1. Echocardiographic parameters were determined (n=14 per each group). (E) Survival of animals with rAAV9-mediated cardiac knockdown of SUMO1. Kaplan-Meier method was used to analyze lifespan of animals obtained by different dose of rAAV9/shSUMO1 (n=14 per each group) or rAAV9/shSC injection (n=24). (F) Representative Western blotting shows expression levels of cardiac proteins (left panel). 6 weeks after tail-vein injection with rAAV9/shSC (n=4) or rAAV9/shSUMO1 (n=7) were analyzed by Western blotting with indicated antibodies. Data are represented as the relative ratio. (G) $Ca^{2+}$-dependence of SERCA2a's ATPase activity was demonstrated in preparations from scramble (•) injected and shRNA against SUMO1 (•) injected hearts (n=3 per each group). For each concentration, the upper data point is rAAV9/SC; the lower data point is rAAV9/shSUMO1. All data represent means±SD. * $p<0.05$; ** $p<0.001$ vs. respective control using Student t-test. NS: non-significant.
Figure 6:
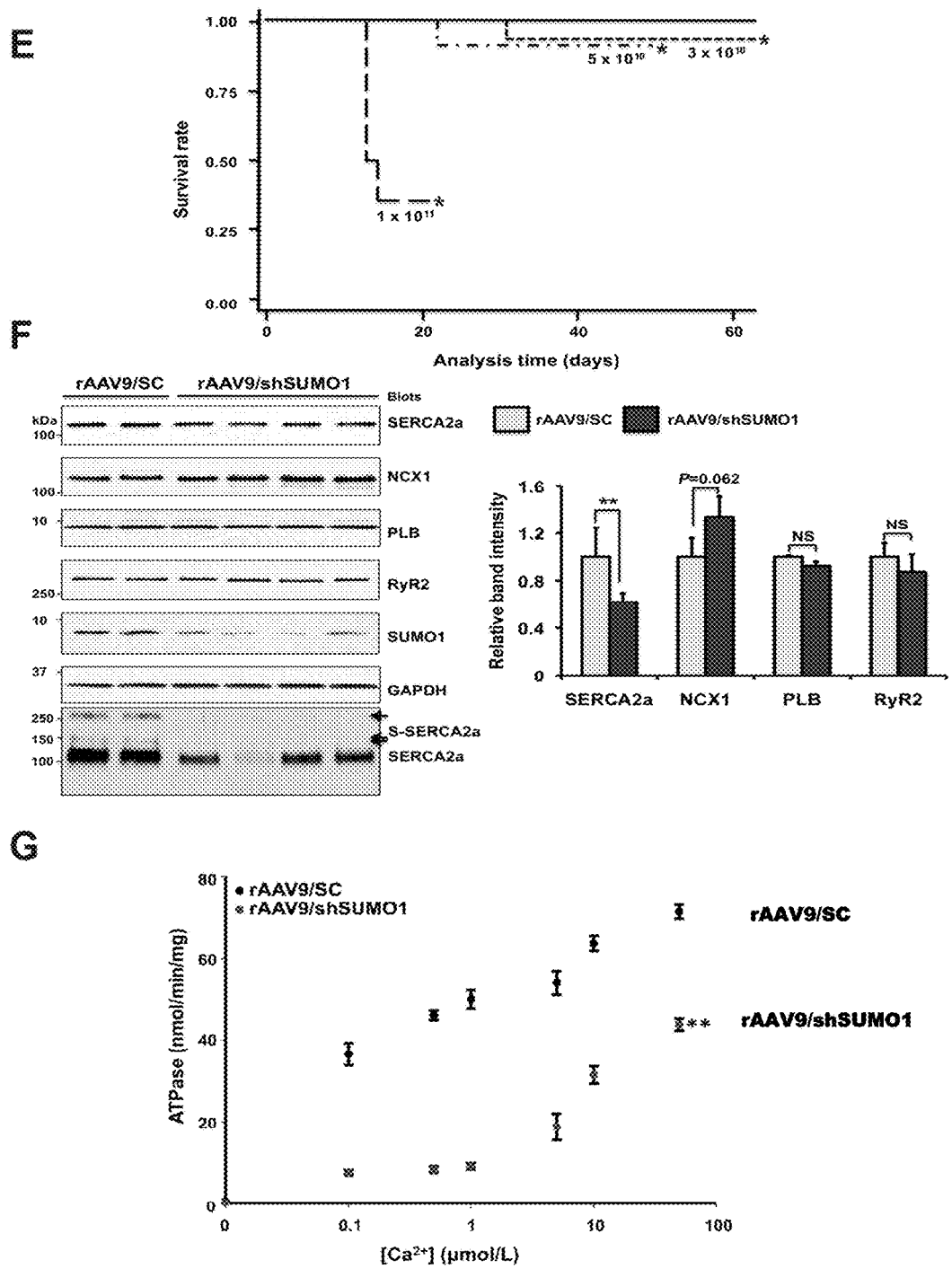

To evaluate the effects of down-regulation of SUMO1 in hearts, we generated recombinant adeno-associated viruses serotype 9 (rAAV9) that express SUMO1-directed short hairpin RNA, or shRNA, (rAAV9/shSUMO1), or a scrambled sequence (rAAV9/SC) under the control of the U6 promoter (FIG. 6A). These rAAV constructs were injected into B6C3/F1 male mice through the tail vein at a dose of $5×10^{10}$ viral genomes (vg)/mouse. At three weeks after injection, Western blotting with heart extracts revealed that SUMO1 levels were reduced by approximately 70% in the rAAV9/shSUMO1-injected hearts but not in the rAAV9/SC-injected hearts. Expression levels of SUMO2, SUMO3, Ubc9, and SENP1 were not affected by rAAV9/shSUMO1 (FIG. 6B).

At six weeks after injection, cardiac functions were evaluated. Gross morphology of the hearts and representative M-mode images of echocardiographic analyses are shown in FIG. 6C. Hearts from rAAV9/shSUMO1-injected mice showed prominent left ventricle (LV) dilation and functional deterioration compared with the hearts from rAAV9/SC-injected mice with an increased Left Ventricular Internal Dimension-diastole, or LVIDd, (shSUMO1; 3.85±0.17 mm, SC; 3.42±0.19 mm, p<0.001), and Left Ventricular Internal Dimension-systole, or LVIDs, (shSUMO1; 2.02±0.17 mm, SC; 1.30±0.12 mm, p<0.001), and decreased FS (shSUMO1; 47.63±3.07%, SC; 61.77±4.77%, p<0.001) and EF (shSUMO1; 84.51±2.63%, SC; 93.85±1.23%, p<0.001) (FIG. 6D).

Hemodynamic analyses showed that injection of rAAV9/shSUMO1 resulted in a rightward shift of the LV pressure-volume loops and a decreased End-Systolic Pressure-Volume Relationship, or ESPVR, indicating negative inotropic effects of SUMO1 down-regulation. Injection of an increased dose of rAAV9/shSUMO1 resulted in a more severe cardiac dysfunction (Figures S4A and S4B). An increased heart weight to body weight ratio was also observed in rAAV9/shSUMO1-injected hearts (Table S3).

The rAAV9/shSUMO1-induced cardiac dysfunction was manifested by sudden deaths of the rAAV9/shSUMO1-injected mice. All the mice received $1×10^{11}$ vg of rAAV9/shSUMO1 died within three weeks. Death rates of mice received $3×10^{10}$ vg and $5×10^{10}$ vg of rAAV9/shSUMO1 were slightly higher than, but not statistically significant from, that of control mice received rAAV9/SC. During the period of experiments, none of the control mice died (FIG. 6E).

Western blotting revealed that SERCA2a protein level was decreased by approximately 40% in rAAV9/shSUMO1-injected hearts. Related to this, the sodium/calcium exchanger NCX1 protein level was slightly elevated, although the elevation was not statistically significant. PLN (phospholamban) and RyR2 (ryanodine receptor 2) protein levels, however, were not altered. As expected, SUMOylation of SERCA2a was also significantly blunted (FIG. 6F). SUMOylation of PLN and RyR2 were not altered (FIG. S4C). These results establish that SUMO1 increases SERCA2a SUMOylation and SERCA2a stability.

SUMO1 down-regulation by injection of rAAV9/shSUMO1 suppressed the ATPase activity of SERCA2a with a reduced Vmax (shSUMO1; 48.11±6.34, SC; 61.12±6.49 nmol/min/mg) and an increased EC50 (shSUMO1; 5.69±0.23, SC; 0.10±0.07 µmol/L) (FIG. 6G). The ATPase activity of SERCA2a was more severely impaired when a higher dose of rAAV9/shSUMO1 was injected (FIG. S4D).

Taken together, the data disclosed herein establish that SUMO1 is an essential regulator of SERCA2a function in the heart.

Each of the references cited herein is hereby incorporated by reference in its entirety.

REFERENCES

Adachi, T., Weisbrod, R. M., Pimentel, D. R., Ying, J., Sharov, V. S., Schoneich, C., and Cohen, R. A. (2004). S-Glutathiolation by peroxynitrite activates SERCA during arterial relaxation by nitric oxide. Nat Med 10, 1200-1207.

Benson, M. D., Li, Q. J., Kieckhafer, K., Dudek, D., Whorton, M. R., Sunahara, R. K., Iniguez-Lluhi, J. A., and Martens, J. R. (2007). SUMO modification regulates inactivation of the voltage-gated potassium channel Kv1.5. Proc Natl Acad Sci USA 104, 1805-1810.

Byrne, M. J., Power, J. M., Preovolos, A., Mariani, J. A., Hajjar, R. J., and Kaye, D. M. (2008). Recirculating cardiac delivery of AAV2/1SERCA2a improves myocardial function in an experimental model of heart failure in large animals. Gene Ther 15, 1550-1557.

Choudhary, C., Kumar, C., Gnad, F., Nielsen, M. L., Rehman, M., Walther, T. C., Olsen, J. V., and Mann, M. (2009). Lysine acetylation targets protein complexes and co-regulates major cellular functions. Science 325, 834-840.

Clarke, D. M., Maruyama, K., Loo, T. W., Leberer, E., Inesi, G., and MacLennan, D. H. (1989). Functional consequences of glutamate, aspartate, glutamine, and asparagine mutations in the stalk sector of the Ca2+-ATPase of sarcoplasmic reticulum. J Biol Chem 264, 11246-11251.

del Monte, F., Williams, E., Lebeche, D., Schmidt, U., Rosenzweig, A., Gwathmey, J. K., Lewandowski, E. D., and Hajjar, R. J. (2001). Improvement in survival and cardiac metabolism after gene transfer of sarcoplasmic reticulum Ca(2+)-ATPase in a rat model of heart failure. Circulation 104, 1424-1429.

Dremina, E. S., Sharov, V. S., Davies, M. J., and Schoneich, C. (2007). Oxidation and inactivation of SERCA by selective reaction of cysteine residues with amino acid peroxides. Chem Res Toxicol 20, 1462-1469.

French, J. P., Quindry, J. C., Falk, D. J., Staib, J. L., Lee, Y., Wang, K. K., and Powers, S. K. (2006). Ischemia-reperfusion-induced calpain activation and SERCA2a degradation are attenuated by exercise training and calpain inhibition. Am J Physiol Heart Circ Physiol 290, H128-136.

Gwathmey, J. K., Copelas, L., MacKinnon, R., Schoen, F. J., Feldman, M. D., Grossman, W., and Morgan, J. P. (1987). Abnormal intracellular calcium handling in myocardium from patients with end-stage heart failure. Circ Res 61, 70-76.

Gwathmey, J. K., and Hajjar, R. J. (1990). Intracellular calcium related to force development in twitch contraction of mammalian myocardium. Cell Calcium 11, 531-538.

Hajjar, R. J., Schmidt, U., Kang, J. X., Matsui, T., and Rosenzweig, A. (1997). Adenoviral gene transfer of phospholamban in isolated rat cardiomyocytes. Rescue effects by concomitant gene transfer of sarcoplasmic reticulum Ca(2+)-ATPase. Circ Res 81, 145-153.

Ihara, Y., Kageyama, K., and Kondo, T. (2005). Overexpression of calreticulin sensitizes SERCA2a to oxidative stress. Biochem Biophys Res Commun 329, 1343-1349.

Jaski, B. E., Jessup, M. L., Mancini, D. M., Cappola, T. P., Pauly, D. F., Greenberg, B., Borow, K., Dittrich, H., Zsebo, K. M., and Hajjar, R. J. (2009). Calcium upregulation by percutaneous administration of gene therapy in cardiac disease (CUPID Trial), a first-in-human phase ½ clinical trial. J Card Fail 15, 171-181.

Kawase, Y., Ly, H. Q., Prunier, F., Lebeche, D., Shi, Y., Jin, H., Hadri, L., Yoneyama, R., Hoshino, K., Takewa, Y., et al. (2008). Reversal of cardiac dysfunction after long-term expression of SERCA2a by gene transfer in a pre-clinical model of heart failure. J Am Coll Cardiol 51, 1112-1119.

Kim, K. I., and Baek, S. H. (2006). SUMOylation code in cancer development and metastasis. Mol Cells 22, 247-253.

Kim, M. J., Chia, I. V., and Costantini, F. (2008). SUMOylation target sites at the C terminus protect Axin from ubiquitination and confer protein stability. FASEB J 22, 3785-3794.

Knyushko, T. V., Sharov, V. S., Williams, T. D., Schoneich, C., and Bigelow, D. J. (2005). 3-Nitrotyrosine modification of SERCA2a in the aging heart: a distinct signature of the cellular redox environment. Biochemistry 44, 13071-13081.

Lancel, S., Zhang, J., Evangelista, A., Trucillo, M. P., Tong, X., Siwik, D. A., Cohen, R. A., and Colucci, W. S. (2009). Nitroxyl activates SERCA in cardiac myocytes via glutathiolation of cysteine 674. Circ Res 104, 720-723.

MacLennan, D. H., and Kranias, E. G. (2003). Phospholamban: a crucial regulator of cardiac contractility. Nat Rev Mol Cell Biol 4, 566-577.

Meyer, M., Schillinger, W., Pieske, B., Holubarsch, C., Heilmann, C., Posival, H., Kuwajima, G., Mikoshiba, K., Just, H., Hasenfuss, G., et al. (1995). Alterations of sarcoplasmic reticulum proteins in failing human dilated cardiomyopathy. Circulation 92, 778-784.

Minamisawa, S., Hoshijima, M., Chu, G., Ward, C. A., Frank, K., Gu, Y., Martone, M. E., Wang, Y., Ross, J., Jr., Kranias, E. G., et al. (1999). Chronic phospholamban-sarcoplasmic reticulum calcium ATPase interaction is the critical calcium cycling defect in dilated cardiomyopathy. Cell 99, 313-322.

Mooney, S. M., Grande, J. P., Salisbury, J. L., and Janknecht, R. (2010). Sumoylation of p68 and p72 RNA helicases affects protein stability and transactivation potential. Biochemistry 49, 1-10.

Ryu, K. Y., Garza, J. C., Lu, X. Y., Barsh, G. S., and Kopito, R. R. (2008). Hypothalamic neurodegeneration and adult-onset obesity in mice lacking the Ubb polyubiquitin gene. Proc Natl Acad Sci USA 105, 4016-4021.

Sampson, D. A., Wang, M., and Matunis, M. J. (2001). The small ubiquitin-like modifier-1 (SUMO-1) consensus sequence mediates Ubc9 binding and is essential for SUMO-1 modification. J Biol Chem 276, 21664-21669.

Sarge, K. D., and Park-Sarge, O. K. (2009). Sumoylation and human disease pathogenesis. Trends Biochem Sci 34, 200-205.

Schillinger, W., Fiolet, J. W., Schlotthauer, K., and Hasenfuss, G. (2003). Relevance of Na+-Ca2+ exchange in heart failure. Cardiovasc Res 57, 921-933.

Seth, M., Sumbilla, C., Mullen, S. P., Lewis, D., Klein, M. G., Hussain, A., Soboloff, J., Gill, D. L., and Inesi, G. (2004). Sarco(endo)plasmic reticulum Ca2+ ATPase (SERCA) gene silencing and remodeling of the Ca2+ signaling mechanism in cardiac myocytes. Proc Natl Acad Sci USA 101, 16683-16688.

Shishido, T., Woo, C. H., Ding, B., McClain, C., Molina, C. A., Yan, C., Yang, J., and Abe, J. (2008). Effects of MEK5/ERK5 association on small ubiquitin-related modification of ERK5: implications for diabetic ventricular dysfunction after myocardial infarction. Circ Res 102, 1416-1425.

Steffan, J. S., Agrawal, N., Pallos, J., Rockabrand, E., Trotman, L. C., Slepko, N., Illes, K., Lukacsovich, T., Zhu, Y. Z., Cattaneo, E., et al. (2004). SUMO modification of Huntingtin and Huntington's disease pathology. Science 304, 100-104.

Studer, R., Reinecke, H., Bilger, J., Eschenhagen, T., Bohm, M., Hasenfuss, G., Just, H., Holtz, J., and Drexler, H. (1994). Gene expression of the cardiac Na(+)-Ca2+ exchanger in end-stage human heart failure. Circ Res 75, 443-453.

Van Rechem, C., Boulay, G., Pinte, S., Stankovic-Valentin, N., Guerardel, C., and Leprince, D. (2010). Differential regulation of HIC1 target genes by CtBP and NuRD, via an acetylation/SUMOylation switch, in quiescent versus proliferating cells. Mol Cell Biol 30, 4045-4059.

Wang, J., Feng, X. H., and Schwartz, R. J. (2004). SUMO-1 modification activated GATA4-dependent cardiogenic gene activity. J Biol Chem 279, 49091-49098.

Wang, J., Zhang, H., Iyer, D., Feng, X. H., and Schwartz, R. J. (2008). Regulation of cardiac specific nkx2.5 gene activity by small ubiquitin-like modifier. J Biol Chem 283, 23235-23243.

Welchman, R. L., Gordon, C., and Mayer, R. J. (2005). Ubiquitin and ubiquitin-like proteins as multifunctional signals. Nat Rev Mol Cell Biol 6, 599-609.

Woo, C. H., and Abe, J. (2010). SUMO—a post-translational modification with therapeutic potential? Curr Opin Pharmacol 10, 146-155.

Ying, J., Sharov, V., Xu, S., Jiang, B., Gerrity, R., Schoneich, C., and Cohen, R. A. (2008). Cysteine-674 oxidation and degradation of sarcoplasmic reticulum Ca(2+) ATPase in diabetic pig aorta. Free Radic Biol Med 45, 756-762.

Zarain-Herzberg, A., Afzal, N., Elimban, V., and Dhalla, N. S. (1996). Decreased expression of cardiac sarcoplasmic reticulum Ca(2+)-pump ATPase in congestive heart failure due to myocardial infarction. Mol Cell Biochem 163-164, 285-290.

Zhang, Y. Q., and Sarge, K. D. (2008). Sumoylation regulates lamin A function and is lost in lamin A mutants associated with familial cardiomyopathies. J Cell Biol 182, 35-39.

Zhu, K., Zhao, J., Lubman, D. M., Miller, F. R., and Barder, T. J. (2005). Protein pI shifts due to posttranslational modifications in the separation and characterization of proteins. Anal Chem 77, 2745-2755.

From the foregoing it will be appreciated that, although specific embodiments of the invention have been described herein for purposes of illustration, various modifications may be made without deviating from the spirit and scope of the invention.

What is claimed is:

1. A method of treating a cardiac dysfunction in a subject comprising administering a recombinant adeno-associated virus vector comprising an expressible coding region encoding a SUMO1 protein, wherein the coding region is operably linked to at least one expression control element, in a therapeutically effective amount to treat the cardiovascular dysfunction in the subject, wherein the cardiac dysfunction is selected from the group consisting of heart failure, pressure overload-induced cardiac dysfunction, and cardiac dysfunction induced by inhibited calcium decay.

2. The method according to claim 1 wherein the heart failure comprises contractile dysfunction.

3. The method according to claim 1 wherein the heart failure is TAC-induced heart failure.

4. The method according to claim 1 wherein the subject is a human.

5. The method according to claim 1 wherein the recombinant adeno-associated virus is rAAV1.

* * * * *

UNITED STATES PATENT AND TRADEMARK OFFICE
CERTIFICATE OF CORRECTION

PATENT NO. : 10,105,422 B2  
APPLICATION NO. : 15/281269  
DATED : October 23, 2018  
INVENTOR(S) : Roger Joseph Hajjar et al.

Page 1 of 1

It is certified that error appears in the above-identified patent and that said Letters Patent is hereby corrected as shown below:

On the Title Page

At item (60), Under "Related U.S. Application Data", Line 1, "(60)" should be -- (63) --.

At item (60), Under "Related U.S. Application Data", Line 2, "2015," should be -- 2015, now abandoned --.

Signed and Sealed this  
Twenty-first Day of May, 2019

Andrei Iancu  
*Director of the United States Patent and Trademark Office*

```
                        SEQUENCE LISTING

<160> NUMBER OF SEQ ID NOS: 18

<210> SEQ ID NO 1
<211> LENGTH: 4359
<212> TYPE: DNA
<213> ORGANISM: Homo sapiens
<220> FEATURE:
<221> NAME/KEY: misc_feature
<223> OTHER INFORMATION: Human SERCA2a polynucleotide
<220> FEATURE:
<221> NAME/KEY: CDS
<222> LOCATION: (564)..(3557)

<400> SEQUENCE: 1
ggcagcggcc gataaatgct attagagcag ccgccgcgga gccgtccccg acgccacctc      60
cttttccttc gccgcagttt cctccgccgc tgtcgggcgt gcggcgctga gggacccggg     120
cgagcgcgcc gcgcaccgcc ccgccggctc gcctccctcg ccgcgttccg ccctcagtgg     180
tctgccgggc gccccctcct ccggcccggg cggggcctct gatcgcctca agagagcggg     240 gaggggctc ggggggccgcg gcctgccctc ccggcgggcg gctgagggcg agggaggccc     300
tcccttctgg cgaggggagg gagggtgggt caggagcccc caacccgccc tgcggagctc     360
ggggccgcgc gagggcggt tgtctggggg aggggcgcg gggtgattca gcgcccggcg      420
aggcggaagc ggccgcaaga ggaggagggg agagcccgtc cgcgcctggg ctcccggggt     480
ggcacgagcc cgcggccgga gtgcgaggcg gaggcgagga ggccgcgggg acgggaggcg     540
aggccggccg ggcccccgaa gcc atg gag aac gcg cac acc aag acg gtg gag     593
                         Met Glu Asn Ala His Thr Lys Thr Val Glu
                         1               5                   10 gag gtg ctg ggc cac ttc ggc gtc aac gag agt acg ggg ctg agc ctg        641
Glu Val Leu Gly His Phe Gly Val Asn Glu Ser Thr Gly Leu Ser Leu
                15                  20                  25 gaa cag gtc aag aag ctt aag gag aga tgg ggc tcc aac gag tta ccg        689
Glu Gln Val Lys Lys Leu Lys Glu Arg Trp Gly Ser Asn Glu Leu Pro
        30                  35                  40 gct gaa gaa gga aaa acc ttg ctg gaa ctt gtg att gag cag ttt gaa        737
Ala Glu Glu Gly Lys Thr Leu Leu Glu Leu Val Ile Glu Gln Phe Glu
    45                  50                  55 gac ttg cta gtt agg att tta tta ctg gca gca tgt ata tct ttt gtt        785
Asp Leu Leu Val Arg Ile Leu Leu Leu Ala Ala Cys Ile Ser Phe Val
60                  65                  70 ttg gct tgg ttt gaa gaa ggt gaa gaa aca att aca gcc ttt gta gaa        833
Leu Ala Trp Phe Glu Glu Gly Glu Glu Thr Ile Thr Ala Phe Val Glu
```

```
                75                  80                  85                  90
cct ttt gta att tta ctc ata tta gta gcc aat gca att gtg ggt gta       881
Pro Phe Val Ile Leu Leu Ile Leu Val Ala Asn Ala Ile Val Gly Val
                    95                  100                 105 tgg cag gaa aga aat gct gaa aat gcc atc gaa gcc ctt aag gaa tat       929
Trp Gln Glu Arg Asn Ala Glu Asn Ala Ile Glu Ala Leu Lys Glu Tyr
                110                 115                 120 gag cct gaa atg ggc aaa gtg tat cga cag gac aga aag agt gtg cag       977
Glu Pro Glu Met Gly Lys Val Tyr Arg Gln Asp Arg Lys Ser Val Gln
                125                 130                 135 cgg att aaa gct aaa gac ata gtt cct ggt gat att gta gaa att gct      1025
Arg Ile Lys Ala Lys Asp Ile Val Pro Gly Asp Ile Val Glu Ile Ala
        140                 145                 150 gtt ggt gac aaa gtt cct gct gat ata agg tta act tcc atc aaa tct      1073
Val Gly Asp Lys Val Pro Ala Asp Ile Arg Leu Thr Ser Ile Lys Ser
155                 160                 165                 170 acc aca cta aga gtt gac cag tca att ctc aca ggt gaa tct gtc tct      1121
Thr Thr Leu Arg Val Asp Gln Ser Ile Leu Thr Gly Glu Ser Val Ser
                    175                 180                 185 gtc atc aag cac act gat ccc gtc cct gac cca cga gct gtc aac caa      1169
Val Ile Lys His Thr Asp Pro Val Pro Asp Pro Arg Ala Val Asn Gln
                190                 195                 200 gat aaa aag aac atg ctg ttt tct ggt aca aac att gct gct ggg aaa      1217
Asp Lys Lys Asn Met Leu Phe Ser Gly Thr Asn Ile Ala Ala Gly Lys
                205                 210                 215 gct atg gga gtg gtg gta gca act gga gtt aac acc gaa att ggc aag      1265
Ala Met Gly Val Val Val Ala Thr Gly Val Asn Thr Glu Ile Gly Lys
        220                 225                 230 atc cgg gat gaa atg gtg gca aca gaa cag gag aga aca ccc ctt cag      1313
Ile Arg Asp Glu Met Val Ala Thr Glu Gln Glu Arg Thr Pro Leu Gln
235                 240                 245                 250 caa aaa cta gat gaa ttt ggg gaa cag ctt tcc aaa gtc atc tcc ctt      1361
Gln Lys Leu Asp Glu Phe Gly Glu Gln Leu Ser Lys Val Ile Ser Leu
                    255                 260                 265 att tgc att gca gtc tgg atc ata aat att ggg cac ttc aat gac ccg      1409
Ile Cys Ile Ala Val Trp Ile Ile Asn Ile Gly His Phe Asn Asp Pro
                270                 275                 280 gtt cat gga ggg tcc tgg atc aga ggt gct att tac tac ttt aaa att      1457
Val His Gly Gly Ser Trp Ile Arg Gly Ala Ile Tyr Tyr Phe Lys Ile
                285                 290                 295 gca gtg gcc ctg gct gta gca gcc att cct gaa ggt ctg cct gca gtc      1505
Ala Val Ala Leu Ala Val Ala Ala Ile Pro Glu Gly Leu Pro Ala Val
        300                 305                 310 atc acc acc tgc ctg gct ctt gga act cgc aga atg gca aag aaa aat      1553
Ile Thr Thr Cys Leu Ala Leu Gly Thr Arg Arg Met Ala Lys Lys Asn
315                 320                 325                 330 gcc att gtt cga agc ctc ccg tct gtg gaa acc ctt ggt tgt act tct      1601
Ala Ile Val Arg Ser Leu Pro Ser Val Glu Thr Leu Gly Cys Thr Ser
                    335                 340                 345 gtt atc tgc tca gac aag act ggt aca ctt aca aca aac cag atg tca      1649
Val Ile Cys Ser Asp Lys Thr Gly Thr Leu Thr Thr Asn Gln Met Ser
                350                 355                 360 gtc tgc agg atg ttc att ctg gac aga gtg gaa ggt gat act tgt tcc      1697
Val Cys Arg Met Phe Ile Leu Asp Arg Val Glu Gly Asp Thr Cys Ser
                365                 370                 375 ctt aat gag ttt acc ata act gga tca act tat gca cct att gga gaa      1745
Leu Asn Glu Phe Thr Ile Thr Gly Ser Thr Tyr Ala Pro Ile Gly Glu
        380                 385                 390 gtg cat aaa gat gat aaa cca gtg aat tgt cac cag tat gat ggt ctg      1793
```

-continued

| | |
|---|---|
| Val His Lys Asp Asp Lys Pro Val Asn Cys His Gln Tyr Asp Gly Leu<br>395                     400                           405                       410 | |
| gta gaa tta gca aca att tgt gct ctt tgt aat gac tct gct ttg gat<br>Val Glu Leu Ala Thr Ile Cys Ala Leu Cys Asn Asp Ser Ala Leu Asp<br>                       415                     420                   425 | 1841 |
| tac aat gag gca aag ggt gtg tat gaa aaa gtt gga gaa gct aca gag<br>Tyr Asn Glu Ala Lys Gly Val Tyr Glu Lys Val Gly Glu Ala Thr Glu<br>            430                     435                     440 | 1889 |
| act gct ctc act tgc cta gta gag aag atg aat gta ttt gat acc gaa<br>Thr Ala Leu Thr Cys Leu Val Glu Lys Met Asn Val Phe Asp Thr Glu<br>            445                     450                    455 | 1937 |
| ttg aag ggt ctt tct aaa ata gaa cgt gca aat gcc tgc aac tca gtc<br>Leu Lys Gly Leu Ser Lys Ile Glu Arg Ala Asn Ala Cys Asn Ser Val<br>460                     465                     470 | 1985 |
| att aaa cag ctg atg aaa aag gaa ttc act cta gag ttt tca cgt gac<br>Ile Lys Gln Leu Met Lys Lys Glu Phe Thr Leu Glu Phe Ser Arg Asp<br>475                     480                     485                   490 | 2033 |
| aga aag tca atg tcg gtt tac tgt aca cca aat aaa cca agc agg aca<br>Arg Lys Ser Met Ser Val Tyr Cys Thr Pro Asn Lys Pro Ser Arg Thr<br>                     495                     500                     505 | 2081 |
| tca atg agc aag atg ttt gtg aag ggt gct cct gaa ggt gtc att gac<br>Ser Met Ser Lys Met Phe Val Lys Gly Ala Pro Glu Gly Val Ile Asp<br>            510                     515                    520 | 2129 |
| agg tgc acc cac att cga gtt gga agt act aag gtt cct atg acc tct<br>Arg Cys Thr His Ile Arg Val Gly Ser Thr Lys Val Pro Met Thr Ser<br>               525                     530                    535 | 2177 |
| gga gtc aaa cag aag atc atg tct gtc att cga gag tgg ggt agt ggc<br>Gly Val Lys Gln Lys Ile Met Ser Val Ile Arg Glu Trp Gly Ser Gly<br>540                     545                     550 | 2225 |
| agc gac aca ctg cga tgc ctg gcc ctg gcc act cat gac aac cca ctg<br>Ser Asp Thr Leu Arg Cys Leu Ala Leu Ala Thr His Asp Asn Pro Leu<br>555                     560                     565                    570 | 2273 |
| aga aga gaa gaa atg cac ctt gag gac tct gcc aac ttt att aaa tat<br>Arg Arg Glu Glu Met His Leu Glu Asp Ser Ala Asn Phe Ile Lys Tyr<br>               575                     580                    585 | 2321 |
| gag acc aat ctg acc ttc gtt ggc tgc gtg ggc atg ctg gat cct ccg<br>Glu Thr Asn Leu Thr Phe Val Gly Cys Val Gly Met Leu Asp Pro Pro<br>                     590                     595                    600 | 2369 |
| aga atc gag gtg gcc tcc tcc gtg aag ctg tgc cgg caa gca ggc atc<br>Arg Ile Glu Val Ala Ser Ser Val Lys Leu Cys Arg Gln Ala Gly Ile<br>            605                     610                    615 | 2417 |
| cgg gtc atc atg atc act ggg gac aac aag ggc act gct gtg gcc atc<br>Arg Val Ile Met Ile Thr Gly Asp Asn Lys Gly Thr Ala Val Ala Ile<br>620                     625                     630 | 2465 |
| tgt cgc cgc atc ggc atc ttc ggg cag gat gag gac gtg acg tca aaa<br>Cys Arg Arg Ile Gly Ile Phe Gly Gln Asp Glu Asp Val Thr Ser Lys<br>635                     640                     645                    650 | 2513 |
| gct ttc aca ggc cgg gag ttt gat gaa ctc aac ccc tcc gcc cag cga<br>Ala Phe Thr Gly Arg Glu Phe Asp Glu Leu Asn Pro Ser Ala Gln Arg<br>               655                     660                    665 | 2561 |
| gac gcc tgc ctg aac gcc cgc tgt ttt gct cga gtt gaa ccc tcc cac<br>Asp Ala Cys Leu Asn Ala Arg Cys Phe Ala Arg Val Glu Pro Ser His<br>            670                     675                    680 | 2609 |
| aag tct aaa atc gta gaa ttt ctt cag tct ttt gat gag att aca gct<br>Lys Ser Lys Ile Val Glu Phe Leu Gln Ser Phe Asp Glu Ile Thr Ala<br>685                     690                     695 | 2657 |
| atg act ggc gat ggc gtg aac gat gct cct gct ctg aag aaa gcc gag<br>Met Thr Gly Asp Gly Val Asn Asp Ala Pro Ala Leu Lys Lys Ala Glu<br>700                     705                     710 | 2705 |

| | |
|---|---|
| att ggc att gct atg ggc tct ggc act gcg gtg gct aaa acc gcc tct<br>Ile Gly Ile Ala Met Gly Ser Gly Thr Ala Val Ala Lys Thr Ala Ser<br>715                     720                 725               730 | 2753 |
| gag atg gtc ctg gcg gat gac aac ttc tcc acc att gtg gct gcc gtt<br>Glu Met Val Leu Ala Asp Asp Asn Phe Ser Thr Ile Val Ala Ala Val<br>               735                 740                 745 | 2801 |
| gag gag ggg cgg gca atc tac aac aac atg aaa cag ttc atc cgc tac<br>Glu Glu Gly Arg Ala Ile Tyr Asn Asn Met Lys Gln Phe Ile Arg Tyr<br>750                     755                 760 | 2849 |
| ctc atc tcg tcc aac gtc ggg gaa gtt gtc tgt att ttc ctg aca gca<br>Leu Ile Ser Ser Asn Val Gly Glu Val Val Cys Ile Phe Leu Thr Ala<br>          765                 770                 775 | 2897 |
| gcc ctt gga ttt ccc gag gct ttg att cct gtt cag ctg ctc tgg gtc<br>Ala Leu Gly Phe Pro Glu Ala Leu Ile Pro Val Gln Leu Leu Trp Val<br>780                     785                 790 | 2945 |
| aat ctg gtg aca gat ggc ctg cct gcc act gca ctg ggg ttc aac cct<br>Asn Leu Val Thr Asp Gly Leu Pro Ala Thr Ala Leu Gly Phe Asn Pro<br>795                     800                 805               810 | 2993 |
| cct gat ctg gac atc atg aat aaa cct ccc cgg aac cca aag gaa cca<br>Pro Asp Leu Asp Ile Met Asn Lys Pro Pro Arg Asn Pro Lys Glu Pro<br>               815                 820                 825 | 3041 |
| ttg atc agc ggg tgg ctc ttt ttc cgt tac ttg gct att ggc tgt tac<br>Leu Ile Ser Gly Trp Leu Phe Phe Arg Tyr Leu Ala Ile Gly Cys Tyr<br>          830                 835                 840 | 3089 |
| gtc ggc gct gct acc gtg ggt gct gct gca tgg tgg ttc att gct gct<br>Val Gly Ala Ala Thr Val Gly Ala Ala Ala Trp Trp Phe Ile Ala Ala<br>845                     850                 855 | 3137 |
| gac ggt ggt cca aga gtg tcc ttc tac cag ctg agt cat ttc cta cag<br>Asp Gly Gly Pro Arg Val Ser Phe Tyr Gln Leu Ser His Phe Leu Gln<br>         860                 865                 870 | 3185 |
| tgt aaa gag gac aac ccg gac ttt gaa ggc gtg gat tgt gca atc ttt<br>Cys Lys Glu Asp Asn Pro Asp Phe Glu Gly Val Asp Cys Ala Ile Phe<br>875                     880                 885               890 | 3233 |
| gaa tcc cca tac ccg atg aca atg gcg ctc tct gtt cta gta act ata<br>Glu Ser Pro Tyr Pro Met Thr Met Ala Leu Ser Val Leu Val Thr Ile<br>               895                 900                 905 | 3281 |
| gaa atg tgt aac gcc ctc aac agc ttg tcc gaa aac cag tcc ttg ctg<br>Glu Met Cys Asn Ala Leu Asn Ser Leu Ser Glu Asn Gln Ser Leu Leu<br>          910                 915                 920 | 3329 |
| agg atg ccc ccc tgg gag aac atc tgg ctc gtg ggc tcc atc tgc ctg<br>Arg Met Pro Pro Trp Glu Asn Ile Trp Leu Val Gly Ser Ile Cys Leu<br>         925                 930                 935 | 3377 |
| tcc atg tca ctc cac ttc ctg atc ctc tat gtc gaa ccc ttg cca ctc<br>Ser Met Ser Leu His Phe Leu Ile Leu Tyr Val Glu Pro Leu Pro Leu<br>940                     945                 950 | 3425 |
| atc ttc cag atc aca ccg ctg aac gtg acc cag tgg ctg atg gtg ctg<br>Ile Phe Gln Ile Thr Pro Leu Asn Val Thr Gln Trp Leu Met Val Leu<br>955                     960                 965               970 | 3473 |
| aaa atc tcc ttg ccc gtg att ctc atg gat gag acg ctc aag ttt gtg<br>Lys Ile Ser Leu Pro Val Ile Leu Met Asp Glu Thr Leu Lys Phe Val<br>               975                 980                 985 | 3521 |
| gcc cgc aac tac ctg gaa cct gca ata ctg gag taa ccgcttccta<br>Ala Arg Asn Tyr Leu Glu Pro Ala Ile Leu Glu<br>         990                 995 | 3567 |
| aaccattttg cagaaatgta agggtgttcg gttgcgtgca tgtgcgtttt tagcaacaca | 3627 |
| tctaccaacc ctgtgcatga ctgatgttgg ggaaaaagaa agtaaaaaaa cttcccaact | 3687 |
| cactttgtgt tatgtggagg aaatgtgtat taccaatggg gttgttagct tttaaatcaa | 3747 |
| aatactgatt acagatgtac aatttagctt aatcagaaag cctctccaga gaagtttggt | 3807 |

```
ttctttgctg caagaggaat gaggctctgt aaccttatct aagaacttgg aagccgtcag    3867
ccaagtcgcc acatttctct gcaaaatgtc atagcttata taaatgtaca gtattcaatt    3927
gtaatgcatg ccttcggttg taagtagcca gatccctctc cagtgacatt ggaacatgct    3987 acttttaat tggccctgta cagtttgctt atttataaat tcattaaaaa cactacaggt     4047
gttgaatggt taaatgtag gcctccagtt catttcagt tattttctga gtgtgcagac      4107
agctatttcg cactgtatta aatgtaactt atttaatgaa atcagaagca gtagacagat    4167
gttggtgcaa tacaaatatt gtgatgcatt tatcttaata aaatgctaaa tgtcaattta    4227
tcactgcgca tgtttgactt tagactgtaa atagagatca gtttgtttct ttctgtgctg    4287
gtaacaatga gcgtcgcaca gacatggttt caggtaaata aatctattct atgataaaaa    4347
aaaaaaaaaa aa                                                        4359
```

<210> SEQ ID NO 2
<211> LENGTH: 997
<212> TYPE: PRT
<213> ORGANISM: Homo sapiens

<400> SEQUENCE: 2

```
Met Glu Asn Ala His Thr Lys Thr Val Glu Glu Val Leu Gly His Phe
1               5                   10                  15

Gly Val Asn Glu Ser Thr Gly Leu Ser Leu Glu Gln Val Lys Lys Leu
            20                  25                  30

Lys Glu Arg Trp Gly Ser Asn Glu Leu Pro Ala Glu Glu Gly Lys Thr
        35                  40                  45

Leu Leu Glu Leu Val Ile Glu Gln Phe Glu Asp Leu Leu Val Arg Ile
    50                  55                  60

Leu Leu Leu Ala Ala Cys Ile Ser Phe Val Leu Ala Trp Phe Glu Glu
65                  70                  75                  80

Gly Glu Glu Thr Ile Thr Ala Phe Val Glu Pro Phe Val Ile Leu Leu
                85                  90                  95

Ile Leu Val Ala Asn Ala Ile Val Gly Val Trp Gln Glu Arg Asn Ala
            100                 105                 110

Glu Asn Ala Ile Glu Ala Leu Lys Glu Tyr Glu Pro Glu Met Gly Lys
        115                 120                 125

Val Tyr Arg Gln Asp Arg Lys Ser Val Gln Arg Ile Lys Ala Lys Asp
    130                 135                 140

Ile Val Pro Gly Asp Ile Val Glu Ile Ala Val Gly Asp Lys Val Pro
145                 150                 155                 160

Ala Asp Ile Arg Leu Thr Ser Ile Lys Ser Thr Thr Leu Arg Val Asp
                165                 170                 175

Gln Ser Ile Leu Thr Gly Glu Ser Ser Val Ile Lys His Thr Asp
            180                 185                 190

Pro Val Pro Asp Pro Arg Ala Val Asn Gln Asp Lys Lys Asn Met Leu
        195                 200                 205

Phe Ser Gly Thr Asn Ile Ala Ala Gly Lys Ala Met Gly Val Val Val
    210                 215                 220

Ala Thr Gly Val Asn Thr Glu Ile Gly Lys Ile Arg Asp Glu Met Val
225                 230                 235                 240

Ala Thr Glu Gln Glu Arg Thr Pro Leu Gln Gln Lys Leu Asp Glu Phe
                245                 250                 255

Gly Glu Gln Leu Ser Lys Val Ile Ser Leu Ile Cys Ile Ala Val Trp
            260                 265                 270
```

-continued

```
Ile Ile Asn Ile Gly His Phe Asn Asp Pro Val His Gly Gly Ser Trp
        275                 280                 285
Ile Arg Gly Ala Ile Tyr Tyr Phe Lys Ile Ala Val Ala Leu Ala Val
        290                 295                 300
Ala Ala Ile Pro Glu Gly Leu Pro Ala Val Ile Thr Thr Cys Leu Ala
305                 310                 315                 320
Leu Gly Thr Arg Arg Met Ala Lys Lys Asn Ala Ile Val Arg Ser Leu
                325                 330                 335
Pro Ser Val Glu Thr Leu Gly Cys Thr Ser Val Ile Cys Ser Asp Lys
                340                 345                 350
Thr Gly Thr Leu Thr Thr Asn Gln Met Ser Val Cys Arg Met Phe Ile
                355                 360                 365
Leu Asp Arg Val Glu Gly Asp Thr Cys Ser Leu Asn Glu Phe Thr Ile
        370                 375                 380
Thr Gly Ser Thr Tyr Ala Pro Ile Gly Glu Val His Lys Asp Asp Lys
385                 390                 395                 400
Pro Val Asn Cys His Gln Tyr Asp Gly Leu Val Glu Leu Ala Thr Ile
                405                 410                 415
Cys Ala Leu Cys Asn Asp Ser Ala Leu Asp Tyr Asn Glu Ala Lys Gly
                420                 425                 430
Val Tyr Glu Lys Val Gly Glu Ala Thr Glu Thr Ala Leu Thr Cys Leu
                435                 440                 445
Val Glu Lys Met Asn Val Phe Asp Thr Glu Leu Lys Gly Leu Ser Lys
        450                 455                 460
Ile Glu Arg Ala Asn Ala Cys Asn Ser Val Ile Lys Gln Leu Met Lys
465                 470                 475                 480
Lys Glu Phe Thr Leu Glu Phe Ser Arg Asp Arg Lys Ser Met Ser Val
                485                 490                 495
Tyr Cys Thr Pro Asn Lys Pro Ser Arg Thr Ser Met Ser Lys Met Phe
                500                 505                 510
Val Lys Gly Ala Pro Glu Gly Val Ile Asp Arg Cys Thr His Ile Arg
        515                 520                 525
Val Gly Ser Thr Lys Val Pro Met Thr Ser Gly Val Lys Gln Lys Ile
        530                 535                 540
Met Ser Val Ile Arg Glu Trp Gly Ser Gly Ser Asp Thr Leu Arg Cys
545                 550                 555                 560
Leu Ala Leu Ala Thr His Asp Asn Pro Leu Arg Arg Glu Glu Met His
                565                 570                 575
Leu Glu Asp Ser Ala Asn Phe Ile Lys Tyr Glu Thr Asn Leu Thr Phe
                580                 585                 590
Val Gly Cys Val Gly Met Leu Asp Pro Pro Arg Ile Glu Val Ala Ser
        595                 600                 605
Ser Val Lys Leu Cys Arg Gln Ala Gly Ile Arg Val Ile Met Ile Thr
        610                 615                 620
Gly Asp Asn Lys Gly Thr Ala Val Ala Ile Cys Arg Arg Ile Gly Ile
625                 630                 635                 640
Phe Gly Gln Asp Glu Asp Val Thr Ser Lys Ala Phe Thr Gly Arg Glu
                645                 650                 655
Phe Asp Glu Leu Asn Pro Ser Ala Gln Arg Asp Ala Cys Leu Asn Ala
                660                 665                 670
Arg Cys Phe Ala Arg Val Glu Pro Ser His Lys Ser Lys Ile Val Glu
                675                 680                 685
```

```
Phe Leu Gln Ser Phe Asp Glu Ile Thr Ala Met Thr Gly Asp Gly Val
    690                 695                 700

Asn Asp Ala Pro Ala Leu Lys Lys Ala Glu Ile Gly Ile Ala Met Gly
705                 710                 715                 720

Ser Gly Thr Ala Val Ala Lys Thr Ala Ser Glu Met Val Leu Ala Asp
                725                 730                 735

Asp Asn Phe Ser Thr Ile Val Ala Ala Val Glu Glu Gly Arg Ala Ile
            740                 745                 750

Tyr Asn Asn Met Lys Gln Phe Ile Arg Tyr Leu Ile Ser Ser Asn Val
        755                 760                 765

Gly Glu Val Val Cys Ile Phe Leu Thr Ala Ala Leu Gly Phe Pro Glu
    770                 775                 780

Ala Leu Ile Pro Val Gln Leu Leu Trp Val Asn Leu Val Thr Asp Gly
785                 790                 795                 800

Leu Pro Ala Thr Ala Leu Gly Phe Asn Pro Pro Asp Leu Asp Ile Met
                805                 810                 815

Asn Lys Pro Pro Arg Asn Pro Lys Glu Pro Leu Ile Ser Gly Trp Leu
            820                 825                 830

Phe Phe Arg Tyr Leu Ala Ile Gly Cys Tyr Val Gly Ala Ala Thr Val
        835                 840                 845

Gly Ala Ala Trp Trp Phe Ile Ala Asp Gly Gly Pro Arg Val
    850                 855                 860

Ser Phe Tyr Gln Leu Ser His Phe Leu Gln Cys Lys Glu Asp Asn Pro
865                 870                 875                 880

Asp Phe Glu Gly Val Asp Cys Ala Ile Phe Glu Ser Pro Tyr Pro Met
                885                 890                 895

Thr Met Ala Leu Ser Val Leu Val Thr Ile Glu Met Cys Asn Ala Leu
            900                 905                 910

Asn Ser Leu Ser Glu Asn Gln Ser Leu Leu Arg Met Pro Pro Trp Glu
        915                 920                 925

Asn Ile Trp Leu Val Gly Ser Ile Cys Leu Ser Met Ser Leu His Phe
    930                 935                 940

Leu Ile Leu Tyr Val Glu Pro Leu Pro Leu Ile Phe Gln Ile Thr Pro
945                 950                 955                 960

Leu Asn Val Thr Gln Trp Leu Met Val Leu Lys Ile Ser Leu Pro Val
                965                 970                 975

Ile Leu Met Asp Glu Thr Leu Lys Phe Val Ala Arg Asn Tyr Leu Glu
            980                 985                 990

Pro Ala Ile Leu Glu
        995

<210> SEQ ID NO 3
<211> LENGTH: 3795
<212> TYPE: DNA
<213> ORGANISM: Sus scrofa
<220> FEATURE:
<221> NAME/KEY: misc_feature
<223> OTHER INFORMATION: Pig SERCA2a polynucleotide
<220> FEATURE:
<221> NAME/KEY: CDS
<222> LOCATION: (14)..(3007)

<400> SEQUENCE: 3
ggcccccgca gcc atg gag aac gcg cac aca aag acg gtg gag gag gtg      49
            Met Glu Asn Ala His Thr Lys Thr Val Glu Glu Val
              1               5                  10 ctg ggc cac ttc ggc gtc aac gag agc acg ggg ctg agc ctg gag cag    97
```

-continued

```
Leu Gly His Phe Gly Val Asn Glu Ser Thr Gly Leu Ser Leu Glu Gln
         15                  20                  25 gtc aag aag ctc aag gag aga tgg ggc tcc aac gag tta ccg gct gaa    145
Val Lys Lys Leu Lys Glu Arg Trp Gly Ser Asn Glu Leu Pro Ala Glu
         30                  35                  40 gaa ggg aaa acc ttg ctg gaa ctt gtg att gag cag ttt gaa gac tta    193
Glu Gly Lys Thr Leu Leu Glu Leu Val Ile Glu Gln Phe Glu Asp Leu
 45                  50                  55                  60 ctc gtt aga att tta ttg ttg gca gca tgt ata tct ttt gtt ttg gct    241
Leu Val Arg Ile Leu Leu Leu Ala Ala Cys Ile Ser Phe Val Leu Ala
                 65                  70                  75 tgg ttt gaa gaa ggc gaa gaa aca att aca gcc ttt gta gaa ccc ttt    289
Trp Phe Glu Glu Gly Glu Glu Thr Ile Thr Ala Phe Val Glu Pro Phe
             80                  85                  90 gta att tta ctt ata tta gta gcc aat gca att gtg ggt gta tgg cag    337
Val Ile Leu Leu Ile Leu Val Ala Asn Ala Ile Val Gly Val Trp Gln
         95                 100                 105 gaa agg aat gca gaa aat gcc atc gaa gcc ctt aag gag tat gag cct    385
Glu Arg Asn Ala Glu Asn Ala Ile Glu Ala Leu Lys Glu Tyr Glu Pro
    110                 115                 120 gaa atg ggc aaa gtg tat cga cag gac agg aag agt gta caa cga att    433
Glu Met Gly Lys Val Tyr Arg Gln Asp Arg Lys Ser Val Gln Arg Ile
125                 130                 135                 140 aaa gct aaa gac ata gtt cct ggt gat att gta gaa att gct gtt ggt    481
Lys Ala Lys Asp Ile Val Pro Gly Asp Ile Val Glu Ile Ala Val Gly
                145                 150                 155 gac aaa gtt cct gct gat ata aga tta acg tcc atc aaa tct act act    529
Asp Lys Val Pro Ala Asp Ile Arg Leu Thr Ser Ile Lys Ser Thr Thr
            160                 165                 170 cta aga gtt gac cag tca att ctc aca ggt gag tct gtc tct gtc atc    577
Leu Arg Val Asp Gln Ser Ile Leu Thr Gly Glu Ser Val Ser Val Ile
        175                 180                 185 aag cac acc gac cct gtc cct gac cca cgg gct gtc aac caa gat aag    625
Lys His Thr Asp Pro Val Pro Asp Pro Arg Ala Val Asn Gln Asp Lys
    190                 195                 200 aag aac atg ctc ttt tct ggt aca aac ata gca gct ggc aaa gcc atg    673
Lys Asn Met Leu Phe Ser Gly Thr Asn Ile Ala Ala Gly Lys Ala Met
205                 210                 215                 220 gga gtg gtg gtg gca act gga gtt aac act gaa att ggc aag atc cgg    721
Gly Val Val Val Ala Thr Gly Val Asn Thr Glu Ile Gly Lys Ile Arg
                225                 230                 235 gat gaa atg gta gca acg gaa cag gag aga aca ccc ctc cag cag aaa    769
Asp Glu Met Val Ala Thr Glu Gln Glu Arg Thr Pro Leu Gln Gln Lys
            240                 245                 250 cta gat gag ttt ggg gaa cag ctt tcc aaa gtc atc tcc ctt att tgc    817
Leu Asp Glu Phe Gly Glu Gln Leu Ser Lys Val Ile Ser Leu Ile Cys
        255                 260                 265 att gca gtc tgg atc ata aac att ggg cac ttc aat gac ccg gtt cat    865
Ile Ala Val Trp Ile Ile Asn Ile Gly His Phe Asn Asp Pro Val His
    270                 275                 280 gga ggc tcc tgg atc aga ggt gct att tat tac ttt aaa att gca gtg    913
Gly Gly Ser Trp Ile Arg Gly Ala Ile Tyr Tyr Phe Lys Ile Ala Val
285                 290                 295                 300 gcc ctg gct gta gca gcc att cct gaa ggc ctg cct gct gtc att acc    961
Ala Leu Ala Val Ala Ala Ile Pro Glu Gly Leu Pro Ala Val Ile Thr
                305                 310                 315 acc tgc ctg gct ctt gga act cgt aga atg gca aag aaa aat gcc att   1009
Thr Cys Leu Ala Leu Gly Thr Arg Arg Met Ala Lys Lys Asn Ala Ile
        320                 325                 330
```

-continued

```
gtt cga agt ctc cct tct gtg gaa acc ctt ggt tgc act tcc gtt atc      1057
Val Arg Ser Leu Pro Ser Val Glu Thr Leu Gly Cys Thr Ser Val Ile
        335                 340                 345 tgc tca gac aag act ggt aca ctt aca aca aac cag atg tca gtc tgc      1105
Cys Ser Asp Lys Thr Gly Thr Leu Thr Thr Asn Gln Met Ser Val Cys
350                 355                 360 agg atg ttc att ctg gac aaa gtt gaa ggt gat act tgt tcc ctg aat      1153
Arg Met Phe Ile Leu Asp Lys Val Glu Gly Asp Thr Cys Ser Leu Asn
365                 370                 375                 380 gag ttt acc ata act gga tca aca tat gct cct att gga gaa gtc cat      1201
Glu Phe Thr Ile Thr Gly Ser Thr Tyr Ala Pro Ile Gly Glu Val His
                385                 390                 395 aaa gat gat aaa cca gta aag tgt cat caa tat gat ggt ctt gtg gaa      1249
Lys Asp Asp Lys Pro Val Lys Cys His Gln Tyr Asp Gly Leu Val Glu
            400                 405                 410 ttg gca aca att tgt gct ctc tgt aat gac tct gct ttg gat tac aat      1297
Leu Ala Thr Ile Cys Ala Leu Cys Asn Asp Ser Ala Leu Asp Tyr Asn
        415                 420                 425 gag gca aag ggt gtg tat gaa aaa gtt gga gaa gct aca gag act gct      1345
Glu Ala Lys Gly Val Tyr Glu Lys Val Gly Glu Ala Thr Glu Thr Ala
    430                 435                 440 ctc act tgc ctg gta gag aag atg aat gtc ttt gat act gag tta aag      1393
Leu Thr Cys Leu Val Glu Lys Met Asn Val Phe Asp Thr Glu Leu Lys
445                 450                 455                 460 ggt ctt tct aaa ata gaa cga gca aat gcc tgc aac tcg gtc att aaa      1441
Gly Leu Ser Lys Ile Glu Arg Ala Asn Ala Cys Asn Ser Val Ile Lys
                465                 470                 475 caa ttg atg aaa aag gaa ttt act cta gag ttt tca cgt gat aga aaa      1489
Gln Leu Met Lys Lys Glu Phe Thr Leu Glu Phe Ser Arg Asp Arg Lys
            480                 485                 490 tca atg tca gtt tat tgt aca cca aac aaa cca agc cgg aca tcg atg      1537
Ser Met Ser Val Tyr Cys Thr Pro Asn Lys Pro Ser Arg Thr Ser Met
        495                 500                 505 agc aaa atg ttt gtg aag ggt gct ccc gaa ggt gtc att gac agg tgt      1585
Ser Lys Met Phe Val Lys Gly Ala Pro Glu Gly Val Ile Asp Arg Cys
    510                 515                 520 acc cac att cga gtt gga agt act aaa gtc ccc atg act cct ggc gtc      1633
Thr His Ile Arg Val Gly Ser Thr Lys Val Pro Met Thr Pro Gly Val
525                 530                 535                 540 aaa cag aag atc atg tct gtc att cgg gaa tgg ggc agt ggc agc gac      1681
Lys Gln Lys Ile Met Ser Val Ile Arg Glu Trp Gly Ser Gly Ser Asp
                545                 550                 555 aca ctg cga tgc ctg gct ctg gcc act cat gac aac ccg atg aga aga      1729
Thr Leu Arg Cys Leu Ala Leu Ala Thr His Asp Asn Pro Met Arg Arg
            560                 565                 570 gaa gaa atg aac ctt gag gat tct gcc aac ttt att aaa tac gag acc      1777
Glu Glu Met Asn Leu Glu Asp Ser Ala Asn Phe Ile Lys Tyr Glu Thr
        575                 580                 585 aat ctg act ttc gtt ggc tgt gtg ggc atg ctg gac cct cca aga atc      1825
Asn Leu Thr Phe Val Gly Cys Val Gly Met Leu Asp Pro Pro Arg Ile
    590                 595                 600 gaa gtg gcc tcc tct gtg aag ctg tgc cgg cag gca ggc atc cgg gtc      1873
Glu Val Ala Ser Ser Val Lys Leu Cys Arg Gln Ala Gly Ile Arg Val
605                 610                 615                 620 att atg atc aca ggc gac aac aag ggt acc gct gtg gcc atc tgc cgt      1921
Ile Met Ile Thr Gly Asp Asn Lys Gly Thr Ala Val Ala Ile Cys Arg
                625                 630                 635 cgc att ggc atc ttt ggg cag gac gag gat gtg acg tca aag gct ttt      1969
Arg Ile Gly Ile Phe Gly Gln Asp Glu Asp Val Thr Ser Lys Ala Phe
            640                 645                 650
```

-continued

```
aca ggt cgg gag ttt gat gag ctc aat cct tca gcc cag aga gaa gcc    2017
Thr Gly Arg Glu Phe Asp Glu Leu Asn Pro Ser Ala Gln Arg Glu Ala
            655                 660                 665 tgc ctg aat gcc cgc tgt ttc gct cga gtt gaa cct tcc cac aag tct    2065
Cys Leu Asn Ala Arg Cys Phe Ala Arg Val Glu Pro Ser His Lys Ser
670                 675                 680 aaa att gta gaa ttt ctt cag tct ttt gat gag att aca gct atg act    2113
Lys Ile Val Glu Phe Leu Gln Ser Phe Asp Glu Ile Thr Ala Met Thr
685                 690                 695                 700 ggg gac ggt gtg aat gat gct cct gct ctg aag aag tct gag atc ggc    2161
Gly Asp Gly Val Asn Asp Ala Pro Ala Leu Lys Lys Ser Glu Ile Gly
                705                 710                 715 att gcc atg ggc tct ggc acc gcg gtg gct aaa act gcc tcc gag atg    2209
Ile Ala Met Gly Ser Gly Thr Ala Val Ala Lys Thr Ala Ser Glu Met
            720                 725                 730 gtc ctg gct gat gac aac ttc tcc acc att gtg gct gct gtg gag gag    2257
Val Leu Ala Asp Asp Asn Phe Ser Thr Ile Val Ala Ala Val Glu Glu
            735                 740                 745 gga cgg gca ata tac aac aac atg aag cag ttc att cgc tac ctc atc    2305
Gly Arg Ala Ile Tyr Asn Asn Met Lys Gln Phe Ile Arg Tyr Leu Ile
        750                 755                 760 tcg tcc aac gtg gga gaa gtt gtc tgt att ttc ctg aca gca gcc ctt    2353
Ser Ser Asn Val Gly Glu Val Val Cys Ile Phe Leu Thr Ala Ala Leu
765                 770                 775                 780 gga ttt cct gag gct tta att cct gtc cag ctg ctc tgg gtc aat ctg    2401
Gly Phe Pro Glu Ala Leu Ile Pro Val Gln Leu Leu Trp Val Asn Leu
                785                 790                 795 gtg aca gat ggc ctg cct gcc act gca ctg ggg ttc aat cct cct gat    2449
Val Thr Asp Gly Leu Pro Ala Thr Ala Leu Gly Phe Asn Pro Pro Asp
            800                 805                 810 ctg gac att atg aac aaa cca ccc cgg aac cca aag gaa cca ctg atc    2497
Leu Asp Ile Met Asn Lys Pro Pro Arg Asn Pro Lys Glu Pro Leu Ile
            815                 820                 825 agt ggg tgg ctc ttt ttc cgc tac ctg gct att ggc tgt tac gtt ggt    2545
Ser Gly Trp Leu Phe Phe Arg Tyr Leu Ala Ile Gly Cys Tyr Val Gly
830                 835                 840 gct gct act gtg ggt gct gct gcg tgg tgg ttc att gct gcc gat ggt    2593
Ala Ala Thr Val Gly Ala Ala Ala Trp Trp Phe Ile Ala Ala Asp Gly
845                 850                 855                 860 ggt ccg aga gtg acc ttc tac cag ctg agt cat ttc cta cag tgt aaa    2641
Gly Pro Arg Val Thr Phe Tyr Gln Leu Ser His Phe Leu Gln Cys Lys
                865                 870                 875 gag gac aac cca gac ttt gag gga gtg gat tgt gca gtc ttt gaa tcc    2689
Glu Asp Asn Pro Asp Phe Glu Gly Val Asp Cys Ala Val Phe Glu Ser
            880                 885                 890 cct tac cca atg aca atg gcg ctg tct gtt cta gtc acc ata gag atg    2737
Pro Tyr Pro Met Thr Met Ala Leu Ser Val Leu Val Thr Ile Glu Met
            895                 900                 905 tgt aac gcc ctc aac agt ttg tcg gaa aac cag tcc ctg cta agg atg    2785
Cys Asn Ala Leu Asn Ser Leu Ser Glu Asn Gln Ser Leu Leu Arg Met
            910                 915                 920 cca cct tgg gag aac att tgg ctc gtg ggc tcc atc tgc ctg tcc atg    2833
Pro Pro Trp Glu Asn Ile Trp Leu Val Gly Ser Ile Cys Leu Ser Met
925                 930                 935                 940 tca ctc cac ttc cta atc ctc tat gtg gaa ccc ctg cca ctt atc ttc    2881
Ser Leu His Phe Leu Ile Leu Tyr Val Glu Pro Leu Pro Leu Ile Phe
                945                 950                 955 cag atc aca ccg ctg aat ttg acc cag tgg ctg atg gtg ctg aaa atc    2929
Gln Ile Thr Pro Leu Asn Leu Thr Gln Trp Leu Met Val Leu Lys Ile
```

```
                960             965             970
tcc ttg cct gtg att cta atg gat gag acc ctc aag ttt gtg gcc cgc    2977
Ser Leu Pro Val Ile Leu Met Asp Glu Thr Leu Lys Phe Val Ala Arg
    975                 980                 985 aac tac ctg gaa cct gca ata ctg gag taa ccgcttccta aaccattttg      3027
Asn Tyr Leu Glu Pro Ala Ile Leu Glu
    990                 995 cagaaatgta agggtgttcg gttgcgtgca tgtgcgtttt tagcaacaca tctaccagcc  3087
ctctgcatga ttgatgttgg gggtaaaaga aaattagaaa aaagtcccca attcattgtg  3147
tgttacgtgg aggaaacatg tattaccagt ggggtttttt agcttttaaa tcaaaatgat  3207
aattacaaat gtacaatttt agcttaatgg atcagaaatc ctctccagag aagtttggtt  3267
tctttgctgc aagaagaatg aggttctgaa accttaccca agaacttaga agccatcagc  3327
caagtatcca tgtttctctg tgcaaaatgt catagcttaa ataaatgtac aatattcaat  3387
tgtaatgcat gccttcaagt tgtaagtagc cagatttctc tatgtgtca ttgaaacatg   3447
ctactttta attggccctg tacagtttgc ttatttataa atttattgaa aacactacag   3507
gtgttggtta aaatgtaggc ttctagctca taacttcagt tatttttga gtgtgcaaac   3567
agctattttg cactgtatta aatgtaactt atttaatgaa atcaaaagca gtagacagat  3627
gttggtgcaa tacgaatatt gtgatgcatt tatattaata aaatgctaaa cgtcaattta  3687
tcacaacgca tgtttgactt tagactgtaa atagagatca gtttatttct gtgctggtaa  3747
aaagtattgc acagacatgg tttcaggtaa ataaatctat tctatgat              3795
```

<210> SEQ ID NO 4
<211> LENGTH: 997
<212> TYPE: PRT
<213> ORGANISM: Sus scrofa

<400> SEQUENCE: 4

```
Met Glu Asn Ala His Thr Lys Thr Val Glu Glu Val Leu Gly His Phe
1               5                   10                  15

Gly Val Asn Glu Ser Thr Gly Leu Ser Leu Glu Gln Val Lys Lys Leu
            20                  25                  30

Lys Glu Arg Trp Gly Ser Asn Glu Leu Pro Ala Glu Glu Gly Lys Thr
        35                  40                  45

Leu Leu Glu Leu Val Ile Glu Gln Phe Glu Asp Leu Leu Val Arg Ile
    50                  55                  60

Leu Leu Leu Ala Ala Cys Ile Ser Phe Val Leu Ala Trp Phe Glu Glu
65                  70                  75                  80

Gly Glu Glu Thr Ile Thr Ala Phe Val Glu Pro Phe Val Ile Leu Leu
                85                  90                  95

Ile Leu Val Ala Asn Ala Ile Val Gly Val Trp Gln Glu Arg Asn Ala
            100                 105                 110

Glu Asn Ala Ile Glu Ala Leu Lys Glu Tyr Glu Pro Glu Met Gly Lys
        115                 120                 125

Val Tyr Arg Gln Asp Arg Lys Ser Val Gln Arg Ile Lys Ala Lys Asp
    130                 135                 140

Ile Val Pro Gly Asp Ile Val Glu Ile Ala Val Gly Asp Lys Val Pro
145                 150                 155                 160

Ala Asp Ile Arg Leu Thr Ser Ile Lys Ser Thr Thr Leu Arg Val Asp
                165                 170                 175

Gln Ser Ile Leu Thr Gly Glu Ser Val Ser Val Ile Lys His Thr Asp
            180                 185                 190
```

-continued

Pro Val Pro Asp Pro Arg Ala Val Asn Gln Asp Lys Lys Asn Met Leu
        195                 200                 205

Phe Ser Gly Thr Asn Ile Ala Ala Gly Lys Ala Met Gly Val Val
    210                 215                 220

Ala Thr Gly Val Asn Thr Glu Ile Gly Lys Ile Arg Asp Glu Met Val
225                 230                 235                 240

Ala Thr Glu Gln Glu Arg Thr Pro Leu Gln Gln Lys Leu Asp Glu Phe
                245                 250                 255

Gly Glu Gln Leu Ser Lys Val Ile Ser Leu Ile Cys Ile Ala Val Trp
                260                 265                 270

Ile Ile Asn Ile Gly His Phe Asn Asp Pro Val His Gly Gly Ser Trp
            275                 280                 285

Ile Arg Gly Ala Ile Tyr Tyr Phe Lys Ile Ala Val Ala Leu Ala Val
        290                 295                 300

Ala Ala Ile Pro Glu Gly Leu Pro Ala Val Ile Thr Thr Cys Leu Ala
305                 310                 315                 320

Leu Gly Thr Arg Arg Met Ala Lys Lys Asn Ala Ile Val Arg Ser Leu
                325                 330                 335

Pro Ser Val Glu Thr Leu Gly Cys Thr Ser Val Ile Cys Ser Asp Lys
                340                 345                 350

Thr Gly Thr Leu Thr Thr Asn Gln Met Ser Val Cys Arg Met Phe Ile
            355                 360                 365

Leu Asp Lys Val Glu Gly Asp Thr Cys Ser Leu Asn Glu Phe Thr Ile
        370                 375                 380

Thr Gly Ser Thr Tyr Ala Pro Ile Gly Glu Val His Lys Asp Asp Lys
385                 390                 395                 400

Pro Val Lys Cys His Gln Tyr Asp Gly Leu Val Glu Leu Ala Thr Ile
                405                 410                 415

Cys Ala Leu Cys Asn Asp Ser Ala Leu Asp Tyr Asn Glu Ala Lys Gly
                420                 425                 430

Val Tyr Glu Lys Val Gly Glu Ala Thr Glu Thr Ala Leu Thr Cys Leu
        435                 440                 445

Val Glu Lys Met Asn Val Phe Asp Thr Glu Leu Lys Gly Leu Ser Lys
        450                 455                 460

Ile Glu Arg Ala Asn Ala Cys Asn Ser Val Ile Lys Gln Leu Met Lys
465                 470                 475                 480

Lys Glu Phe Thr Leu Glu Phe Ser Arg Asp Arg Lys Ser Met Ser Val
                485                 490                 495

Tyr Cys Thr Pro Asn Lys Pro Ser Arg Thr Ser Met Ser Lys Met Phe
            500                 505                 510

Val Lys Gly Ala Pro Glu Gly Val Ile Asp Arg Cys Thr His Ile Arg
        515                 520                 525

Val Gly Ser Thr Lys Val Pro Met Thr Pro Gly Val Lys Gln Lys Ile
    530                 535                 540

Met Ser Val Ile Arg Glu Trp Gly Ser Gly Ser Asp Thr Leu Arg Cys
545                 550                 555                 560

Leu Ala Leu Ala Thr His Asp Asn Pro Met Arg Arg Glu Glu Met Asn
                565                 570                 575

Leu Glu Asp Ser Ala Asn Phe Ile Lys Tyr Glu Thr Asn Leu Thr Phe
                580                 585                 590

Val Gly Cys Val Gly Met Leu Asp Pro Pro Arg Ile Glu Val Ala Ser
            595                 600                 605

Ser Val Lys Leu Cys Arg Gln Ala Gly Ile Arg Val Ile Met Ile Thr
610                 615                 620

Gly Asp Asn Lys Gly Thr Ala Val Ala Ile Cys Arg Arg Ile Gly Ile
625                 630                 635                 640

Phe Gly Gln Asp Glu Asp Val Thr Ser Lys Ala Phe Thr Gly Arg Glu
                    645                 650                 655

Phe Asp Glu Leu Asn Pro Ser Ala Gln Arg Glu Ala Cys Leu Asn Ala
                660                 665                 670

Arg Cys Phe Ala Arg Val Glu Pro Ser His Lys Ser Lys Ile Val Glu
            675                 680                 685

Phe Leu Gln Ser Phe Asp Glu Ile Thr Ala Met Thr Gly Asp Gly Val
690                 695                 700

Asn Asp Ala Pro Ala Leu Lys Lys Ser Glu Ile Gly Ile Ala Met Gly
705                 710                 715                 720

Ser Gly Thr Ala Val Ala Lys Thr Ala Ser Glu Met Val Leu Ala Asp
                725                 730                 735

Asp Asn Phe Ser Thr Ile Val Ala Ala Val Glu Glu Gly Arg Ala Ile
                740                 745                 750

Tyr Asn Asn Met Lys Gln Phe Ile Arg Tyr Leu Ile Ser Ser Asn Val
            755                 760                 765

Gly Glu Val Val Cys Ile Phe Leu Thr Ala Ala Leu Gly Phe Pro Glu
770                 775                 780

Ala Leu Ile Pro Val Gln Leu Leu Trp Val Asn Leu Val Thr Asp Gly
785                 790                 795                 800

Leu Pro Ala Thr Ala Leu Gly Phe Asn Pro Pro Asp Leu Asp Ile Met
                805                 810                 815

Asn Lys Pro Pro Arg Asn Pro Lys Glu Pro Leu Ile Ser Gly Trp Leu
                820                 825                 830

Phe Phe Arg Tyr Leu Ala Ile Gly Cys Tyr Val Gly Ala Ala Thr Val
            835                 840                 845

Gly Ala Ala Ala Trp Trp Phe Ile Ala Ala Asp Gly Gly Pro Arg Val
850                 855                 860

Thr Phe Tyr Gln Leu Ser His Phe Leu Gln Cys Lys Glu Asp Asn Pro
865                 870                 875                 880

Asp Phe Glu Gly Val Asp Cys Ala Val Phe Glu Ser Pro Tyr Pro Met
                885                 890                 895

Thr Met Ala Leu Ser Val Leu Val Thr Ile Glu Met Cys Asn Ala Leu
                900                 905                 910

Asn Ser Leu Ser Glu Asn Gln Ser Leu Leu Arg Met Pro Pro Trp Glu
            915                 920                 925

Asn Ile Trp Leu Val Gly Ser Ile Cys Leu Ser Met Ser Leu His Phe
930                 935                 940

Leu Ile Leu Tyr Val Glu Pro Leu Pro Leu Ile Phe Gln Ile Thr Pro
945                 950                 955                 960

Leu Asn Leu Thr Gln Trp Leu Met Val Leu Lys Ile Ser Leu Pro Val
                965                 970                 975

Ile Leu Met Asp Glu Thr Leu Lys Phe Val Ala Arg Asn Tyr Leu Glu
                980                 985                 990

Pro Ala Ile Leu Glu
            995

<210> SEQ ID NO 5
<211> LENGTH: 4303
<212> TYPE: DNA

-continued

<213> ORGANISM: Rattus norvegicus
<220> FEATURE:
<221> NAME/KEY: misc_feature
<223> OTHER INFORMATION: Rat SERCA2a polynucleotide
<220> FEATURE:
<221> NAME/KEY: CDS
<222> LOCATION: (507)..(3500)

<400> SEQUENCE: 5

```
cggagccgtc cccgacgcca cctcccgtct cctccgccgc agtttcctcc gccgctgtcg      60
ggggtgcaga gctgaggggc tcgggcaggc gcgccgcgca gctcctctcc agtcgcccgc     120
ctcgccgtcc tccccaccga gggctcgccc gggcgcccct cctcagccgc gccgggtctc     180
ctcagcgcag cgccgcggcc tgcgctacct gcggccggct ggcaacagag gcaacgcaca     240
ctcgcggcgg ggcgggaggc tcgcagcccc tcgggcgggc tcggcgaggc ccggccgcgt     300
gcggcggttt ctgggggagg gggctcgggt gattcagcgc ccggtcaggc ggaagcggcc     360
gccgccgcgg aggaggagga gaaagaggag gggacagctg tccgcgcccg ggcgccgcg      420 gtggcacgag cccgcggccc gagtgcgagg cgaggcgag  gaggccgcgg ggacgcgagg     480
```

```
cgaggccggc cggggccccc gcagcc atg gag aac gct cac aca aag acc gtg     533
                              Met Glu Asn Ala His Thr Lys Thr Val
                              1               5 gag gag gtg ctg ggc cac ttc ggc gtc aac gag agc acg ggg ctg agc      581
Glu Glu Val Leu Gly His Phe Gly Val Asn Glu Ser Thr Gly Leu Ser
10              15                  20                  25 ctg gag cag gtc aag aag ctc aag gag aga tgg ggc tcc aac gaa ttg      629
Leu Glu Gln Val Lys Lys Leu Lys Glu Arg Trp Gly Ser Asn Glu Leu
        30                  35                  40 ccg gct gaa gaa gga aag acc ttg ctg gaa ctt gtg atc gag cag ttt      677
Pro Ala Glu Glu Gly Lys Thr Leu Leu Glu Leu Val Ile Glu Gln Phe
    45                  50                  55 gaa gac tta cta gtt aga att tta ttg ctg gca gca tgt ata tct ttc      725
Glu Asp Leu Leu Val Arg Ile Leu Leu Leu Ala Ala Cys Ile Ser Phe
60                  65                  70 gtt ttg gct tgg ttc gaa gaa ggt gaa gaa acg att aca gcc ttt gta      773
Val Leu Ala Trp Phe Glu Glu Gly Glu Glu Thr Ile Thr Ala Phe Val
    75                  80                  85 gaa cct ttt gta att ctg ctt ata ttg gta gcc aat gca att gtg ggt      821
Glu Pro Phe Val Ile Leu Leu Ile Leu Val Ala Asn Ala Ile Val Gly
90                  95                  100                 105 gta tgg cag gag aga aac gct gaa aat gca ata gaa gct ctt aag gag      869
Val Trp Gln Glu Arg Asn Ala Glu Asn Ala Ile Glu Ala Leu Lys Glu
            110                 115                 120 tat gaa cct gaa atg ggc aag gtg tat cga cag gac aga aag agt gtg      917
Tyr Glu Pro Glu Met Gly Lys Val Tyr Arg Gln Asp Arg Lys Ser Val
        125                 130                 135 cag cgg att aaa gcg aaa gat ata gtt cct ggg gat ata gtg gaa att      965
Gln Arg Ile Lys Ala Lys Asp Ile Val Pro Gly Asp Ile Val Glu Ile
    140                 145                 150 gct gtt ggt gac aaa gtt ccg gct gac att aga ttg aca tcc atc aag     1013
Ala Val Gly Asp Lys Val Pro Ala Asp Ile Arg Leu Thr Ser Ile Lys
155                 160                 165 tct aca act ctg aga gtt gac cag tcg att ctt aca ggt gaa tct gtc     1061
Ser Thr Thr Leu Arg Val Asp Gln Ser Ile Leu Thr Gly Glu Ser Val
170                 175                 180                 185 tcg gtc atc aag cat act gac cct gtc cct gac cca cga gct gtt aat     1109
Ser Val Ile Lys His Thr Asp Pro Val Pro Asp Pro Arg Ala Val Asn
            190                 195                 200 caa gac aaa aag aac atg ctc ttt tct ggc aca aac atc gct gct ggc     1157
Gln Asp Lys Lys Asn Met Leu Phe Ser Gly Thr Asn Ile Ala Ala Gly
```

```
                Gln Asp Lys Lys Asn Met Leu Phe Ser Gly Thr Asn Ile Ala Ala Gly
                            205                 210                 215 aaa gct atg gga gtg gtg gtg gcg act gga gtc aat act gag atc ggc          1205
Lys Ala Met Gly Val Val Val Ala Thr Gly Val Asn Thr Glu Ile Gly
            220                 225                 230 aag atc cgg gat gaa atg gtt gca aca gaa cag gag aga aca ccc cta          1253
Lys Ile Arg Asp Glu Met Val Ala Thr Glu Gln Glu Arg Thr Pro Leu
    235                 240                 245 cag cag aag ctg gac gag ttt ggg gaa cag ctt tcc aaa gtt atc tcc          1301
Gln Gln Lys Leu Asp Glu Phe Gly Glu Gln Leu Ser Lys Val Ile Ser
250                 255                 260                 265 ctc att tgc att gca gtc tgg atc atc aac atc ggg cat ttc aat gac          1349
Leu Ile Cys Ile Ala Val Trp Ile Ile Asn Ile Gly His Phe Asn Asp
                270                 275                 280 cca gtt cat ggt ggc tct tgg atc aga ggt gcc atc tac tac ttt aag          1397
Pro Val His Gly Gly Ser Trp Ile Arg Gly Ala Ile Tyr Tyr Phe Lys
            285                 290                 295 att gca gtg gcc ctg gct gtt gct gcc atc cct gag ggt ctg cct gct          1445
Ile Ala Val Ala Leu Ala Val Ala Ala Ile Pro Glu Gly Leu Pro Ala
    300                 305                 310 gtc atc acc acc tgc ttg gct ctt gga act cga agg atg gca aag aaa          1493
Val Ile Thr Thr Cys Leu Ala Leu Gly Thr Arg Arg Met Ala Lys Lys
315                 320                 325 aat gct att gtt cga agt ctg cct tct gtg gaa acc ctt ggt tgt act          1541
Asn Ala Ile Val Arg Ser Leu Pro Ser Val Glu Thr Leu Gly Cys Thr
330                 335                 340                 345 tct gtt atc tgc tca gac aag acc ggc aca ctt acc aca aac cag atg          1589
Ser Val Ile Cys Ser Asp Lys Thr Gly Thr Leu Thr Thr Asn Gln Met
                350                 355                 360 tcc gtc tgc agg atg ttc att ctg gac aaa gta gaa ggt gat act tgt          1637
Ser Val Cys Arg Met Phe Ile Leu Asp Lys Val Glu Gly Asp Thr Cys
            365                 370                 375 tcc ctt aat gag ttt acc ata act gga tca acc tat gca ccc att gga          1685
Ser Leu Asn Glu Phe Thr Ile Thr Gly Ser Thr Tyr Ala Pro Ile Gly
    380                 385                 390 gaa gtg caa aaa gat gac aag cca gtg aaa tgc cat cag tat gac ggg          1733
Glu Val Gln Lys Asp Asp Lys Pro Val Lys Cys His Gln Tyr Asp Gly
395                 400                 405 ctt gta gag tta gca acg atc tgt gct ctg tgt aat gac tct gct ttg          1781
Leu Val Glu Leu Ala Thr Ile Cys Ala Leu Cys Asn Asp Ser Ala Leu
410                 415                 420                 425 gat tac aat gag gcg aag ggt gtg tat gaa aaa gtt gga gaa gcc aca          1829
Asp Tyr Asn Glu Ala Lys Gly Val Tyr Glu Lys Val Gly Glu Ala Thr
                430                 435                 440 gag act gct ctc acg tgc ctg gta gag aag atg aat gta ttc gac acg          1877
Glu Thr Ala Leu Thr Cys Leu Val Glu Lys Met Asn Val Phe Asp Thr
            445                 450                 455 gag ctg aag gga ctt tct aaa ata gaa cgc gcc aac gcc tgc aac tcg          1925
Glu Leu Lys Gly Leu Ser Lys Ile Glu Arg Ala Asn Ala Cys Asn Ser
    460                 465                 470 gtc ata aaa cag ctc atg aag aag gaa ttc acg cta gag ttt tca cgt          1973
Val Ile Lys Gln Leu Met Lys Lys Glu Phe Thr Leu Glu Phe Ser Arg
475                 480                 485 gat aga aaa tca atg tcc gtc tac tgt aca cca aac aaa ccg agc cgg          2021
Asp Arg Lys Ser Met Ser Val Tyr Cys Thr Pro Asn Lys Pro Ser Arg
490                 495                 500                 505 acg tcc atg agc aag atg ttt gtg aag ggt gct cca gaa ggt gtc atc          2069
Thr Ser Met Ser Lys Met Phe Val Lys Gly Ala Pro Glu Gly Val Ile
                510                 515                 520
```

-continued

| | | |
|---|---|---|
| gac agg tgc acc cac atc cga gtt gga agt acc aag gtc ccc atg acg<br>Asp Arg Cys Thr His Ile Arg Val Gly Ser Thr Lys Val Pro Met Thr<br>525                        530                      535 | 2117 |
| cct ggt gtt aaa cag aag att atg tct gtc att cgg gag tgg ggc agt<br>Pro Gly Val Lys Gln Lys Ile Met Ser Val Ile Arg Glu Trp Gly Ser<br>540                        545                      550 | 2165 |
| ggc agc gac aca ctg cgg tgc ctg gct ctg gcc act cat gac aac ccg<br>Gly Ser Asp Thr Leu Arg Cys Leu Ala Leu Ala Thr His Asp Asn Pro<br>555                        560                      565 | 2213 |
| ctg agg aga gag gag atg cac ctg gaa gat tct gcg aac ttc atc aaa<br>Leu Arg Arg Glu Glu Met His Leu Glu Asp Ser Ala Asn Phe Ile Lys<br>570                        575                      580                      585 | 2261 |
| tat gag acc aat ctg act ttc gtt ggc tgt gtg ggc atg ctg gac cct<br>Tyr Glu Thr Asn Leu Thr Phe Val Gly Cys Val Gly Met Leu Asp Pro<br>590                        595                      600 | 2309 |
| ccc agg att gaa gtg gcc tct tct gtg aag ctg tgc cgg caa gcg ggc<br>Pro Arg Ile Glu Val Ala Ser Ser Val Lys Leu Cys Arg Gln Ala Gly<br>605                        610                      615 | 2357 |
| atc cga gtc atc atg atc act ggg gat aac aaa ggc act gct gtg gcc<br>Ile Arg Val Ile Met Ile Thr Gly Asp Asn Lys Gly Thr Ala Val Ala<br>620                        625                      630 | 2405 |
| atc tgt cgc cgc att ggc atc ttt ggg cag gat gag gat gtg aca tca<br>Ile Cys Arg Arg Ile Gly Ile Phe Gly Gln Asp Glu Asp Val Thr Ser<br>635                        640                      645 | 2453 |
| aag gct ttt aca ggg cga gaa ttt gat gaa tta agc ccc tca gcc cag<br>Lys Ala Phe Thr Gly Arg Glu Phe Asp Glu Leu Ser Pro Ser Ala Gln<br>650                        655                      660                      665 | 2501 |
| aga gac gcc tgc tta aat gcc cgt tgt ttt gct cga gtt gaa cct tcc<br>Arg Asp Ala Cys Leu Asn Ala Arg Cys Phe Ala Arg Val Glu Pro Ser<br>670                        675                      680 | 2549 |
| cac aag tct aag atc gtt gag ttc ctg cag tcc ttt gat gag atc aca<br>His Lys Ser Lys Ile Val Glu Phe Leu Gln Ser Phe Asp Glu Ile Thr<br>685                        690                      695 | 2597 |
| gct atg act ggt gat ggt gtg aac gac gcg ccc gct ctg aag aag tcg<br>Ala Met Thr Gly Asp Gly Val Asn Asp Ala Pro Ala Leu Lys Lys Ser<br>700                        705                      710 | 2645 |
| gaa atc ggg att gcc atg ggc tca ggg act gca gtg gct aag acg gcc<br>Glu Ile Gly Ile Ala Met Gly Ser Gly Thr Ala Val Ala Lys Thr Ala<br>715                        720                      725 | 2693 |
| tct gag atg gtg ctg gcc gac gac aac ttc tcc acc atc gtg gcc gct<br>Ser Glu Met Val Leu Ala Asp Asp Asn Phe Ser Thr Ile Val Ala Ala<br>730                        735                      740                      745 | 2741 |
| gtt gag gag ggg cgc gcc atc tac aac aac atg aag cag ttc atc cgc<br>Val Glu Glu Gly Arg Ala Ile Tyr Asn Asn Met Lys Gln Phe Ile Arg<br>750                        755                      760 | 2789 |
| tac ctc atc tcc tcc aac gtg ggg gag gtg gtc tgt atc ttc ctg acg<br>Tyr Leu Ile Ser Ser Asn Val Gly Glu Val Val Cys Ile Phe Leu Thr<br>765                        770                      775 | 2837 |
| gca gcc ctt ggg ttt cct gaa gct ttg att cct gtc cag tta ctc tgg<br>Ala Ala Leu Gly Phe Pro Glu Ala Leu Ile Pro Val Gln Leu Leu Trp<br>780                        785                      790 | 2885 |
| gtc aat ctg gtg acg gat ggt ctg cct gcc act gcg ctg ggg ttc aat<br>Val Asn Leu Val Thr Asp Gly Leu Pro Ala Thr Ala Leu Gly Phe Asn<br>795                        800                      805 | 2933 |
| cct cca gat ctg gac atc atg aac aaa ccc cca cgg aac cca aaa gaa<br>Pro Pro Asp Leu Asp Ile Met Asn Lys Pro Pro Arg Asn Pro Lys Glu<br>810                        815                      820                      825 | 2981 |
| ccg ctg atc agc ggg tgg ctc ttt ttc cgt tac ctg gct att ggc tgt<br>Pro Leu Ile Ser Gly Trp Leu Phe Phe Arg Tyr Leu Ala Ile Gly Cys<br>830                        835                      840 | 3029 |

```
tat gtt ggc gct gcc acc gtg ggt gct gct gcg tgg tgg ttc atc gct    3077
Tyr Val Gly Ala Ala Thr Val Gly Ala Ala Ala Trp Trp Phe Ile Ala
            845                 850                 855 gct gac ggt ggt ccg aga gtc tcc ttc tac cag ctg agt cat ttc ctg    3125
Ala Asp Gly Gly Pro Arg Val Ser Phe Tyr Gln Leu Ser His Phe Leu
        860                 865                 870 cag tgt aag gag gac aac cca gac ttc gaa gga gtg gat tgt gca atc    3173
Gln Cys Lys Glu Asp Asn Pro Asp Phe Glu Gly Val Asp Cys Ala Ile
    875                 880                 885 ttt gag tcc ccg tat ccg atg aca atg gca ctt tct gtt cta gtc acc    3221
Phe Glu Ser Pro Tyr Pro Met Thr Met Ala Leu Ser Val Leu Val Thr
890                 895                 900                 905 ata gag atg tgc aat gcc ctc aac agc ttg tct gaa aac cag tcc ctg    3269
Ile Glu Met Cys Asn Ala Leu Asn Ser Leu Ser Glu Asn Gln Ser Leu
            910                 915                 920 ctg agg atg ccc ccc tgg gag aac atc tgg ctc gtg ggc tcc atc tgc    3317
Leu Arg Met Pro Pro Trp Glu Asn Ile Trp Leu Val Gly Ser Ile Cys
        925                 930                 935 ttg tcc atg tcc ctt cac ttc ttg atc ctc tac gtg gaa cct ttg cca    3365
Leu Ser Met Ser Leu His Phe Leu Ile Leu Tyr Val Glu Pro Leu Pro
    940                 945                 950 ctc att ttc cag atc aca ccg ctg aat ctg acc cag tgg ctg atg gtg    3413
Leu Ile Phe Gln Ile Thr Pro Leu Asn Leu Thr Gln Trp Leu Met Val
955                 960                 965 ctg aaa atc tcc ctg cct gtg atc ctc atg gac gag acg ctc aag ttt    3461
Leu Lys Ile Ser Leu Pro Val Ile Leu Met Asp Glu Thr Leu Lys Phe
            970                 975                 980                 985 gtg gcc cga aac tac ctg gag cct gca ata ctg gag taa ccgcttccta     3510
Val Ala Arg Asn Tyr Leu Glu Pro Ala Ile Leu Glu
            990                 995 aacattgcag aaatgtaagg gtgttcgggt gcgtgcatgt gcgttgttag caacacatct   3570
tccagccctc tgcatgactg agcttgggga agagaaata gaacagcccc cagctcactg    3630
tgtgatgtgg aggaaatgtg tattacaagt ggggttttag ctgttgagtc aaaataataa   3690
caagtgtaca atttagcata aggaatcgga gagcctctcc agagaagtcg gtttctttgc   3750
tgcaagaaga atgaggttct gaacccttat ccaagaacag aagccatcag ccaagtctcc   3810
acatttctct gcaaaatgtt gtagcctcta taactgtatg atagtgtaat gcatgccttc   3870
agttgtaagt ggccagatcg cgctacagtg acattgaaac ctgctctcta attggccctg   3930
tacagtttgc ttatttataa attcatttaa aacactacag ctgttgaatg gttacaacct   3990
aggcctccgg tcctaacttc agttgttctc ctcggtgtgc agccagctgt tccacactgt   4050
attattgtaa cttatttagt gaagtcagaa gcagtagaca gatgttggtg caatacaagt   4110
attgtgtgca tttatcgtaa taaagtgctc cgcgtcggtt cagttcctca cagcttctca   4170
cagtgcatgt ctgactgtag tctgtaaata gaggtcagtg tccgtgctgc taacaggtat   4230
cgatcgcaca gacatgattt caggtaaata aatcgattct acgataaacc ctcaaaaaaa   4290
aaaaaaaaaa aaa                                                      4303

<210> SEQ ID NO 6
<211> LENGTH: 997
<212> TYPE: PRT
<213> ORGANISM: Rattus norvegicus

<400> SEQUENCE: 6

Met Glu Asn Ala His Thr Lys Thr Val Glu Glu Val Leu Gly His Phe
1               5                   10                  15
```

```
Gly Val Asn Glu Ser Thr Gly Leu Ser Leu Glu Gln Val Lys Lys Leu
             20                  25                  30

Lys Glu Arg Trp Gly Ser Asn Glu Leu Pro Ala Glu Gly Lys Thr
         35                  40                  45

Leu Leu Glu Leu Val Ile Glu Gln Phe Glu Asp Leu Leu Val Arg Ile
 50                  55                  60

Leu Leu Leu Ala Ala Cys Ile Ser Phe Val Leu Ala Trp Phe Glu Glu
 65                  70                  75                  80

Gly Glu Glu Thr Ile Thr Ala Phe Val Glu Pro Phe Val Ile Leu Leu
                 85                  90                  95

Ile Leu Val Ala Asn Ala Ile Val Gly Val Trp Gln Glu Arg Asn Ala
                100                 105                 110

Glu Asn Ala Ile Glu Ala Leu Lys Glu Tyr Glu Pro Glu Met Gly Lys
                115                 120                 125

Val Tyr Arg Gln Asp Arg Lys Ser Val Gln Arg Ile Lys Ala Lys Asp
130                 135                 140

Ile Val Pro Gly Asp Ile Val Glu Ile Ala Val Gly Asp Lys Val Pro
145                 150                 155                 160

Ala Asp Ile Arg Leu Thr Ser Ile Lys Ser Thr Thr Leu Arg Val Asp
                165                 170                 175

Gln Ser Ile Leu Thr Gly Glu Ser Val Ser Val Ile Lys His Thr Asp
                180                 185                 190

Pro Val Pro Asp Pro Arg Ala Val Asn Gln Asp Lys Lys Asn Met Leu
                195                 200                 205

Phe Ser Gly Thr Asn Ile Ala Ala Gly Lys Ala Met Gly Val Val Val
210                 215                 220

Ala Thr Gly Val Asn Thr Glu Ile Gly Lys Ile Arg Asp Glu Met Val
225                 230                 235                 240

Ala Thr Glu Gln Glu Arg Thr Pro Leu Gln Gln Lys Leu Asp Glu Phe
                245                 250                 255

Gly Glu Gln Leu Ser Lys Val Ile Ser Leu Ile Cys Ile Ala Val Trp
                260                 265                 270

Ile Ile Asn Ile Gly His Phe Asn Asp Pro Val His Gly Gly Ser Trp
                275                 280                 285

Ile Arg Gly Ala Ile Tyr Tyr Phe Lys Ile Ala Val Ala Leu Ala Val
290                 295                 300

Ala Ala Ile Pro Glu Gly Leu Pro Ala Val Ile Thr Thr Cys Leu Ala
305                 310                 315                 320

Leu Gly Thr Arg Arg Met Ala Lys Lys Asn Ala Ile Val Arg Ser Leu
                325                 330                 335

Pro Ser Val Glu Thr Leu Gly Cys Thr Ser Val Ile Cys Ser Asp Lys
                340                 345                 350

Thr Gly Thr Leu Thr Thr Asn Gln Met Ser Val Cys Arg Met Phe Ile
                355                 360                 365

Leu Asp Lys Val Glu Gly Asp Thr Cys Ser Leu Asn Glu Phe Thr Ile
                370                 375                 380

Thr Gly Ser Thr Tyr Ala Pro Ile Gly Glu Val Gln Lys Asp Asp Lys
385                 390                 395                 400

Pro Val Lys Cys His Gln Tyr Asp Gly Leu Val Glu Leu Ala Thr Ile
                405                 410                 415

Cys Ala Leu Cys Asn Asp Ser Ala Leu Asp Tyr Asn Glu Ala Lys Gly
420                 425                 430
```

```
Val Tyr Glu Lys Val Gly Glu Ala Thr Glu Thr Ala Leu Thr Cys Leu
            435                 440                 445

Val Glu Lys Met Asn Val Phe Asp Thr Glu Leu Lys Gly Leu Ser Lys
        450                 455                 460

Ile Glu Arg Ala Asn Ala Cys Asn Ser Val Ile Lys Gln Leu Met Lys
465                 470                 475                 480

Lys Glu Phe Thr Leu Glu Phe Ser Arg Asp Arg Lys Ser Met Ser Val
                485                 490                 495

Tyr Cys Thr Pro Asn Lys Pro Ser Arg Thr Ser Met Ser Lys Met Phe
            500                 505                 510

Val Lys Gly Ala Pro Glu Gly Val Ile Asp Arg Cys Thr His Ile Arg
        515                 520                 525

Val Gly Ser Thr Lys Val Pro Met Thr Pro Gly Val Lys Gln Lys Ile
    530                 535                 540

Met Ser Val Ile Arg Glu Trp Gly Ser Gly Ser Asp Thr Leu Arg Cys
545                 550                 555                 560

Leu Ala Leu Ala Thr His Asp Asn Pro Leu Arg Arg Glu Glu Met His
                565                 570                 575

Leu Glu Asp Ser Ala Asn Phe Ile Lys Tyr Glu Thr Asn Leu Thr Phe
            580                 585                 590

Val Gly Cys Val Gly Met Leu Asp Pro Pro Arg Ile Glu Val Ala Ser
        595                 600                 605

Ser Val Lys Leu Cys Arg Gln Ala Gly Ile Arg Val Ile Met Ile Thr
    610                 615                 620

Gly Asp Asn Lys Gly Thr Ala Val Ala Ile Cys Arg Arg Ile Gly Ile
625                 630                 635                 640

Phe Gly Gln Asp Glu Asp Val Thr Ser Lys Ala Phe Thr Gly Arg Glu
                645                 650                 655

Phe Asp Glu Leu Ser Pro Ser Ala Gln Arg Asp Ala Cys Leu Asn Ala
            660                 665                 670

Arg Cys Phe Ala Arg Val Glu Pro Ser His Lys Ser Lys Ile Val Glu
        675                 680                 685

Phe Leu Gln Ser Phe Asp Glu Ile Thr Ala Met Thr Gly Asp Gly Val
    690                 695                 700

Asn Asp Ala Pro Ala Leu Lys Lys Ser Glu Ile Gly Ile Ala Met Gly
705                 710                 715                 720

Ser Gly Thr Ala Val Ala Lys Thr Ala Ser Glu Met Val Leu Ala Asp
                725                 730                 735

Asp Asn Phe Ser Thr Ile Val Ala Ala Val Glu Glu Gly Arg Ala Ile
            740                 745                 750

Tyr Asn Asn Met Lys Gln Phe Ile Arg Tyr Leu Ile Ser Ser Asn Val
        755                 760                 765

Gly Glu Val Val Cys Ile Phe Leu Thr Ala Ala Leu Gly Phe Pro Glu
    770                 775                 780

Ala Leu Ile Pro Val Gln Leu Leu Trp Val Asn Leu Val Thr Asp Gly
785                 790                 795                 800

Leu Pro Ala Thr Ala Leu Gly Phe Asn Pro Pro Asp Leu Asp Ile Met
                805                 810                 815

Asn Lys Pro Pro Arg Asn Pro Lys Glu Pro Leu Ile Ser Gly Trp Leu
            820                 825                 830

Phe Phe Arg Tyr Leu Ala Ile Gly Cys Tyr Val Gly Ala Ala Thr Val
        835                 840                 845

Gly Ala Ala Ala Trp Trp Phe Ile Ala Ala Asp Gly Gly Pro Arg Val
```

```
                850              855              860
Ser Phe Tyr Gln Leu Ser His Phe Leu Gln Cys Lys Glu Asp Asn Pro
865              870              875              880

Asp Phe Glu Gly Val Asp Cys Ala Ile Phe Glu Ser Pro Tyr Pro Met
                885              890              895

Thr Met Ala Leu Ser Val Leu Val Thr Ile Glu Met Cys Asn Ala Leu
                900              905              910

Asn Ser Leu Ser Glu Asn Gln Ser Leu Leu Arg Met Pro Pro Trp Glu
            915              920              925

Asn Ile Trp Leu Val Gly Ser Ile Cys Leu Ser Met Ser Leu His Phe
        930              935              940

Leu Ile Leu Tyr Val Glu Pro Leu Pro Leu Ile Phe Gln Ile Thr Pro
945              950              955              960

Leu Asn Leu Thr Gln Trp Leu Met Val Leu Lys Ile Ser Leu Pro Val
                965              970              975

Ile Leu Met Asp Glu Thr Leu Lys Phe Val Ala Arg Asn Tyr Leu Glu
                980              985              990

Pro Ala Ile Leu Glu
        995

<210> SEQ ID NO 7
<211> LENGTH: 4353
<212> TYPE: DNA
<213> ORGANISM: Mus musculus
<220> FEATURE:
<221> NAME/KEY: misc_feature
<223> OTHER INFORMATION: Mouse SERCA2a polynucleotide
<220> FEATURE:
<221> NAME/KEY: CDS
<222> LOCATION: (541)..(3537)

<400> SEQUENCE: 7
agagcagcct ccgcggagcc gtccccgacg ccgccacctc ccgtctcctc cgccgcagtt    60
ccctccgccg ccgctgtcgg gggtgcagag ctgaggggct cgggccggcg cgccgcgcag   120
ctcctctccc gtcgcctgcc tcgcggttcc cggcgccgag ggctcggccc ggcgccgctc   180
ctcatctgcg ccccgtctcc tcggcgcagc gcccggggcc tgcgctgccc gcggccggct   240
ggcagctgct gaagcgaccc acactcgcgg cggggcggga ggctcgcagt ccctcgggcg   300
ggctcggcga ggccgggccg cgtgcggcgg tttctggggg agggggctcg ggtgattcag   360
cgccccggtc aggcggaagc ggccgccgcc gccgcggagg aggaggagga gaagaaaaag   420
gaggggacag ctgtccgcgc ccgggcgccc gcggtggcac gagcccgcgg ccggagtgcg   480
aggcggtagg cgaggaggcc gcggggacgc gaggcgaggc cggccggggc cccgcagcc   540 atg gag aac gct cac aca aag acc gtg gag gag gtg ctg ggc cac ttc    588
Met Glu Asn Ala His Thr Lys Thr Val Glu Glu Val Leu Gly His Phe
1               5                  10                  15 ggg gtc aac gag agc acg ggg ctg agc ttg gag cag gtc aag aag ctc    636
Gly Val Asn Glu Ser Thr Gly Leu Ser Leu Glu Gln Val Lys Lys Leu
                20                  25                  30 aag gag aga tgg ggc tcc aac gaa ttg ccg gct gaa gaa gga aaa acc    684
Lys Glu Arg Trp Gly Ser Asn Glu Leu Pro Ala Glu Glu Gly Lys Thr
            35                  40                  45 ttg ctg gaa ctt gtg att gag cag ttt gaa gac tta cta gtt aga att    732
Leu Leu Glu Leu Val Ile Glu Gln Phe Glu Asp Leu Leu Val Arg Ile
        50                  55                  60 tta ctg ctg gca gca tgt ata tct ttc gtt tgg ctt tgg ttc gag gaa    780
Leu Leu Leu Ala Ala Cys Ile Ser Phe Val Trp Leu Trp Phe Glu Glu
```

```
                    65                  70                  75                  80
ggg gaa gaa acg att aca gcc ttt gta gag ccg ttt gta att ctg ctt           828
Gly Glu Glu Thr Ile Thr Ala Phe Val Glu Pro Phe Val Ile Leu Leu
                        85                  90                  95 atc ttg gta gcc aat gca atc gtg ggt gtg tgg cag gaa aga aat gct           876
Ile Leu Val Ala Asn Ala Ile Val Gly Val Trp Gln Glu Arg Asn Ala
                100                 105                 110 gaa aat gca ata gaa gct ctt aag gaa tat gag cct gaa atg ggc aaa           924
Glu Asn Ala Ile Glu Ala Leu Lys Glu Tyr Glu Pro Glu Met Gly Lys
            115                 120                 125 gtg tat cga cag gac aga aag agt gtg caa cga att aaa gct aaa gac           972
Val Tyr Arg Gln Asp Arg Lys Ser Val Gln Arg Ile Lys Ala Lys Asp
        130                 135                 140 ata gtt cct ggt gat ata gtg gaa att gct gtt ggt gac aaa gtt cct          1020
Ile Val Pro Gly Asp Ile Val Glu Ile Ala Val Gly Asp Lys Val Pro
145                 150                 155                 160 gct gat att aga ttg aca tcc atc aag tct aca act cta aga gtc gac          1068
Ala Asp Ile Arg Leu Thr Ser Ile Lys Ser Thr Thr Leu Arg Val Asp
                    165                 170                 175 cag tca att ctt aca ggt gaa tct gtc tcc gtc atc aag cat act gac          1116
Gln Ser Ile Leu Thr Gly Glu Ser Val Ser Val Ile Lys His Thr Asp
                180                 185                 190 cct gtc cct gac ccc cga gct gtt aat caa gac aaa aag aac atg ctc          1164
Pro Val Pro Asp Pro Arg Ala Val Asn Gln Asp Lys Lys Asn Met Leu
            195                 200                 205 ttt tct ggt aca aac att gct gct ggg aaa gct atg gga gtg gtg gtg          1212
Phe Ser Gly Thr Asn Ile Ala Ala Gly Lys Ala Met Gly Val Val Val
        210                 215                 220 gca act gga gtt aat act gag atc ggc aag atc cgg gat gaa atg gtg          1260
Ala Thr Gly Val Asn Thr Glu Ile Gly Lys Ile Arg Asp Glu Met Val
225                 230                 235                 240 gca aca gaa cag gag aga aca ccc cta cag cag aag cta gac gag ttt          1308
Ala Thr Glu Gln Glu Arg Thr Pro Leu Gln Gln Lys Leu Asp Glu Phe
                    245                 250                 255 ggg gag cag ctt tcc aaa gtt atc tcc ctc att tgc att gca gtc tgg          1356
Gly Glu Gln Leu Ser Lys Val Ile Ser Leu Ile Cys Ile Ala Val Trp
                260                 265                 270 atc atc aac att ggg cat ttc aat gac cca gtt cat ggt ggc tcc tgg          1404
Ile Ile Asn Ile Gly His Phe Asn Asp Pro Val His Gly Gly Ser Trp
            275                 280                 285 atc agg ggt gcc atc tac tac ttt aag att gcc gtg gcc ctg gct gtt          1452
Ile Arg Gly Ala Ile Tyr Tyr Phe Lys Ile Ala Val Ala Leu Ala Val
        290                 295                 300 gcc gca atc cct gag ggt ctg cct gct gtc atc acc acc tgc tta gct          1500
Ala Ala Ile Pro Glu Gly Leu Pro Ala Val Ile Thr Thr Cys Leu Ala
305                 310                 315                 320 ctt gga act cgt agg atg gca aag aaa aat gct atc gtt cga agt ctg          1548
Leu Gly Thr Arg Arg Met Ala Lys Lys Asn Ala Ile Val Arg Ser Leu
                    325                 330                 335 cct tct gtg gag acc ctt ggt tgt act tct gtt atc tgc tca gat aag          1596
Pro Ser Val Glu Thr Leu Gly Cys Thr Ser Val Ile Cys Ser Asp Lys
                340                 345                 350 aca ggc aca ctt acc aca aac cag atg tcc gtg tgc agg atg ttc att          1644
Thr Gly Thr Leu Thr Thr Asn Gln Met Ser Val Cys Arg Met Phe Ile
            355                 360                 365 ctg gac aaa gta gaa ggt gac act tgt tcc ctt aat gag ttc agc ata          1692
Leu Asp Lys Val Glu Gly Asp Thr Cys Ser Leu Asn Glu Phe Ser Ile
        370                 375                 380 act gga tcc aca tat gca cca att gga gaa gtg caa aag gat gat aag          1740
Thr Gly Ser Thr Tyr Ala Pro Ile Gly Glu Val Gln Lys Asp Asp Lys
```

|  |  |
|---|---|
| Thr Gly Ser Thr Tyr Ala Pro Ile Gly Glu Val Gln Lys Asp Asp Lys<br>385                          390                            395                        400 |  |
| cca gtg aag tgc cat cag tat gac ggg ctt gta gag tta gcc acc atc<br>Pro Val Lys Cys His Gln Tyr Asp Gly Leu Val Glu Leu Ala Thr Ile<br>                            405                          410                         415 | 1788 |
| tgt gct ctg tgt aat gac tct gct ttg gat tat aat gag gca aag ggt<br>Cys Ala Leu Cys Asn Asp Ser Ala Leu Asp Tyr Asn Glu Ala Lys Gly<br>              420                          425                         430 | 1836 |
| gtg tat gag aaa gtt gga gaa gct acc gag act gct ctc acg tgc ctg<br>Val Tyr Glu Lys Val Gly Glu Ala Thr Glu Thr Ala Leu Thr Cys Leu<br>                            435                          440                         445 | 1884 |
| gtg gag aag atg aat gta ttt gat act gag ctg aag ggg ctt tct aaa<br>Val Glu Lys Met Asn Val Phe Asp Thr Glu Leu Lys Gly Leu Ser Lys<br>        450                          455                         460 | 1932 |
| ata gag cgt gca aac gcc tgc aac tcg gtc ata aag cag ctg atg aag<br>Ile Glu Arg Ala Asn Ala Cys Asn Ser Val Ile Lys Gln Leu Met Lys<br>465                          470                            475                        480 | 1980 |
| aag gag ttc act ctg gag ttt tca cgg gat aga aaa tca atg tcc gtc<br>Lys Glu Phe Thr Leu Glu Phe Ser Arg Asp Arg Lys Ser Met Ser Val<br>                            485                          490                         495 | 2028 |
| tat tgt acc cca aac aag cca agc cgg aca tcc atg agc aag atg ttt<br>Tyr Cys Thr Pro Asn Lys Pro Ser Arg Thr Ser Met Ser Lys Met Phe<br>        500                          505                         510 | 2076 |
| gtg aag ggg gct cca gaa ggt gtc atc gat agg tgc acc cac atc cga<br>Val Lys Gly Ala Pro Glu Gly Val Ile Asp Arg Cys Thr His Ile Arg<br>                            515                          520                         525 | 2124 |
| gtt gga agt acc aag gtc ccc atg act cct ggt gtc aaa cag aag att<br>Val Gly Ser Thr Lys Val Pro Met Thr Pro Gly Val Lys Gln Lys Ile<br>        530                          535                         540 | 2172 |
| atg tct gtc att cgg gag tgg ggc agt ggc agc gac acg cta cgg tgc<br>Met Ser Val Ile Arg Glu Trp Gly Ser Gly Ser Asp Thr Leu Arg Cys<br>545                          550                            555                        560 | 2220 |
| ctg gct ctg gcc act cat gac aac cca ctg aag aga gag gag atg cac<br>Leu Ala Leu Ala Thr His Asp Asn Pro Leu Lys Arg Glu Glu Met His<br>                            565                          570                         575 | 2268 |
| ctg gaa gac tct gct aac ttc atc aaa tac gag acc aac ctg act ttc<br>Leu Glu Asp Ser Ala Asn Phe Ile Lys Tyr Glu Thr Asn Leu Thr Phe<br>        580                          585                         590 | 2316 |
| gtc ggc tgt gtg ggc atg ctg gat cct ccc agg att gaa gta gcc tct<br>Val Gly Cys Val Gly Met Leu Asp Pro Pro Arg Ile Glu Val Ala Ser<br>                            595                          600                         605 | 2364 |
| tct gtg aag ctg tgc cgg caa gca ggc atc cgg gtc atc atg atc act<br>Ser Val Lys Leu Cys Arg Gln Ala Gly Ile Arg Val Ile Met Ile Thr<br>        610                          615                         620 | 2412 |
| gga gac aac aaa ggc acc gct gtg gcc atc tgt cgc cgc att ggc atc<br>Gly Asp Asn Lys Gly Thr Ala Val Ala Ile Cys Arg Arg Ile Gly Ile<br>625                          630                            635                        640 | 2460 |
| ttt ggg cag gat gag gat gtg aca tca aag gct ttt aca ggg cga gag<br>Phe Gly Gln Asp Glu Asp Val Thr Ser Lys Ala Phe Thr Gly Arg Glu<br>                            645                          650                         655 | 2508 |
| ttt gat gaa tta agc cct tca gcc cag aga gat gcc tgc tta aat gcc<br>Phe Asp Glu Leu Ser Pro Ser Ala Gln Arg Asp Ala Cys Leu Asn Ala<br>        660                          665                         670 | 2556 |
| cgc tgt ttt gct cga gtt gaa cct tcc cac aag tct aag att gtt gag<br>Arg Cys Phe Ala Arg Val Glu Pro Ser His Lys Ser Lys Ile Val Glu<br>                            675                          680                         685 | 2604 |
| ttc ctt cag tcc ttt gat gag atc aca gct atg act ggt gat ggt gtg<br>Phe Leu Gln Ser Phe Asp Glu Ile Thr Ala Met Thr Gly Asp Gly Val<br>        690                          695                         700 | 2652 |

-continued

| | |
|---|---|
| aat gat gct cct gct ctg aag aaa tct gaa atc ggg att gcc atg ggc<br>Asn Asp Ala Pro Ala Leu Lys Lys Ser Glu Ile Gly Ile Ala Met Gly<br>705                        710                   715                   720 | 2700 |
| tca ggg act gca gtg gct aag act gct tct gag atg gtc ctg gca gat<br>Ser Gly Thr Ala Val Ala Lys Thr Ala Ser Glu Met Val Leu Ala Asp<br>                   725                   730                   735 | 2748 |
| gac aac ttc tcc acc att gtg gct gct gtt gag gag ggg cga gcc atc<br>Asp Asn Phe Ser Thr Ile Val Ala Ala Val Glu Glu Gly Arg Ala Ile<br>                740                   745                   750 | 2796 |
| tac aac aac atg aag cag ttc atc cgc tac ctc atc tca tcc aac gtg<br>Tyr Asn Asn Met Lys Gln Phe Ile Arg Tyr Leu Ile Ser Ser Asn Val<br>           755                   760                   765 | 2844 |
| ggg gaa gtg gtc tgt atc ttc ctg acg gca gcc ctt ggg ttt cct gag<br>Gly Glu Val Val Cys Ile Phe Leu Thr Ala Ala Leu Gly Phe Pro Glu<br>770                        775                   780 | 2892 |
| gct tta att cct gtc cag tta ctc tgg gtc aat ctg gtg aca gat ggt<br>Ala Leu Ile Pro Val Gln Leu Leu Trp Val Asn Leu Val Thr Asp Gly<br>785                        790                   795                   800 | 2940 |
| ctg cct gcc act gcg ctg ggg ttc aat cct cca gac ctg gac atc atg<br>Leu Pro Ala Thr Ala Leu Gly Phe Asn Pro Pro Asp Leu Asp Ile Met<br>                   805                   810                   815 | 2988 |
| aac aaa ccc ccc cgg aac cca aaa gaa cca ctg atc agc ggg tgg ctc<br>Asn Lys Pro Pro Arg Asn Pro Lys Glu Pro Leu Ile Ser Gly Trp Leu<br>               820                   825                   830 | 3036 |
| ttt ttc cgt tac ctg gct att ggc tgt tat gtt ggc gct gcc acc gtg<br>Phe Phe Arg Tyr Leu Ala Ile Gly Cys Tyr Val Gly Ala Ala Thr Val<br>835                        840                   845 | 3084 |
| ggt gct gct gca tgg tgg ttc atc gct gct gac ggc ggt cca aga gtc<br>Gly Ala Ala Ala Trp Trp Phe Ile Ala Ala Asp Gly Gly Pro Arg Val<br>850                        855                   860 | 3132 |
| tcc ttc tac cag ctg agt cat ttc cta cag tgt aag gag gac aac cca<br>Ser Phe Tyr Gln Leu Ser His Phe Leu Gln Cys Lys Glu Asp Asn Pro<br>865                        870                   875                   880 | 3180 |
| gac ttc gat gga gtg gat tgt gca atc ttt gag tcc cca tat cca atg<br>Asp Phe Asp Gly Val Asp Cys Ala Ile Phe Glu Ser Pro Tyr Pro Met<br>                   885                   890                   895 | 3228 |
| aca atg gca ctt tct gtt cta gta acc ata gag atg tgt aat gcc ctc<br>Thr Met Ala Leu Ser Val Leu Val Thr Ile Glu Met Cys Asn Ala Leu<br>               900                   905                   910 | 3276 |
| aac agc ttg tct gaa aac cag tct ttg ctg agg atg ccc ccc tgg gag<br>Asn Ser Leu Ser Glu Asn Gln Ser Leu Leu Arg Met Pro Pro Trp Glu<br>           915                   920                   925 | 3324 |
| aat atc tgg ctc gtg ggc tcc atc tgc ttg tcc atg tca ctt cac ttc<br>Asn Ile Trp Leu Val Gly Ser Ile Cys Leu Ser Met Ser Leu His Phe<br>930                        935                   940 | 3372 |
| ttg atc ctc tac gtg gaa cct ttg ccg ctc att ttc cag atc aca ccg<br>Leu Ile Leu Tyr Val Glu Pro Leu Pro Leu Ile Phe Gln Ile Thr Pro<br>945                        950                   955                   960 | 3420 |
| ctg aat ctg acc cag tgg ctg atg gtg ctg aaa atc tcc ttg cct gtg<br>Leu Asn Leu Thr Gln Trp Leu Met Val Leu Lys Ile Ser Leu Pro Val<br>                   965                   970                   975 | 3468 |
| atc ctc atg gat gag acg ctc aag ttt gtg gcc cga aac tac ctg gaa<br>Ile Leu Met Asp Glu Thr Leu Lys Phe Val Ala Arg Asn Tyr Leu Glu<br>               980                   985                   990 | 3516 |
| caa ccc gca ata ctg gag taa ccgcttccta aaccatttgc agaaatataa<br>Gln Pro Ala Ile Leu Glu<br>           995 | 3567 |
| gggtgttcgg gtgcgtgcat gtgcgttgtt agcaacacat ctaccagccc tctgcatgac | 3627 |
| tgaggttggg gaaagaaaaa atagaaacag tcccccaactc actgtgtgat gtggaggaaa | 3687 |

```
tgtgtattac cagtggggtt ttagctgttc aatcaaaata ataacaaatg tacaatttag    3747
cataacaaat cagagagcct ctccagagaa gttggtttct ttgctgcgag aaggaggttc    3807
tgaaacctta tccaagaaca gaagccatca gccaagtctc cacatttctc tgcaaaatgt    3867
catagcctct ctaactgtat gataattgta atgcatgcct tcagttgtaa gtggccagat    3927
tgctctacag tgacattgaa acatgctttc taatgggccc tgtacagttt gcttatttat    3987
aaattcattt aaaacactac agctgctgaa tggttacaac ataggcctcc agtcctaact    4047
tcagttgttt aggtgtgcag ccagctgttc cacactgtat tattgtaact tatttaatga    4107
agtcagaagc agtagacaga tgttggtgca atacaagtat tgtgtgcatt tatcgtaata    4167
aagtgctcag cgtcagttca gttgctcaca gcttctcaca gcgcatgttt gactgtagtc    4227
tgtaaataga ggtcagtttc tgtgctggta acaggtattg cacagacatg atttcaggta    4287
aataaatcta ttctacgata aaccctcaaa aaaaaaaaaa aaaaaaaaaa aaaaaaaaaa    4347
aaaaaa                                                               4353
```

<210> SEQ ID NO 8
<211> LENGTH: 998
<212> TYPE: PRT
<213> ORGANISM: Mus musculus

<400> SEQUENCE: 8

```
Met Glu Asn Ala His Thr Lys Thr Val Glu Val Leu Gly His Phe
1               5                   10                  15

Gly Val Asn Glu Ser Thr Gly Leu Ser Leu Glu Gln Val Lys Lys Leu
            20                  25                  30

Lys Glu Arg Trp Gly Ser Asn Glu Leu Pro Ala Glu Gly Lys Thr
        35                  40                  45

Leu Leu Glu Leu Val Ile Glu Gln Phe Glu Asp Leu Leu Val Arg Ile
    50                  55                  60

Leu Leu Leu Ala Ala Cys Ile Ser Phe Val Leu Ala Trp Phe Glu Glu
65                  70                  75                  80

Gly Glu Glu Thr Ile Thr Ala Phe Val Glu Pro Phe Val Ile Leu Leu
                85                  90                  95

Ile Leu Val Ala Asn Ala Ile Val Gly Val Trp Gln Glu Arg Asn Ala
            100                 105                 110

Glu Asn Ala Ile Glu Ala Leu Lys Glu Tyr Glu Pro Glu Met Gly Lys
        115                 120                 125

Val Tyr Arg Gln Asp Arg Lys Ser Val Gln Arg Ile Lys Ala Lys Asp
    130                 135                 140

Ile Val Pro Gly Asp Ile Val Glu Ile Ala Val Gly Asp Lys Val Pro
145                 150                 155                 160

Ala Asp Ile Arg Leu Thr Ser Ile Lys Ser Thr Thr Leu Arg Val Asp
                165                 170                 175

Gln Ser Ile Leu Thr Gly Glu Ser Val Ser Val Ile Lys His Thr Asp
            180                 185                 190

Pro Val Pro Asp Pro Arg Ala Val Asn Gln Asp Lys Lys Asn Met Leu
        195                 200                 205

Phe Ser Gly Thr Asn Ile Ala Ala Gly Lys Ala Met Gly Val Val Val
    210                 215                 220

Ala Thr Gly Val Asn Thr Glu Ile Gly Lys Ile Arg Asp Glu Met Val
225                 230                 235                 240

Ala Thr Glu Gln Glu Arg Thr Pro Leu Gln Gln Lys Leu Asp Glu Phe
```

-continued

```
                        245                 250                 255
Gly Glu Gln Leu Ser Lys Val Ile Ser Leu Ile Cys Ile Ala Val Trp
            260                 265                 270

Ile Ile Asn Ile Gly His Phe Asn Asp Pro Val His Gly Ser Trp
        275                 280                 285

Ile Arg Gly Ala Ile Tyr Tyr Phe Lys Ile Ala Val Ala Leu Ala Val
        290                 295                 300

Ala Ala Ile Pro Glu Gly Leu Pro Ala Val Ile Thr Thr Cys Leu Ala
305                 310                 315                 320

Leu Gly Thr Arg Arg Met Ala Lys Lys Asn Ala Ile Val Arg Ser Leu
                325                 330                 335

Pro Ser Val Glu Thr Leu Gly Cys Thr Ser Val Ile Cys Ser Asp Lys
                340                 345                 350

Thr Gly Thr Leu Thr Thr Asn Gln Met Ser Val Cys Arg Met Phe Ile
                355                 360                 365

Leu Asp Lys Val Glu Gly Asp Thr Cys Ser Leu Asn Glu Phe Ser Ile
            370                 375                 380

Thr Gly Ser Thr Tyr Ala Pro Ile Gly Glu Val Gln Lys Asp Asp Lys
385                 390                 395                 400

Pro Val Lys Cys His Gln Tyr Asp Gly Leu Val Glu Leu Ala Thr Ile
                405                 410                 415

Cys Ala Leu Cys Asn Asp Ser Ala Leu Asp Tyr Asn Glu Ala Lys Gly
                420                 425                 430

Val Tyr Glu Lys Val Gly Glu Ala Thr Glu Thr Ala Leu Thr Cys Leu
                435                 440                 445

Val Glu Lys Met Asn Val Phe Asp Thr Glu Leu Lys Gly Leu Ser Lys
            450                 455                 460

Ile Glu Arg Ala Asn Ala Cys Asn Ser Val Ile Lys Gln Leu Met Lys
465                 470                 475                 480

Lys Glu Phe Thr Leu Glu Phe Ser Arg Asp Arg Lys Ser Met Ser Val
                485                 490                 495

Tyr Cys Thr Pro Asn Lys Pro Ser Arg Thr Ser Met Ser Lys Met Phe
                500                 505                 510

Val Lys Gly Ala Pro Glu Gly Val Ile Asp Arg Cys Thr His Ile Arg
            515                 520                 525

Val Gly Ser Thr Lys Val Pro Met Thr Pro Gly Val Lys Gln Lys Ile
            530                 535                 540

Met Ser Val Ile Arg Glu Trp Gly Ser Gly Ser Asp Thr Leu Arg Cys
545                 550                 555                 560

Leu Ala Leu Ala Thr His Asp Asn Pro Leu Lys Arg Glu Glu Met His
                565                 570                 575

Leu Glu Asp Ser Ala Asn Phe Ile Lys Tyr Glu Thr Asn Leu Thr Phe
            580                 585                 590

Val Gly Cys Val Gly Met Leu Asp Pro Pro Arg Ile Glu Val Ala Ser
            595                 600                 605

Ser Val Lys Leu Cys Arg Gln Ala Gly Ile Arg Val Ile Met Ile Thr
            610                 615                 620

Gly Asp Asn Lys Gly Thr Ala Val Ala Ile Cys Arg Arg Ile Gly Ile
625                 630                 635                 640

Phe Gly Gln Asp Glu Asp Val Thr Ser Lys Ala Phe Thr Gly Arg Glu
                645                 650                 655

Phe Asp Glu Leu Ser Pro Ser Ala Gln Arg Asp Ala Cys Leu Asn Ala
                660                 665                 670
```

Arg Cys Phe Ala Arg Val Glu Pro Ser His Lys Ser Lys Ile Val Glu
        675                 680                 685

Phe Leu Gln Ser Phe Asp Glu Ile Thr Ala Met Thr Gly Asp Gly Val
        690                 695                 700

Asn Asp Ala Pro Ala Leu Lys Lys Ser Glu Ile Gly Ile Ala Met Gly
705                 710                 715                 720

Ser Gly Thr Ala Val Ala Lys Thr Ala Ser Glu Met Val Leu Ala Asp
            725                 730                 735

Asp Asn Phe Ser Thr Ile Val Ala Ala Val Glu Glu Gly Arg Ala Ile
            740                 745                 750

Tyr Asn Asn Met Lys Gln Phe Ile Arg Tyr Leu Ile Ser Ser Asn Val
        755                 760                 765

Gly Glu Val Val Cys Ile Phe Leu Thr Ala Ala Leu Gly Phe Pro Glu
        770                 775                 780

Ala Leu Ile Pro Val Gln Leu Leu Trp Val Asn Leu Val Thr Asp Gly
785                 790                 795                 800

Leu Pro Ala Thr Ala Leu Gly Phe Asn Pro Pro Asp Leu Asp Ile Met
            805                 810                 815

Asn Lys Pro Pro Arg Asn Pro Lys Glu Pro Leu Ile Ser Gly Trp Leu
            820                 825                 830

Phe Phe Arg Tyr Leu Ala Ile Gly Cys Tyr Val Gly Ala Ala Thr Val
        835                 840                 845

Gly Ala Ala Ala Trp Trp Phe Ile Ala Ala Asp Gly Gly Pro Arg Val
        850                 855                 860

Ser Phe Tyr Gln Leu Ser His Phe Leu Gln Cys Lys Glu Asp Asn Pro
865                 870                 875                 880

Asp Phe Asp Gly Val Asp Cys Ala Ile Phe Glu Ser Pro Tyr Pro Met
            885                 890                 895

Thr Met Ala Leu Ser Val Leu Val Thr Ile Glu Met Cys Asn Ala Leu
            900                 905                 910

Asn Ser Leu Ser Glu Asn Gln Ser Leu Leu Arg Met Pro Pro Trp Glu
        915                 920                 925

Asn Ile Trp Leu Val Gly Ser Ile Cys Leu Ser Met Ser Leu His Phe
        930                 935                 940

Leu Ile Leu Tyr Val Glu Pro Leu Pro Leu Ile Phe Gln Ile Thr Pro
945                 950                 955                 960

Leu Asn Leu Thr Gln Trp Leu Met Val Leu Lys Ile Ser Leu Pro Val
            965                 970                 975

Ile Leu Met Asp Glu Thr Leu Lys Phe Val Ala Arg Asn Tyr Leu Glu
            980                 985                 990

Gln Pro Ala Ile Leu Glu
        995

<210> SEQ ID NO 9
<211> LENGTH: 1078
<212> TYPE: DNA
<213> ORGANISM: Homo sapiens
<220> FEATURE:
<221> NAME/KEY: misc_feature
<223> OTHER INFORMATION: Human SUMO-1 polynucleotide

<400> SEQUENCE: 9
gcggaagtga cgcgaggcgt agcggaagtt actgcagccg cggtgttgtg ctgtggggaa      60
gggagaagga tttgtaaacc ccggagcgag gttctgctta cccgaggccg ctgctgtgcg     120

| | |
|---|---|
| gagaccccg ggtgaagcca ccgtcatcat gtctgaccag gaggcaaaac cttcaactga | 180 |
| ggacttgggg gataagaagg aaggtgaata tattaaactc aaagtcattg gacaggatag | 240 |
| cagtgagatt cacttcaaag tgaaaatgac aacacatctc aagaaactca agaatcata | 300 |
| ctgtcaaaga cagggtgttc caatgaattc actcaggttt ctctttgagg gtcagagaat | 360 |
| tgctgataat catactccaa agaactggga atggaggaa gaagatgtga ttgaagttta | 420 |
| tcaggaacaa acgggggtc attcaacagt ttagttttaa aatttgaggg tctggaccaa | 480 |
| aagaagagga atatcaggtt gaagtcaaga tgacagataa ggtgagagta atgactaact | 540 |
| ccaaagatgg cttcactgaa gaaaaggcat tttaagattt tttaaaaatc ttgtcagaag | 600 |
| atcccagaaa agttctaatt ttcattagca attaataaag ctatacatgc agaaatgaat | 660 |
| acaacgaac actgctcttt ttgattttat ttgtactttt tggcctggga tatgggtttt | 720 |
| aaatggacat tgtctgtacc agcttcatta aaataaacaa tatttgtaaa aatcatacta | 780 |
| atgcttattt tattttaatt gtatagaaag aaaaaaatgc ctaaaataag gttttcttgc | 840 |
| ataaatactg gaaattgcac atggtacaaa tttttttcttc attactgtac agtgatgatg | 900 |
| ttaatgactt tgaagcactg aaagttactg aagtgccttc tgaatcaagg atttaattaa | 960 |
| ggccacaata cctttttaat actcagtgtt ctgtttttt aaaaacttga tattcctgta | 1020 |
| tggtgcatat atgatacagt tacctaatca tgttgaataa atgggcatgc caaaaatt | 1078 |

```
<210> SEQ ID NO 10
<211> LENGTH: 101
<212> TYPE: PRT
<213> ORGANISM: Homo sapiens
<220> FEATURE:
<221> NAME/KEY: MISC_FEATURE
<223> OTHER INFORMATION: Human SUMO-1 amino acid sequence

<400> SEQUENCE: 10

Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Lys
        35                  40                  45

Glu Ser Tyr Cys Gln Arg Gln Gly Val Pro Met Asn Ser Leu Arg Phe
    50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln Glu Gln Thr Gly
                85                  90                  95

Gly His Ser Thr Val
            100

<210> SEQ ID NO 11
<211> LENGTH: 306
<212> TYPE: DNA
<213> ORGANISM: Sus scrofa
<220> FEATURE:
<221> NAME/KEY: misc_feature
<223> OTHER INFORMATION: Pig SUMO-1 polynucleotide

<400> SEQUENCE: 11
```

| | |
|---|---|
| atgtctgacc aggaggcaaa accttcaact gaggacttgg gtgataagaa ggaaggagag | 60 |
| tacattaaac tcaaagtcat tggacaggat agcagtgaga ttcacttcaa agtgaaaatg | 120 |

```
acgacacatc tcaagaaact caaagaatca tactgtcaaa gacagggcgt tccaatgaat    180
tcactcaggt ttctctttga aggtcagaga attgctgata atcacactcc aaaagaactg    240
ggaatggagg aagaagatgt gattgaagtt tatcaggaac aaacagggggg tcactcaacg   300 gtttag                                                               306
```

```
<210> SEQ ID NO 12
<211> LENGTH: 101
<212> TYPE: PRT
<213> ORGANISM: Sus scrofa
<220> FEATURE:
<221> NAME/KEY: MISC_FEATURE
<223> OTHER INFORMATION: Pig SUMO-1 amino acid sequence

<400> SEQUENCE: 12
```

```
Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Lys
        35                  40                  45

Glu Ser Tyr Cys Gln Arg Gln Gly Val Pro Met Asn Ser Leu Arg Phe
    50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln Glu Gln Thr Gly
                85                  90                  95

Gly His Ser Thr Val
            100
```

```
<210> SEQ ID NO 13
<211> LENGTH: 1150
<212> TYPE: DNA
<213> ORGANISM: Rattus norvegicus
<220> FEATURE:
<221> NAME/KEY: misc_feature
<223> OTHER INFORMATION: Rat SUMO-1 polynucleotide

<400> SEQUENCE: 13
```

```
ccgctgtggt gcggagaccc ccgggtgaat ccaccgacac catgtctgac caggaggcaa    60
aaccttcaac tgaggactta ggagataaga agaaggaga atacattaaa ctcaaagtta    120
ttggacagga cagcagtgag atccatttca agtgaaaat gacaacacat ctcaagaagc    180
tcaaagaatc gtactgtcaa agacaggagt tccaatgaa ttcactcagg tttctctttg    240
aaggtcagag aattgctgat aatcatactc caaaagaact gggaatggag gaagaagacg    300
tgattgaagt ttatcaggaa caaacggggg gtcactcgac ggtttagata attcttttta    360 tttttttattt tttcctttttc cctcaatcct tttttatttt taaaaatagt tcttttgtaa    420
tgtggtgttc aaaatgaaaa ttgaatactg cactccatc tcttagaaca tctggtaatc    480
tgaattctag tgttcaatat tcattattgg ttgttttgt tgtgctgatt tttggtgatc    540
agacctcagc tcccttaaca ttgcccttct tcctttaaga gatttcatgt gtgcacacag    600
agaggccacc ctttccagga ctgtgcattt tcagggttgt gatgataaaa ggatcgacta    660
atgggagctt ccctgtgacc tttcaatggc cctgcagttc cggtatgtgg ttgcttcact    720
cctggactat gatttcagt gggagatgga gattttcag agaaccgaac tgtgaaaat    780 gaccttttct cagcttgaag ctactttaa aatctgaggg tctggaccaa agaagaaca    840
```

| | |
|---|---|
| tcatgtttgt agtcaaggta acagatacag tgagagtaac agctaactcc aaaagtggct | 900 |
| tcactggaga gaaagaaagt gtcttgagca agacagtatt gtcagaagat cccaggaaag | 960 |
| ttctaatctt catcagcagt taataataaa gttactcata cagaagtgta cgcaacagac | 1020 |
| actgctcctt tgattctgt tgtactttt ggcctgggac atgggttttc aagggacatc | 1080 |
| atctgtacca gcttcattaa aataaacaat atttgtaaaa accgtaaaaa aaaaaaaaaa | 1140 |
| aaaaaaaaaa | 1150 |

```
<210> SEQ ID NO 14
<211> LENGTH: 101
<212> TYPE: PRT
<213> ORGANISM: Rattus norvegicus
<220> FEATURE:
<221> NAME/KEY: MISC_FEATURE
<223> OTHER INFORMATION: Rat SUMO-1 amino acid sequence

<400> SEQUENCE: 14
```

Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Lys
        35                  40                  45

Glu Ser Tyr Cys Gln Arg Gln Gly Val Pro Met Asn Ser Leu Arg Phe
    50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln Glu Gln Thr Gly
                85                  90                  95

Gly His Ser Thr Val
            100

```
<210> SEQ ID NO 15
<211> LENGTH: 1230
<212> TYPE: DNA
<213> ORGANISM: Mus musculus
<220> FEATURE:
<221> NAME/KEY: misc_feature
<223> OTHER INFORMATION: Mouse SUMO-1 polynucleotide

<400> SEQUENCE: 15
```

| | |
|---|---|
| ggaagtgacg caagacgtag aggaagtccc tgcagccgcg gtgttgtgct gtagagaagg | 60 |
| gacggatttg taaacctcag agtgaggttc tgcctgccgg aggccgcagt ggtgcggaga | 120 |
| ccccgggtg aatccacgtc accatgtctg accaggaggc aaaaccttca actgaggact | 180 |
| taggcgataa gaaggaagga gaatacatta aactcaaagt tattggacag atagcagtg | 240 |
| agatacattt caaagtgaaa atgacaacac atctcaagaa actcaaagaa tcatactgtc | 300 |
| aaagacaggg agtccaatg aattcactca ggtttctctt tgaaggtcag agaattgctg | 360 |
| ataatcatac tccgaaagaa ctgggaatgg aggaagaaga tgtgattgaa gtttatcagg | 420 |
| aacaaacggg gggtcactcg acggtttaga taattctttt tattttttat ttttcctttc | 480 |
| cctcaatcct ttttatttt taaaaatagt tcttttgtaa tgtggtgttc aaaatgaaaa | 540 |
| ttgaatactg gcactccatc tcttagaaca tatgaattct agtgttcaat attcattatt | 600 |
| ggttgttttt gttgtgctga ttttggtga tcagacctca gctcccttaa tactgccctt | 660 |
| tttcctttaa gagatttcat gtgtgcacag agaggccacc cttttcagga ctgtgcattt | 720 |

-continued

```
tcaggtttgt gatgataaaa agatcgacca atgggagctt tcctatgacc tttcaattgg    780
ctctgaagtt ccagcatgtg gttgcttcac tcctggactg tgattttcag tgggagatgg    840 aaattttca gagaactgaa ctgtggaaaa tgacctttcc tcagcttgaa gctacttta    900 aaatctgcgg gtctggacca aaagaagaac atcatgtttg tagtcaagat gacagataca    960
gtgagagcaa cagctaactc caaaggtggc ttcactggag agaaagaaag tgtcttgagc    1020
aagacagtat tgtcagaaga tcccaggaaa gttctaatgt tcatcagcag ttattaataa    1080
agttactcat acagaagtgt acgcaacaga cactgctttt gattctgttt gtacttttg    1140 gcctgggaca tgggttttca agggacatcg tctgtaccag cttcattaaa ataaacaata    1200
tttgtaaaaa cattaaaaaa aaaaaaaaaa    1230
```

<210> SEQ ID NO 16
<211> LENGTH: 101
<212> TYPE: PRT
<213> ORGANISM: Mus musculus
<220> FEATURE:
<221> NAME/KEY: MISC_FEATURE
<223> OTHER INFORMATION: Mouse SUMO-1 amino acid sequence

<400> SEQUENCE: 16

```
Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Lys
        35                  40                  45

Glu Ser Tyr Cys Gln Arg Gln Gly Val Pro Met Asn Ser Leu Arg Phe
    50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln Glu Gln Thr Gly
                85                  90                  95

Gly His Ser Thr Val
            100
```

<210> SEQ ID NO 17
<211> LENGTH: 21
<212> TYPE: PRT
<213> ORGANISM: Artificial Sequence
<220> FEATURE:
<223> OTHER INFORMATION: Synthetic Polynucleotide

<400> SEQUENCE: 17

```
Ala Ala Gly Gly Thr Cys Ala Gly Ala Gly Ala Thr Thr Gly Cys
1               5                   10                  15

Thr Gly Ala Thr Ala
            20
```

<210> SEQ ID NO 18
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 18

```
gggatacgat tgaactagta a                                               21
```